US011034755B2

(12) United States Patent
Silence

(10) Patent No.: US 11,034,755 B2
(45) Date of Patent: Jun. 15, 2021

(54) POLYPEPTIDES AND POLYPEPTIDE CONSTRUCTS COMPRISING SINGLE DOMAIN ANTIBODIES DIRECTED AGAINST VON WILLEBRAND FACTOR

(71) Applicant: Ablynx N.V., Ghent-Zwijnaarde (BE)

(72) Inventor: Karen Silence, Overijse (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 113 days.

(21) Appl. No.: 16/142,063

(22) Filed: Sep. 26, 2018

(65) Prior Publication Data

US 2019/0112363 A1 Apr. 18, 2019

Related U.S. Application Data

(60) Division of application No. 14/669,025, filed on Mar. 26, 2015, now Pat. No. 10,112,989, which is a continuation of application No. 10/541,708, filed as application No. PCT/BE2004/000002 on Jan. 9, 2004, now Pat. No. 9,028,816, which is a continuation-in-part of application No. PCT/EP03/06581, filed on Jun. 23, 2003, and a continuation-in-part of application No. PCT/EP03/07313, filed on Jul. 8, 2003, and a continuation-in-part of application No. PCT/BE03/00193, filed on Nov. 7, 2003, and a continuation-in-part of application No. PCT/BE03/00189, filed on Nov. 7, 2003, and a continuation-in-part of application No. PCT/BE03/00190, filed on Nov. 7, 2003, and a
(Continued)

(30) Foreign Application Priority Data

Jan. 10, 2003 (EP) .................................. 03447005

(51) Int. Cl.
| | |
|---|---|
| *C07K 16/36* | (2006.01) |
| *C07K 16/18* | (2006.01) |
| *A61K 38/16* | (2006.01) |
| *A61K 38/49* | (2006.01) |
| *C07K 16/28* | (2006.01) |
| *G01N 33/86* | (2006.01) |
| *A61K 39/395* | (2006.01) |
| *A61K 45/06* | (2006.01) |
| *A61L 29/08* | (2006.01) |
| *A61L 29/16* | (2006.01) |
| *A61L 31/10* | (2006.01) |
| *A61L 31/16* | (2006.01) |
| *G01N 33/68* | (2006.01) |
| *A61K 39/00* | (2006.01) |

(52) U.S. Cl.
CPC ............ *C07K 16/18* (2013.01); *A61K 38/166* (2013.01); *A61K 38/49* (2013.01); *A61K 39/3955* (2013.01); *A61K 45/06* (2013.01); *A61L 29/085* (2013.01); *A61L 29/16* (2013.01); *A61L 31/10* (2013.01); *A61L 31/16* (2013.01); *C07K 16/2896* (2013.01); *C07K 16/36* (2013.01); *G01N 33/68* (2013.01); *G01N 33/6893* (2013.01); *G01N 33/86* (2013.01); *A61K 2039/505* (2013.01); *A61L 2300/256* (2013.01); *A61L 2300/42* (2013.01); *A61L 2420/02* (2013.01); *C07K 2317/22* (2013.01); *C07K 2317/24* (2013.01); *C07K 2317/31* (2013.01); *C07K 2317/34* (2013.01); *C07K 2317/569* (2013.01); *G01N 2333/47* (2013.01); *G01N 2333/755* (2013.01); *G01N 2500/02* (2013.01); *G01N 2500/04* (2013.01); *G01N 2800/222* (2013.01)

(58) Field of Classification Search
None
See application file for complete search history.

(56) References Cited

U.S. PATENT DOCUMENTS

| | | |
|---|---|---|
| 5,051,264 A | 9/1991 | Ambrus |
| 5,238,919 A | 8/1993 | Zimmerman et al. |

(Continued)

FOREIGN PATENT DOCUMENTS

| | | |
|---|---|---|
| EP | 0 295 645 A2 | 12/1988 |
| EP | 0 368 684 B1 | 3/1994 |

(Continued)

OTHER PUBLICATIONS

Janeway et al., Immunobiology, 3rd edition, 19097, Garland Press, pp. 3:1-3:11.*

(Continued)

*Primary Examiner* — Michael Szperka
(74) *Attorney, Agent, or Firm* — Wolf, Greenfield & Sacks, P.C.

(57) ABSTRACT

The present invention relates to polypeptides comprising at least one single domain antibody directed against vWF, vWF A1 domain, A1 domain of activated vWF, vWF A3 domain, gpIb and/or collagen, homologues of said polypeptides, and/or functional portions of said polypeptides, for the treatment for conditions which require a modulation of platelet-mediated aggregation and which overcomes the problems of the prior art. A further aspect of the invention is methods of production of said polypeptides, methods to coat devices with such polypeptides used in medical procedures (e.g. PCTA, stenting), methods and kits for screening for agents that modulate platelet-mediated aggregation and kits for the diagnosis of diseases related to platelet-mediated aggregation.

4 Claims, 19 Drawing Sheets

Figure 1:
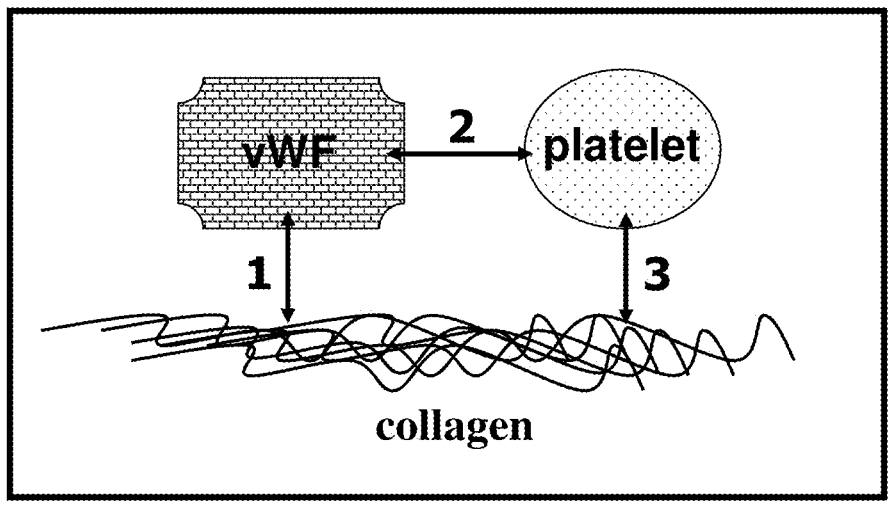

Specification includes a Sequence Listing.

Related U.S. Application Data continuation-in-part of application No. PCT/BE03/00192, filed on Nov. 7, 2003, and a continuation-in-part of application No. PCT/BE03/00194, filed on Nov. 7, 2003, and a continuation-in-part of application No. PCT/BE03/00206, filed on Dec. 1, 2003, and a continuation-in-part of application No. PCT/BE03/00191, filed on Dec. 2, 2003.

(56) References Cited

U.S. PATENT DOCUMENTS

| | | | |
|---|---|---|---|
| 5,670,132 | A | 9/1997 | Griffiths et al. |
| 5,916,805 | A | 6/1999 | Nagano et al. |
| 5,976,532 | A | 11/1999 | Coller et al. |
| 6,228,360 | B1 | 5/2001 | Co et al. |
| 6,251,393 | B1 | 6/2001 | Handin et al. |
| 6,280,731 | B1 | 8/2001 | Nagano et al. |
| 6,419,934 | B1 | 7/2002 | Tobinick |
| 6,517,829 | B1 * | 2/2003 | Frenken ............ A61K 8/64 424/150.1 |
| 6,759,518 | B1 | 7/2004 | Kontermann et al. |
| 6,793,920 | B2 | 9/2004 | Nagano et al. |
| 7,311,913 | B2 | 12/2007 | Co et al. |
| 7,771,724 | B2 | 8/2010 | Huizinga et al. |
| 7,807,162 | B2 | 10/2010 | Silence |
| 7,939,277 | B2 | 5/2011 | De Groot et al. |
| 8,372,398 | B2 | 2/2013 | Silence |
| 9,028,816 | B2 | 5/2015 | Silence |
| 2001/0024647 | A1 | 9/2001 | Handin et al. |
| 2002/0028203 | A1 | 3/2002 | Blumberg |
| 2002/0028204 | A1 | 3/2002 | Nagano et al. |
| 2002/0058033 | A1 | 5/2002 | Raisch et al. |
| 2003/0092892 | A1 | 5/2003 | Frenken et al. |
| 2005/0054001 | A1 | 3/2005 | Muyldermans |
| 2005/0136056 | A1 | 6/2005 | Kageyama et al. |
| 2005/0192224 | A1 | 9/2005 | Huizinga et al. |
| 2006/0149041 | A1 | 7/2006 | Silence |
| 2006/0183702 | A1 | 8/2006 | Diener et al. |
| 2006/0286066 | A1 | 12/2006 | Basran |
| 2008/0096223 | A1 | 4/2008 | De Groot et al. |
| 2010/0022452 | A1 | 1/2010 | Silence et al. |
| 2010/0330084 | A1 | 12/2010 | Silence |
| 2011/0158996 | A1 | 6/2011 | Holz et al. |
| 2012/0321640 | A1 | 12/2012 | Van Roy et al. |
| 2013/0136736 | A1 | 5/2013 | Silence |
| 2014/0044710 | A1 | 2/2014 | Holz et al. |
| 2019/0112363 | A1 | 4/2019 | Silence et al. |

FOREIGN PATENT DOCUMENTS

| | | |
|---|---|---|
| EP | 0 795 608 A1 | 9/1997 |
| EP | 0 952 218 A2 | 10/1999 |
| EP | 1 002 861 A1 | 5/2000 |
| EP | 3447005.4 A1 | 1/2003 |
| WO | WO 90/10707 A1 | 9/1990 |
| WO | WO 93/11161 A1 | 6/1993 |
| WO | WO 94/04678 A1 | 3/1994 |
| WO | WO 94/13806 A1 | 6/1994 |
| WO | WO 94/25591 A1 | 11/1994 |
| WO | WO 96/017078 A1 | 6/1996 |
| WO | WO 97/38102 A1 | 10/1997 |
| WO | WO 99/09055 A2 | 2/1999 |
| WO | WO 99/23221 A2 | 5/1999 |
| WO | WO 00/24781 A1 | 5/2000 |
| WO | WO 01/002853 A2 | 1/2001 |
| WO | WO 02/051351 A2 | 7/2002 |
| WO | WO 02/057445 A1 | 7/2002 |
| WO | WO 03/035694 A2 | 5/2003 |
| WO | PCT/EP03/06581 | 6/2003 |
| WO | PCT/EP03/07313 | 7/2003 |
| WO | PCT/BE03/00191 | 12/2003 |
| WO | PCT/BE03/00206 | 12/2003 |
| WO | WO 2004/003019 A2 | 1/2004 |
| WO | WO 2004/015425 A1 | 2/2004 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2004/062551 A2 | 7/2004 |
| WO | WO 2005/044858 A1 | 5/2005 |
| WO | WO 2006/074947 A2 | 7/2006 |
| WO | WO 2006/122825 A2 | 11/2006 |
| WO | WO 2008/049881 A3 | 5/2008 |

OTHER PUBLICATIONS

Rudikoff et al., Proc Natl Acad Sci USA. Mar. 1982;79{6}:1979-83.*

Ghahroudi et al., FEBS Letters, 1997, 414:521-526.*

Edwards et al., J Mol Biol. Nov. 14, 2003;334(1): 103-18.*

Lloyd et al., Protein Eng Des Sel. Mar. 2009;22(3):159-68. doi: 10.1093/protein/gzn058. Epub Oct. 29, 2008.*

Goel et al., J Immunol. Dec. 15, 2004; 173(12)7358-67.*

Kanyavuz et al., Nat Rev Immunol. Jun. 2019;19(6):355-368. doi: 10.1038/S41577-019-0126-7.*

[No Author Listed] Cerebral Infarction. Wikipedia Foundation. Apr. 13, 2014.

[No Author Listed] Embolism. Www.wikipedia.org. Accessed Apr. 19, 2010.

[No Author Listed] Immunochemistry. Nankodo Co., Ltd., Jul. 15, 1983 (1st ed.), pp. 35-36.

[No Author Listed] Platelet. www.wikipedia.org. Retrieved Jan. 7, 2013. 9 pages.

[No Author Listed] The Merck Manual of Diagnosis and Therapy, 17th Ed. Beers et al, Editors. Merck Research Laboratories, 1999:2057-8.

[No Author Listed] The Merck Manual of Diagnosis and Therapy, 17th Ed. Beers et al, Editors. Merck Research Laboratories, 1999:925-8.

[No Author Listed] Translational research in the development of Nanobody®-based therapies: vWF programme—a case study. Preclinical and Clinical Development of Therapeutic Antibodies. Ablynx Presentation. PEGS Meeting (Boston): Apr. 7, 2009. Slides 1-27.

[No Author Listed] Treatment of platelet-mediated aggregation diseases. 1 page. Submitted in counterpart or related Chinese application No. 200680024012.1. Received on Jan. 9, 2013.

[No Author Listed] Von Willebrand disease. www.wikipedia.org. Accessed Dec. 30, 2008.

AAP82060 standard protein 20 AA (sequence from EP 0 295 645).

AAR40233 standard protein 15 AA (Sequence from U.S. Pat. No. 5,238,919).

Genbank submission; NIH/NCBI; Accession No. 1AUQ; Emsley et al; Sep. 1, 1997 (last submission).

Genbank submission; NIH/NCBI; Accession No. 1M10_A; Huizinga et al; Sep. 25, 2008 (last submission).

Genbank submission; NIH/NCBI; Accession No. AAA61295; Mancuso et al.; Jan. 14, 1995 (last submission).

Genbank submission; NIH/NCBI; Accession No. AAB34053; Clerc et al.; Jul. 27, 1995 (last submission).

Genbank submission; NIH/NCBI; Accession No. AAB39987; Schulte am Esch II et al.; Jan. 9, 1997 (last submission).

Genbank submission; NIH/NCBI; Accession No. AAB59512; Sadler; Aug. 7, 1995 (last submission).

Genbank submission; NIH/NCBI; Accession No. CAA27972; Bonthron et al.; Jan. 9, 1998 (last submission).

Genbank submission; NIH/NCBI; Accession No. NP_000164; Forestier et al.; Jan. 4, 2009; (last submission).

Genbank submission; NIH/NCBI; Accession No. NP_000543; Sun et al.; Jan. 4, 2009; (last submission).

Genbank submission; NIH/NCBI; Accession No. 1SQ0_A; Dumas et al.; Sep. 24, 2008 (last submission).

Arbabi Gharoudi et al., Selection and identification of single domain antibody fragments from camel heavy-chain antibodies. FEBS Lett. Sep. 15, 1997;414(3):521-6.

Badreldin et al., Gaseous emboli during off-pump surgery with T-graft technique, two different mechanisms. Interact Cardiovasc Thorac Surg. May 2010;10(5):766-9. Epub Feb. 12, 2010.

(56) References Cited

OTHER PUBLICATIONS

Bartunek et al., Abstract 15084: safety and efficacy of Anti-vonWillebrand Factor nanobody® ALX-0081 in stable angina patients undergoing Percutaneous Coronary Intervention. Circ. Abstracts from Sci Sessions 2010. Nov. 23, 2010;122(21):Supplement A15084. 2 pages.

Bartunek et al., Abstract 2009: ALX-0081 a novel anti-thrombotic: results of a single-dose Phase 1 study in healthy volunteers and further development in patients with stable angina undergoing PCI. Circ. Abstracts from Sci Sessions 2008. Oct. 28, 2008;118(18):Supplement 656. 1 page.

Bartunek et al., Novel antiplatelet agents: ALX-0081, a Nanobody directed towards von Willebrand factor. J Cardiovasc Transl Res. Jun. 2013;6(3):355-63. doi: 10.1007/s12265-012-9435-y. Epub Jan. 11, 2013.

Bassand et al., Guidelines for the diagnosis and treatment of non-ST-segment elevation acute coronary syndromes. Eur Heart J. Jul. 2007;28(13):1598-660. Epub Jun. 14, 2007.

Berndt et al., The vascular biology of the glycoprotein Ib-IX-V complex. Thromb Haemost. Jul. 2001;86(1):178-88. Review.

Blanco et al., Formation and stability of beta-hairpin structures in polypeptides. Curr Opin Struct Biol. Feb. 1998;8(1):107-11. Review.

Bonnefoy et al., Shielding the front-strand beta 3 of the von Willebrand factor A1 domain inhibits its binding to platelet glycoprotein Ibalpha. Blood. Feb. 15, 2003;101(4):1375-83. Epub Oct. 10, 2002.

Callewaert et al., Evaluation of efficacy and safety of the anti-VWF Nanobody ALX-0681 in a preclinical baboon model of acquired thrombotic thrombocytopenic purpura. Blood. Oct. 25, 2012;120(17):3603-10. doi: 10.1182/blood-2012-04-420943. Epub Sep. 4, 2012.

Celikel et al., Crystal structure of the von Willebrand factor A1 domain in complex with the function blocking NMC-4 Fab. Nat Struct Biol. Mar. 1998;5(3):189-94.

Celikel et al., von Willebrand factor conformation and adhesive function is modulated by an internalized water molecule. Nat Struct Biol. Oct. 2000;7(10):881-4.

Chand et al., A two-site, monoclonal antibody-based immunoassay for von Willebrand factor—demonstration that vWF function resides in a conformational epitope. Thromb Haemost. Jun. 30, 1986;55(3):318-24.

Christophe et al., A monoclonal antibody (B724) to von Willebrand factor recognizing an epitope within the A1 disulphide loop (Cys509-Cys695) discriminates between type 2A and type 2B von Willebrand disease. Br J Haematol. May 1995;90(1):195-203.

Conway et al., Prognostic value of plasma von Willebrand factor and soluble P-selectin as indices of endothelial damage and platelet activation in 994 patients with nonvalvular atrial fibrillation. Circulation. Jul. 1, 2003;107(25):3141-5. Epub Jun. 9, 2003.

Cortez-Retamozo et al., Efficient tumor targeting by single-domain antibody fragments of camels. Int J Cancer. Mar. 20, 2002;98(3):456-62.

Cruz et al., Mapping the glycoprotein Ib-binding site in the von Willebrand factor A1 domain. J Biol Chem. Jun. 23, 2000;275(25):19098-105.

D'Haens et al., Endoscopic and histological healing with infliximab anti-tumor necrosis factor antibodies in Crohn's disease: A European multicenter trial. Gastroenterology. May 1999;116(5):1029-34.

De Mast et al., Thrombocytopenia and release of activated von Willebrand Factor during early Plasmodium falciparum malaria. J Infect Dis. Aug. 15, 2007;196(4):622-8. Epub Jul. 10, 2007.

Deffar et al., Nanobodies—the new concept in antibody engineering. Afr J Biotechnol. Jun. 17, 2009;8(12):2645-52.

Dong et al., Novel gain-of-function mutations of platelet glycoprotein IBalpha by valine mutagenesis in the Cys209-Cys248 disulfide loop. Functional analysis under statis and dynamic conditions. J Biol Chem. Sep. 8, 2000;275(36):27663-70.

Dong et al., Tyrosine sulfation of glycoprotein I(b)alpha. Role of electrostatic interactions in von Willebrand factor binding. J Biol Chem. May 18, 2001;276(20):16690-4. Epub Feb. 23, 2001.

Els-Conrath et al., Camel single-domain antibodies as modular building units in bispecific and bivalent antibody constructs. J Biol Chem. Mar. 9, 2001;276(10):7346-50. Epub Oct. 25, 2000.

Emsley et al., Crystal structure of the von Willebrand Factor A1 domain and implications for the binding of platelet glycoprotein Ib. J Biol Chem. Apr. 24, 1998;273(17):10396-401.

Eto et al., AJvW-2, an anti-vWF monoclonal antibody, inhibits enhanced platelet aggregation induced by high shear stress in platelet-rich plasma from patients with acute coronary syndromes. Arterioscler Thromb Vasc Biol. Apr. 1999;19(4):877-82.

Ewert et al., Biophysical properties of camelid V(HH) domains compared to those of human V(H)3 domains. Biochemistry. Mar. 19, 2002;41(11):3628-36.

Favaloro et al., Development of a simple collagen based ELISA assay aids in the diagnosis of, and permits sensitive discrimination between type I and type II, von Willebrand's disease. Blood Coagul Fibrinolysis. Apr. 1991;2(2):285-91.

Favaloro et al., Discrimination of von Willebrands disease (VWD) subtypes: direct comparison of von Willebrand factor:collagen binding assay (VWF:CBA) with monoclonal antibody (MAB) based VWF-capture systems. Thromb Haemost. Oct. 2000;84(4):541-7.

Favaloro, Detection of von Willebrand disorder and identification of qualitative von Willebrand factor defects. Direct comparison of commercial ELISA-based von Willebrand factor activity options. Am J Clin Pathol. Oct. 2000;114(4):608-18.

Fay et al., Platelets inhibit fibrinolysis in vitro by both plasminogen activator inhibitor-1-dependent and -independent mechanisms. Blood. Jan. 15, 1994;83(2):351-6.

Franchini et al., Von Willebrand factor and thrombosis. Ann Hematol. Jul. 2006;85(7):415-23. Epub Mar. 28, 2006. Review.

Fujimura et al., The interaction of botrocetin with normal or variant von Willebrand factor (types IIA and IIB) and its inhibition by monoclonal antibodies that block receptor binding. Thromb Haemost. Oct. 5, 1992;68(4):464-9.

Gibson et al., Combination therapy with abciximab reduces angiographically evident thrombus in acute myocardial infarction: a TIMI 14 substudy. Circulation. May 29, 2001;103(21):2550-4.

Goto et al., Characterization of the unique mechanism mediating the shear-dependent binding of soluble von Willebrand factor to platelets. J Biol Chem. Oct. 6, 1995;270(40):23352-61.

Groot et al., The active conformation of von Willebrand factor in patients with thrombotic thrombocytopenic purpura in remission. J Thromb Haemost. Jun. 2009;7(6):962-9.

Groot et al., The presence of active von Willebrand factor under various pathological conditions. Curr Opin Hematol. May 2007;14(3):284-9. Review.

Hill et al., Time is brain: post-marketing experience with alteplase (tpa) for acute ischemic stroke. Today's Therapeutic Trends. Jan. 1, 2000;18(4):285-304.

Holliger et al., Retargeting serum immunoglobulin with bispecific diabodies. Nat Biotechnol. Jul. 1997;15(7):632-6.

Holz, The TITAN trial—assessing the efficacy and safety of an anti-von Willebrand factor Nanobody in patients with acquired thrombotic thrombocytopenic purpura. Transfus Apher Sci. Jun. 2012;46(3):343-6. doi: 10.1016/j.transci.2012.03.027. Epub Apr. 3, 2012.

Hoogenboom et al., Mix and match: building manifold binding sites. Nat Biotechnol. Feb. 1997;15(2):125-6.

Horwitz et al., Bleeding Due to Glycoprotein IIb/IIIa Receptor Inhibition During Percutaneous Coronary Intervention: Risk Factors and Management. Cardiovasc. Rev. Rep. 2004;25(6). 12 pages. Last accessed at http://www.medscape.com/viewarticle/496983_print on Jul. 31, 2014.

Huizinga et al., Structures of glycoprotein Ibalpha and its complex with von Willebrand factor A1 domain. Science. Aug. 16, 2002;297(5584):1176-9.

Hulstein et al., A novel nanobody that detects the gain-of-function phenotype of von Willebrand factor in ADAMTS13 deficiency and von Willebrand disease type 2B. Blood. Nov. 1, 2005;106(9):3035-42. Epub Jul. 12, 2005.

Ikeda et al., The role of von Willebrand factor and fibrinogen in platelet aggregation under varying shear stress. J Clin Invest. Apr. 1991;87(4):1234-40.

(56) References Cited

OTHER PUBLICATIONS

Ill et al., Design and construction of a hybrid immunoglobulin domain with properties of both heavy and light chain variable regions. Protein Eng. Aug. 1997;10(8):949-57.
Jacobs et al., "Preclinical safety assessment of a new antithrombotic drug, the nanobody® ALX-0681." Ablynx Presentation. Feb. 18, 2010. Abstract 1577. SOT Poster 309.
Janeway et al., Ch. 3: Structure of the antibody molecule and immunoglobulin genes. In Immunobiology: The immune system in health and disease, 3rd Ed. Current Biology, Ltd, 1997;3:1-3:11.
Jauch et al., Ischemic Stroke. Medscape. May 27, 2014. 1-12.
Jones et al., Replacing the complementarity-determining regions in a human antibody with those from a mouse. Nature. May 29-Jun. 4, 1986;321(6069):522-5.
Kageyama et al., Anti-human von Willebrand factor monoclonal antibody AJvW-2 prevents thrombus deposition and neointima formation after balloon injury in guinea pigs. Arterioscler Thromb Vasc Biol. Oct. 2000;20(10):2303-8.
Kageyama et al., Anti-human vWF monoclonal antibody, AJvW-2 Fab, inhibits repetitive coronary artery thrombosis without bleeding time prolongation in dogs. Thromb Res. Mar. 1, 2001;101(5):395-404.
Kageyama et al., Anti-thrombotic effects and bleeding risk of AJvW-2, a monoclonal antibody against human von Willebrand factor. Br J Pharmacol. Sep. 1997;122(1):165-71.
Kageyama et al., Effect of a humanized monoclonal antibody to von Willebrand factor in a canine model of coronary arterial thrombosis. Eur J Pharmacol. May 17, 2002;443(1-3):143-9.
Kageyama et al., Pharmacokinetics and pharmacodynamics of AJW200, a humanized monoclonal antibody to von Willebrand factor, in monkeys. Arterioscler Thromb Vasc Biol. Jan. 2002;22(1):187-92.
Kleinschnitz et al., Targeting platelets in acute experimental stroke: impact of glycoprotein Ib, VI, and IIb/IIIa blockade on infarct size, functional outcome, and intracranial bleeding. Circulation. May 1, 2007;115(17):2323-30. Epub Apr. 16, 2007.
Lattuada et al., Mild to moderate reduction of a von Willebrand factor cleaving protease (ADAMTS-13) in pregnant women with HELLP microangiopathic syndrome. Haematologica. Sep. 2003;88(9):1029-34.
López et al., Bernard-Soulier syndrome. Blood. Jun. 15, 1998;91(12):4397-418. Review. No abstract available.
Mallender et al., Construction, expression, and activity of a bivalent bispecific single-chain antibody. J Biol Chem. Jan. 7, 1994;269(1):199-206.
Matsushita et al., Identification of amino acid residues essential for von Willebrand factor binding to platelet glycoprotein Ib. Charged-to-alanine scanning mutagenesis of the A1 domain of human von Willebrand factor. J Biol Chem. Jun. 2, 1995;270(22):13046-14.
Matsushita et al., Localization of von Willebrand factor-binding sites for platelet glycoprotein Ib and botrocetin by charged-to-alanine scanning mutagenesis. J Biol Chem. Apr. 14, 2000;275(15):11044-9.
Meyer et al, Percutaneous transluminal coronary angioplasty in patients with stable and unstable angina pectoris: analysis of early and late results. Am Heart J. Nov. 1983;106(5 Pt 1):973-80.
Miller et al.., Mutation in the gene encoding the alpha chain of platelet glycoprotein Ib in platelet-type von Willebrand disease. Proc Natl Acad Sci U S A. Jun. 1, 1991;88(11):4761-5.
Momi et al., Reperfusion of cerebral artery thrombosis by the GPIb-VWF blockade with the Nanobody ALX-0081 reduces brain infarct size in guinea pigs. Blood. Jun. 20, 2013;121(25):5088-97. doi: 10.1182/blood-2012-11-464545. Epub Apr. 15, 2013.
Murdock et al., von Willebrand factor activity detected in a monoclonal antibody-based ELISA: an alternative to the ristocetin cofactor platelet agglutination assay for diagnostic use. Thromb Haemost. Oct. 1997;78(4):1272-7.
Muyldermans et al., Single domain camel antibodies: current status. J Biotechnol. Jun. 2001;74(4):277-302. Review.
Neri et al., High-affinity antigen binding by chelating recombinant antibodies (CRAbs). J Mol Biol. Feb. 24, 1995;246(3):367-73.
Nokes et al., Von Willebrand factor has more than one binding site for platelets. Thromb Res. Jun. 1, 1984;34(5):361-6.
Ohno et al., Antigen-binding specificities of antibodies are primarily determined by seven residues of VH. Proc Natl Acad Sci U S A. May 1985;82(9):2945-9.
Patton, Breathing life into protein drugs. Nat Biotechnol. Feb. 1998;16(2):141-3.
Poletti et al., Prevention of arterial thrombosis using a novel heparin with enhanced antiplatelet activity and reduced anticoagulant activity. J Vasc Surg. Sep. 1997;26(3):366-72.
Price et al., Tissue factor and tissue factor pathway inhibitor. Anaesthesia. May 2004;59(5):493-92.
Riechmann et al., Single domain antibodies: comparison of camel VH and camelised human VH domains. J Immunol Methods. Dec. 10, 1999;231(1-2):25-38.
Rossenu et al., Population pharmacokinetic/pharmacodynamic modeling of a new antithrombotic drug, the Nanobody® ALX-0081. Population Approach Group in Europe presentation Jun. 2011. 1 page.
Rote et al., Antithrombotic effects of DMP 728, a platelet GPIIb/IIIa receptor antagonist, in a canine model of arterial thrombosis. J Cardiovasc Pharmacol. Apr. 1994;23(4):681-9.
Rudikoff et al., Single amino acid substitution altering antigen-binding specificity. Proc Natl Acad Sci U S A. Mar. 1982;79(6):1979-83.
Ruggeri, Von Willebrand factor, platelets and endothelial cell interactions. J Thromb Haemost. Jul. 2003;1(7):1335-42. Review.
Russell et al., Pseudo-von Willebrand disease: a mutation in the platelet glycoprotein Ib alpha gene associated with a hyperactive surface receptor. Blood. Apr. 1, 1993;81(7):1787-91.
Sadler et al., Molecular mechanism and classification of von Willebrand disease. Thromb Haemost. Jul. 1995;74(1):161-6. Review.
Sadler, Biochemistry and genetics of von Willebrand factor. Annu Rev Biochem. 1998;67:395-424. Review.
Savage et al., Initiation of platelet adhesion by arrest onto fibrinogen or translocation on von Willebrand factor. Cell. Jan. 26, 1996;84(2):289-97.
Silence et al., ALX-0081 Nanobody™, an Engineered Bivalent Anti-Thrombotic Drug Candidate with Improved Efficacy and Safety as Compared to the Marketed Drugs. Blood. ASH Annual Meeting Abstracts. Nov. 1, 2006; 108(11):269A. Abstract 896.
Smith et al., Prolonged in vivo residence times of antibody fragments associated with albumin. Bioconjug Chem. Sep.-Oct. 2001;12(5):750-6.
Tait et al., Phenotype changes resulting in high-affinity binding of von Willebrand factor to recombinant glycoprotein Ib-IX: analysis of the platelet-type von Willebrand disease mutations. Blood. Sep. 15, 2001;98(6):1812-8.
Tanha et al., Selection by phage display of llama conventional V(H) fragments with heavy chain antibody V(H)H properties. J Immunol Methods. May 1, 2002;263(1-2):97-109.
Thompson et al., Advances in the pathogenesis and treatment of acute coronary syndromes. J La State Med Soc. May 1999;151(5):272-7. Review. Abstract only.
Tran et al., Oral antiplatelet therapy in cerebrovascular disease, coronary artery disease, and peripheral arterial disease. JAMA. Oct. 20, 2004;292(15):1867-74.
Triplett, Coagulation and bleeding disorders: review and update. Clin Chem. Aug. 2000;46(8 Pt 2):1260-9. Review.
Tsai et al., Antibodies to von Willebrand factor-cleaving protease in acute thrombotic thrombocytopenic purpura. N Engl J Med. Nov. 26, 1998;339(22):1585-94.
Ulrichts et al., Antithrombotic drug candidate ALX-0081 shows superior preclinical efficacy and safety compared with currently marketed antiplatelet drugs. Blood. Jul. 21, 2011;118(3):757-65. doi: 10.1182/blood-2010-11-317859. Epub May 16, 2011.
Valle et al., Infliximab. Expert Opin Pharmacother. Jun. 2001;2(6):1015-25. Review.
Vanhoorelbeke et al., A reliable and reproducible Elisa method to measure ristocetin cofactor activity of von Willebrand factor. Thromb Haemost. Jan. 2000;83(1):107-13.
Varga-Szabo et al., Cell adhesion mechanisms in platelets. Arterioscler Thromb Vasc Biol. Mar. 2008;28(3):403-12. Epub Jan. 3, 2008.

(56) References Cited

OTHER PUBLICATIONS

Vasudevan et al., Modeling and functional analysis of the interaction between von Willebrand factor A1 domain and glycoprotein Ibalpha. J Biol Chem. Apr. 28, 2000;275(17):12763-8.
Vercruysse. "RIPA and RICO predicting efficacy of anti-vWF mediated thrombosis, a Phase I analysis." Ablynx Presentation. Biomarker Congress (Manchester): Feb. 25, 2010. Slides 1-52.
Veyradier, Von Willebrand Factor—A New Target for TTP Treatment? N Engl J Med. Feb. 11, 2016;374(6):583-5. doi: 10.1056/NEJMe1515876.
Veyradier et al., Laboratory diagnosis of von Willebrand disease. Int J Clin Lab Res. 1998;28(4):201-10. Review.
Vincke et al., General strategy to humanize a camelid single-domain antibody and identification of a universal humanized nanobody scaffold. J. Biol. Chem. 2009;284:3273-3284.
Vu et al., Comparison of llama VH sequences from conventional and heavy chain antibodies. Mol Immunol. Nov.-Dec. 1997;34(16-17):1121-31.
Wang et al., Aspirin and clopidogrel resistance: an emerging clinical entity. Eur Heart J. Mar. 2006;27(6):647-54. Epub Dec. 19, 2005.
Wu et al., Inhibition of the von Willebrand (VWF)-collagen interaction by an antihuman VWF monoclonal antibody results in abolition of in vivo arterial platelet thrombus formation in baboons. Blood. May 15, 2002;99(10):3623-8.
Yamamoto et al., Adjuvant effect of antibodies against von Willebrand Factor, fibrinogen, and fibronectin on staphylokinase-induced thrombolysis as measured using mural thrombi formed in rat mesenteric venules. Thromb Res. Mar. 1, 2001;97(5):327-33.
Yamamoto et al., Antagonism of vWF inhibits both injury induced arterial and venous thrombosis in the hamster. Thromb Haemost. Jan. 1998;79(1):202-10.
Yamashita et al., Contribution of von Willebrand factor to thrombus formation on neointima of rabbit stenotic iliac artery under high blood-flow velocity. Arterioscler Thromb Vasc Biol. Jun. 1, 2003;23(6):1105-10. Epub May 15, 2003.
Yamashita et al., Increased vascular wall thrombogenicity combined with reduced blood flow promotes occlusive thrombus formation in rabbit femoral artery. Arterioscler Thromb Vasc Biol. Dec. 2004;24(12):2420-4. Epub Oct. 14, 2004.
Yasuda et al., Lysis of plasminogen activator-resistant platelet-rich coronary artery thrombus with combined bolus injection of recombinant tissue-type plasminogen activator and antiplatelet GPIIb/IIIa antibody. J Am Coll Cardiol. Dec. 1990;16(7):1728-35.
Zhao et al., von Willebrand factor-cleaving protease ADAMTS13 reduces ischemic brain injury in experimental stroke. Blood. Oct. 8, 2009;114(15):3329-34. Epub Aug. 17, 2009.
Zhu et al., Plasminogen activator inhibitor-1 is a major determinant of arterial thrombolysis resistance. Circulation. Jun. 15, 1999;99(23):3050-5.
EP11162977.0, Oct. 27, 2011, Extended European Search Report.
PCT/NL03/00564, Oct. 27, 2003, International Search Report.
PCT/NL03/00564, May 28, 2004, International Preliminary Examination Report.
PCT/BE2004/000004, Jul. 19, 2004, International Search Report.
PCT/BE2004/00000, Dec. 22, 2004, International Preliminary Report on Patentability.
PCT/EP2006/00273, Jul. 25, 2005, International Search Report and Written Opinion.
PCT/EP2006/00273, Feb. 5, 2007, International Prelimary Report on Patentability.
PCT/EP2006/004773, Aug. 21, 2007, International Search Report and Written Opinion.
PCT/EP2006/004773, Nov. 23, 2007, International Preliminary Report on Patentability.
PCT/EP2007/061466, May 8, 2008, International Search Report.
PCT/EP2009/053385, Feb. 17, 2010, International Search Report and Written Opinon.
PCT/EP2009/053385, Sep. 30, 2010, International Preliminary Report on Patentability.
PCT/EP2010/068208, Feb. 16, 2011, International Search Report and Written Opinion.
PCT/EP2010/068208, Jun. 14, 2012, International Preliminary Report on Patentability.

\* cited by examiner

Figure 6

```
       HindIII
  1    aagcttgcat gcaaattcta tttcaaggag acagtcataa tgaaatacct attgcctacg gcagccgctg gattgttatt
                                                    M  K  Y   L  L  P  T   A  A  A  G  L  L  L
                                                    <                              pelB-leader SfiI  NcoI            NotI                       PstI
  81   actcgcggcc cagccggcca tggggcctaa taggcggccg cacaggtgca gctgcaggag tcataatgag ggacccaggt
        L  A  A  Q  P  A  M  G  P  -  -  A  A   A  Q  V  Q  L  Q  E  S  -  -  G  T  Q  V
                  Leader        ><     VHH#1  >   <                                    VHH#2

BstEII
 161   caccgtctcc tcagaacaaa aactcatctc agaagaggat ctgaatgggg ccgcacatca tcatcatcat cattaatgag
        T  V  S   S  E  Q   K  L  I   S  E  E  D   L  N  G   A  A  H   H  H  H  H   -  -
                 ><      C-MYC                               >    <      His6              >

EcoRI
 241   aattcactgg ccg
```

Figure 7

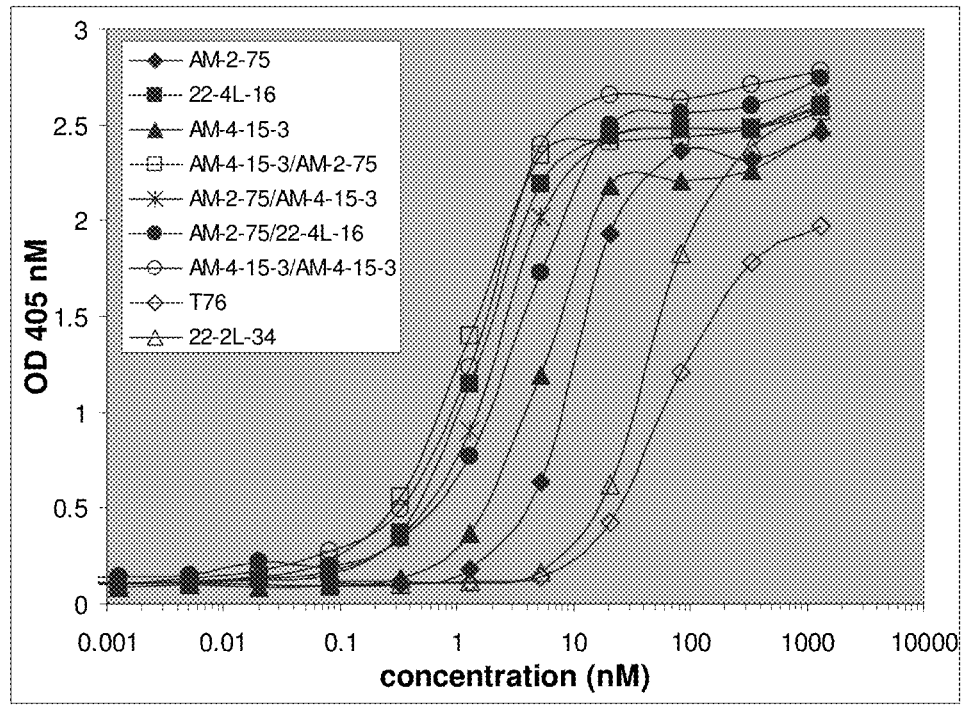

1= pig plasma
2= human plasma
3= rat plasma
4= mouse plasma
5= rabbit plasma
6= hamster plasma
7= baboon plasma 1= pig plasma
2= human plasma
3= rat plasma
4= mouse plasma
5= rabbit plasma
6= hamster plasma
7= baboon plasma

```
DP-47   EVQLLESGGGLVQPGGSLRLSCAASGFTFS SYAMS WVRQAPGKGLEWVS
AISGSGGSTYY
C-37    QVQLQESGGGLVQPGGSLRLSCAASGFNFN WYPMS WVRQAPGKGLEWVS
TISTYGEPRY-

DP-47   ADSVKG RFTISRDNSKNTLYLQMNSLRAEDTAVYYCAK --------------- --------

C-37    ADSVKG RFTISRDNANNTLYLQMNSLRPEDTAVYYCAR GAGTSSYLPQRGN
WDQGTQVTISS
```

POLYPEPTIDES AND POLYPEPTIDE CONSTRUCTS COMPRISING SINGLE DOMAIN ANTIBODIES DIRECTED AGAINST VON WILLEBRAND FACTOR

RELATED APPLICATIONS

This application is a divisional of U.S. application Ser. No. 14/669,025, filed Mar. 26, 2015, which is a continuation of U.S. application Ser. No. 10/541,708, filed Feb. 23, 2011 and issued as U.S. Pat. No. 9,028,816, which is a national stage filing under 35 U.S.C. § 371 of international application PCT/BE2004/000002, filed Jan. 9, 2004, which was published under PCT Article 21(2) in English, which is a continuation-in-part of international application PCT/EP03/06581, filed Jun. 23, 2003, a continuation-in-part of international application PCT/EP03/07313, filed Jul. 8, 2003, a continuation-in-part of international application PCT/BE03/00193, filed Nov. 7, 2003, a continuation-in-part of international application PCT/BE03/00189, filed Nov. 7, 2003, a continuation-in-part of international application PCT/BE03/00190, filed Nov. 7, 2003, a continuation-in-part of international application PCT/BE03/00192, filed Nov. 7, 2003, a continuation-in-part of international application PCT/BE03/00194, filed Nov. 7, 2003, a continuation-in-part of international application PCT/BE03/00206, filed Dec. 1, 2003, a continuation-in-part of and international application PCT/BE03/00191, filed Dec. 2, 2003, the contents of each of which is incorporated herein by reference in its entirety.

BACKGROUND TO THE INVENTION

Upon damage to a blood vessel, subendothelial structures are exposed that mediate platelet adhesion through interaction with von Willebrand factor (vWF). vWF forms a bridge between collagen within the damaged vessel wall and the platelet receptor glycoprotein Ib (gpIb), an interaction especially important under high shear conditions, leading to the formation of a haemostatic plug and thus preventing excessive bleeding (Bennett S, Thromb Haemost (2001) March; 85(3):395-400). During normal haemostasis, these processes lead to wound healing of the damaged blood vessel wall. In pathological conditions however, excessive platelet function may lead to thrombus formation. The vWF subunit is composed of several homologues domains each covering different functions. vWF interacts through its A3 domain with fibrillar collagen fibers and through its A1 domain with the platelet receptor gpIb. Under normal conditions platelets and vWF do not interact. However, when vWF is bound to collagen at high shear rate, it is believed to undergo a conformational change allowing its binding with the platelet receptor gpIb. This reversible adhesion allows platelets to roll over the damaged area, which is then followed by a firm adhesion through the collagen receptors on the platelets (gpIa/IIa, gpVI, gpIV, p65, TIIICBP) resulting in platelet activation. This leads to activation of the gpIIb/IIIa receptor, fibrinogen binding, and finally to platelet aggregation.

Platelet aggregation inhibitors have been isolated from blood sucking organisms such as leech. Saratin, derived from leech *Hirudo medicinalis* is described in WO 02/15919 A2 and in Cruz C P et al ref. Saratin, an inhibitor of von Willebrand factor-dependent platelet adhesion, decreases platelet aggregation and intimal hyperplasia in a rat carotid endarterectomy model. Journal of Vascular Surgery, 2001; 34: 724-729 and in Smith T P et al, Saratin, an inhibitor of collagen-platelet interaction, decreases venous anastomotic intimal hyperplasia in a canine dialysis access model, Vasc Endovascular Surg. 2003 July-August; 37(4):259-69.

Antibody-based therapeutics have been developed, some of which are currently used in therapy.

Abciximab (Chimeric 7E3 Fab; ReoPro; U.S. Pat. No. 6,071,514, EP 0 882 453), the Fab fragment of the mouse human chimeric antibody 7E3 which inhibits ligand binding to the platelet gpIIb/IIIa receptor, was approved for human use as adjunctive therapy to prevent ischemic complications of percutaneous coronary interventions in December 1994. The principle safety issue with gp IIb/IIIa inhibitors is the risk of bleeding, as the potent anti-platelet effect of these drugs may adversely affect haemostasis.

A murine monoclonal antibody was developed against vWF A1 domain (US 2002/0028204 A1; U.S. Pat. No. 6,280,731 and in WO 00/10601) and against its active conformation (U.S. Pat. No. 6,251,393). The in vivo efficacy is described in Kageyama S, et al: "Effect of a humanized monoclonal antibody to von Willebrand factor in a canine model of coronary arterial thrombosis", *Eur J Pharmacol.* 2002 May 17; 443(1-3): 143-9, and in "Anti-human vWF monoclonal antibody, AJvW-2 Fab, inhibits repetitive coronary artery thrombosis without bleeding time prolongation in dogs". *Thromb Res.*, 2001 Mar. 1; 101(5):395-404. and in "Anti-human von willebrand factor monoclonal antibody AJvW-2 prevents thrombus deposition and neointima formation after balloon injury in guinea pigs". *Arterioscler Thromb Vasc Biol.* 2000 October; 20(10):2303-8). AJvW-2 inhibited high shear stress induced aggregation of human platelets and had no effect on low shear stress induced platelet aggregation.

The effects in baboons of a murine antibody 82D6A3 raised against the A3 domain of human vWF, are disclosed in WO 02/051351, and Dongmei Wu et al, "Inhibition of the von Willebrand (VWF)-collagen interaction by an antihuman VWF monoclonal antibody results in abolition of in vivo arterial platelet thrombus formation in baboons". *Hemostasis, thrombosis and vascular biology*, 2002, 99: 3623-3628.

Antibody 6B4 is a monoclonal antibody (MoAb) raised against purified human gpIb. MoAb 6B4 inhibits both ristocetin- and botrocetin-induced, vWF-dependent human platelet agglutination. MoAb 6B4 furthermore blocks shear-induced adhesion of human platelets to collagen I. When injected into baboons, intact IgG and its F(ab')(2) fragments caused almost immediate thrombocytopenia, due to the bivalency of F(ab')(2) which mediates platelet crosslinking, or Fc:Fc receptor interactions which mediate activation of platelet aggregation (WO 0110911; Cauwenberghs N. et al, *Arteriosclerosis, Thrombosis and Vascular biology*, 2000, 20: 1347 and see, for example, Cadroy Y et al, Blood, 1994, 83: 3218-3224, Becker B H et al, *Blood,* 1989, 74: 690-694, Ravanat C. et al, *Thromb. Haemost.* 1999, 82: 528a abstract). Platelet deposition onto collagen-rich bovine pericardium was inhibited when Fab fragments were injected into the baboons before a thrombus was generated. However, when the Fab fragments were injected after a thrombus was allowed to form, no inhibition of further thrombosis was observed. The yields of expression of said Fab molecules are very low and the method of production is very labour intensive.

THE AIMS OF THE PRESENT INVENTION

An aim of the present invention is to provide polypeptides comprising one or more single domain antibodies directed towards vWF, vWF A1 domain, A1 domain of activated vWF, vWF A3 domain, gpIb and/or collagen, homologues of said polypeptides, and/or functional portions of said polypeptides, for the treatment for conditions which require a modulation of platelet-mediated aggregation and which overcomes the problems of the prior art. It is a further aim to provide methods of production of said polypeptides, methods to coat devices with such polypeptides used in medical procedures (e.g. PCTA, stenting), methods and kits for screening for agents that modulate platelet-mediated aggregation and kits for the diagnosis of diseases related to platelet-mediated aggregation

SUMMARY OF THE INVENTION

Single domain antibodies have been made which specifically recognize target molecules involved in the first and subsequent steps of platelet aggregation. This results in anti-thrombotic agents which are more efficacious and safer.

One embodiment of the present invention is a polypeptide construct comprising:
at least one single domain antibody directed against any of vWF, vWF A1 domain, A1 domain of activated vWF, vWF A3 domain, gpIb, or collagen.

Another embodiment of the present invention is a polypeptide construct as described above, wherein the single domain antibody directed against the A1 domain of activated vWF specifically recognizes the activated vWF conformation at the site of thrombus formation but does not bind to circulating unactivated forms of vWF.

Another embodiment of the present invention is a polypeptide construct as described above, further comprising at least one single domain antibody directed against one or more serum proteins.

Another embodiment of the present invention is a polypeptide construct as described above wherein said at least one serum protein is any of serum albumin, serum immunoglobulins, thyroxine-binding protein, transferring, or fibrinogen or a fragment thereof.

Another embodiment of the present invention is a polypeptide construct as described above, wherein at least one single domain antibody directed against one or more serum proteins corresponds to a sequence represented by any of SEQ ID NO: 16 to 19 and 49 to 61.

Another embodiment of the present invention is a polypeptide construct as described above corresponding to a sequence represented by any of SEQ ID NOs: 13 to 15 and 42 to 45.

Another embodiment of the present invention is a polypeptide construct as described above wherein at least one single domain antibody is a humanised sequence.

Another embodiment of the present invention is a polypeptide construct as described above wherein at least one single domain antibody corresponds to a sequence represented by any of SEQ ID NOs: 38 to 41 and 42 to 45

Another embodiment of the present invention is a polypeptide construct as described above corresponding to a sequence represented by any of SEQ ID NOs: 8 to 12, 20 to 22, 32 to 34, and 42 to 47.

Another embodiment of the present invention is a polypeptide construct as described above wherein at least one single domain antibody is a Camelidae VHH antibody.

Another embodiment of the present invention is a polypeptide construct as described above wherein at least one single domain antibody corresponds to a sequence represented by any of SEQ ID NOs: 1 to 7, 23 to 31, 35 to 37 and 62 to 65.

Another embodiment of the present invention is a polypeptide construct as described above, wherein said single domain antibody is an homologous sequence, a functional portion, or a functional portion of an homologous sequence of the full length single domain antibody.

Another embodiment of the present invention is a polypeptide construct as described above, wherein said polypeptide construct is a homologous sequence of said polypeptide construct, a functional portion thereof, of an homologous sequence of a functional portion thereof.

Another embodiment of the present invention is a nucleic acid encoding a polypeptide construct as described above.

Another embodiment of the present invention is a composition comprising a polypeptide construct as described above and at least one thrombolytic agent, for simultaneous, separate or sequential administration to a subject.

Another embodiment of the present invention is a composition as described above wherein said thrombolytic agent is any of staphylokinase, tissue plasminogen activator, streptokinase, single chain streptokinase, urokinase and acyl plasminogen streptokinase complex.

Another embodiment of the present invention is a polypeptide construct as described above, or a nucleic acid as described above, or a composition as described above for use in the treatment, prevention and/or alleviation of disorders relating to platelet-mediate aggregation or dysfunction thereof.

Another embodiment of the present invention is a use of a polypeptide construct as described above, or a nucleic acid as described above, or a composition as described above for the preparation of a medicament for the treatment, prevention and/or alleviation of disorders relating to platelet-mediate aggregation or dysfunction thereof.

Another embodiment of the present invention is a polypeptide construct, nucleic acid or composition as described above or a use of a polypeptide construct, nucleic acid or composition as described above wherein said disorders are any arising from transient cerebral ischemic attack, unstable or stable angina, angina pectoris, cerebral infarction, myocardial infarction, peripheral arterial occlusive disease, restenosis, coronary by-pass graft, or coronary artery valve replacement and coronary interventions such angioplasty, stenting, carotid endarterectomy or atherectomy.

Another embodiment of the present invention is a polypeptide construct, nucleic acid or composition as described above or a use of a polypeptide construct, nucleic acid or composition as described above wherein said disorders are any of the formation of a non-occlusive thrombus, the formation of an occlusive thrombus, arterial thrombus formation, acute coronary occlusion, restenosis, restenosis after PCTA or stenting, thrombus formation in stenosed arteries, hyperplasia after angioplasty, atherectomy or arterial stenting, occlusive syndrome in a vascular system or lack of patency of diseased arteries.

Another embodiment of the present invention is a polypeptide construct, nucleic acid or composition as described above or a use of a polypeptide construct, nucleic acid or composition as described above wherein said disorder is plaque or thrombus formation in high sheer environments.

Another embodiment of the present invention is a polypeptide construct, nucleic acid or composition as described above or a use of a polypeptide construct as described above wherein said polypeptide construct is administered intravenously, subcutaneously, orally, sublingually, topically, nasally, vaginally, rectally or by inhalation.

Another embodiment of the present invention is a composition comprising a polypeptide construct as described above or a nucleic acid encoding said polypeptide construct, or a composition as described above and a pharmaceutically acceptable vehicle.

Another embodiment of the present invention is a method of producing a polypeptide as described above, comprising (a) culturing host cells comprising nucleic acid capable of encoding a polypeptide as described above under conditions allowing the expression of the polypeptide, and,
(b) recovering the produced polypeptide from the culture.

Another embodiment of the present invention is a method as described above, wherein said host cells are bacterial or yeast.

Another embodiment of the present invention is a method for treating invasive medical devices to prevent platelet-mediate aggregation around the site of invasion comprising the step of coating said device with a polypeptide construct as described above.

Another embodiment of the present invention is an invasive medical device for circumventing platelet-mediate aggregation around the site of invasion, wherein said device is coated with a polypeptide construct as described above.

Another embodiment of the present invention is a method of identifying an agent that modulates platelet-mediated aggregation comprising
(a) contacting a polypeptide construct as described above with a polypeptide corresponding to its target, or a fragment thereof, in the presence and absence of a candidate modulator under conditions permitting binding between said polypeptides, and
(b) measuring the binding between the polypeptides of step (a), wherein a decrease in binding in the presence of said candidate modulator, relative to the binding in the absence of said candidate modulator identified said candidate modulator as an agent that modulate platelet-mediated aggregation.

Another embodiment of the present invention is a kit for screening for agents that modulate platelet-mediated aggregation according to the method as described above.

Another embodiment of the present invention is an unknown agent that modulates platelet-mediated aggregation identified according to the method as described above.

Another embodiment of the present invention is a method of diagnosing a disease or disorder characterised by dysfunction of platelet-mediated aggregation comprising the steps of:
(a) contacting a sample with a polypeptide construct as described above, and
(b) detecting binding of said polypeptide construct to said sample, and
(c) comparing the binding detected in step (b) with a standard, wherein a difference in binding relative to said sample is diagnostic of a disease or disorder characterised by dysfunction of platelet-mediated aggregation.

Another embodiment of the present invention is a kit for screening for diagnosing a disease or disorder characterised by dysfunction of platelet-mediated aggregation according to the method as described above.

Another embodiment of the present invention is a kit as described above comprising a polypeptide construct as described above.

DETAILED DESCRIPTION

The present invention relates to a polypeptide construct comprising one or more single domain antibodies each directed against a target and the finding that the construct has a modulating effect on platelet-mediated aggregation.

Targets

According to the invention, a target is any of vWF, vWF A1 domain, A1 domain of activated vWF, vWF A3 domain, gpIb or collagen. Said targets are mammalian, and are derived from species such as rabbits, goats, mice, rats, cows, calves, camels, llamas, monkeys, donkeys, guinea pigs, chickens, sheep, dogs, cats, horses, and preferably humans. The sequence of human vWF is provided in Table 30, SEQ ID NO: 48.

A target is also a fragment of vWF, vWF A1 domain, A1 domain of activated vWF, vWF A3 domain, gpIb or collagen, capable of eliciting an immune response. A target is also a fragment of vWF, vWF A1 domain, A1 domain of activated vWF, vWF A3 domain, gpIb or collagen, capable of binding to a single domain antibody raised against the 'parent' full length target.

A fragment as used herein refers to less than 100% of the sequence (e.g., 99%, 90%, 80%, 70%, 60%, 50%, 40%, 30%, 20%, 10% etc.), but comprising 5, 6, 7, 8, 9, 10, 12, 13, 14, 15, 16, 17, 18, 19, 20, 21, 22, 23, 24, 25 or more amino acids. A fragment is of sufficient length such that the interaction of interest is maintained with affinity of $1 \times 10^{-6}$ M or better.

A fragment as used herein also refers to optional insertions, deletions and substitutions of one or more amino acids which do not substantially alter the ability of the target to bind to a single domain antibody raised against the wild-type target. The number of amino acid insertions deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A single domain antibody directed against a target means single domain antibody that it is capable of binding to its target with an affinity of better than $10^{-6}$ M.

Single Domain Antibodies

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. According to one aspect of the invention, a single domain antibody as used herein is a naturally occurring single domain antibody known as heavy chain antibody devoid of light chains. Such single domain antibodies are disclosed in WO 9404678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

VHHs, according to the present invention, and as known to the skilled addressee are heavy chain variable domains derived from immunoglobulins naturally devoid of light chains such as those derived from Camelidae as described in WO9404678 (and referred to hereinafter as VHH domains or nanobodies). VHH molecules are about 10× smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in Camelids will recognize epitopes other than those recognised by antibodies generated in vitro through the use of antibody libraries or via immunisation of mammals other than Camelids (WO 9749805). As such, anti-albumin VHH's may interact in a more efficient way with serum albumin which is known to be a carrier protein. As a carrier protein some of the epitopes of serum albumin may be inaccessible by bound proteins, peptides and small chemical compounds. Since VHH's are known to bind into 'unusual' or non-conventional epitopes such as cavities (WO9749805), the affinity of such VHH's to circulating albumin may be increased.

Classes of VHH

The present invention further relates to a polypeptide construct, wherein a single domain antibody is a VHH directed to a target mentioned herein, wherein the VHH belongs to a class having human-like sequences. The class is characterised in that the VHHs carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 according to the Kabat numbering. A VHH sequence represented by SEQ ID NO: 1 and SEQ ID NO: 3 which bind to vWF, belong to this human-like class of VHH polypeptides. As such, peptides belonging to this class show a high amino acid sequence homology to human VH framework regions and said peptides might be administered to a human directly without expectation of an unwanted immune response therefrom, and without the burden of further humanisation.

Therefore, one aspect of the present invention allows for the direct administration of a polypeptide construct comprising one or more single domain antibodies corresponding to a sequence represented by any of SEQ ID NOs: 1 and 3 to a patient in need of the same.

Another human-like class of Camelidae single domain antibodies represented by SEQ ID No. 16 and 18 have been described in WO 03/035694 and contain the hydrophobic FR2 residues typically found in conventional antibodies of human origin or from other species, but compensating this loss in hydrophilicity by a number of residues such as the charged arginine residue, serine or uncharged residues such as glycine at position 103 that substitutes the conserved tryptophan residue present in VH from double-chain antibodies. As such, peptides belonging to these two classes show a high amino acid sequence homology to human VH framework regions and said peptides might be administered to a human directly without expectation of an unwanted immune response therefrom, and without the burden of further humanisation.

Any of the VHHs as used by the invention may be of the traditional class or of the classes of human-like Camelidae antibodies. Said antibodies may be directed against whole targets or a fragment thereof. These polypeptides include the full length Camelidae antibodies, namely Fc and VHH domains, chimeric versions of heavy chain Camelidae antibodies with a human Fc domain.

The one or more single domain antibodies of the polypeptide construct which are directed against a target may be of the same sequence. Alternatively they may not all have the same sequence. It is within the scope of the invention that a polypeptide construct comprises anti-target single domain antibodies which do not all share the same sequence, but which are directed against the same target, or fragment thereof, one or more antigens thereof.

It is another aspect of the invention that the polypeptide construct comprises two or more single domain antibodies, wherein any two single domain antibodies are directed against different targets i.e. against any of vWF, vWF A1 domain, A1 domain of activated vWF, vWF A3 domain, gpIb and collagen.

Another aspect of the invention is a bispecific polypeptide construct comprising a single domain antibody directed against vWF A1 domain, A1 domain of activated vWF, and another single domain antibody directed against vWF A3 domain. Said bispecific polypeptide construct inhibits the interaction between vWF and collagen, and the interaction between vWF and platelets.

According to an aspect of the present invention a polypeptide construct may comprise two or more single domain antibodies which have been joined. The single domain antibodies may be identical in sequence and directed against the same target or antigen. Depending on the number of VHHs linked, a multivalent VHH may be bivalent (2 VHHs), trivalent (3 VHHs), tetravalent (4 VHHs) or have a higher valency molecules.

The present invention also relates to the finding that a polypeptide construct as disclosed herein further comprising one or more single domain antibodies each directed against a serum protein of a subject, surprisingly has significantly prolonged half-life in the circulation of said subject compared with the half-life of the anti-target single domain antibody(ies) when not part of said construct. Furthermore, the said constructs were found to exhibit the same favourable properties of VHHs such as high stability remaining intact in mice, extreme pH resistance, high temperature stability and high target affinity.

Examples of such constructs are represented by SEQ ID No. 13 to 15, which comprise anti-vWF VHH and anti-mouse serum albumin VHH.

Therefore, another embodiment of the present invention is a polypeptide construct corresponding to a sequence represented by any of SEQ ID NOs: 13 to 15.

Other examples of such constructs are represented by SEQ ID No. 42 to 45, which comprise humanized anti-vWF VHH and anti-mouse serum albumin VHH.

Therefore, another embodiment of the present invention is a polypeptide construct corresponding to a sequence represented by any of SEQ ID NOs: 42 to 45.

The serum protein may be any suitable protein found in the serum of subject, or fragment thereof. In one aspect of the invention, the serum protein is serum albumin, serum immunoglobulins, thyroxine-binding protein, transferrin, or fibrinogen. Depending on the intended use such as the required half-life for effective treatment and/or compartimentalisation of the target antigen, the VHH-partner can be directed to one of the above serum proteins.

Examples of single domain antibodies directed against serum albumin are the sequences represented by the sequences corresponding to any of SEQ ID NOs: 16 to 19 and 49 to 61. Therefore another aspect of the invention is a polypeptide construct further comprising one or more anti-serum single domain antibodies, wherein the sequence of a anti-serum single domain antibody corresponds to any represented by SEQ ID NOs: 16 to 19 and 49 to 61.

Such constructs are able to circulate in the subject's serum for several days, reducing the frequency of treatment, the inconvenience to the subject and resulting in a decreased cost of treatment. Furthermore, it is an aspect of the invention that the half-life of the polypeptide constructs disclosed herein may be controlled by the number of anti-serum protein single domain antibodies present in the construct. A controllable half-life is desirable in several circumstances, for example, in the application of a timed dose of a therapeutic polypeptide construct.

Another embodiment of the present invention is a polypeptide construct as mentioned herein, further comprising a thrombolytic agent.

Said thrombolytic agent may be non-covalently or covalently attached to a single domain antibody via covalent or non-covalent means. Such covalent means are described below. Non-covalent means include via a protein interaction such as biotin/strepavidin, or via an immunoconjugate.

Alternatively, the thrombolytic agent may be administered simultaneous, separate or sequential in respect of a polypeptide construct of the invention.

Another aspect of the invention is a composition comprising at least one polypeptide construct as disclosed herein and at least one thrombolytic agent, for simultaneous, separate or sequential administration to a subject.

One aspect of the invention is a method for treating autoimmune disease comprising administering to an individual an effective amount of at least one polypeptide construct of the invention and at least one thrombolytic agent, simultaneously, separately or sequentially.

Another aspect of the invention is a kit containing at least one polypeptide construct of the invention and at least one thrombolytic agent for simultaneous, separate or sequential administration to a subject. It is an aspect of the invention that the kit may be used according to the invention. It is an aspect of the invention that the kit may be used to treat the diseases as cited herein.

By simultaneous administration means the polypeptide and thrombolytic agent are administered to a subject at the same time. For example, as a mixture or a composition comprising said components. Examples include, but are not limited to a solution administered intraveneously, a tablet, liquid, topical cream, etc., wherein each preparation comprises the components of interest.

By separate administration means polypeptide and thrombolytic agent are administered to a subject at the same time or substantially the same time. The components are present in the kit as separate, unmixed preparations. For example, the polypeptide and thrombolytic agent may be present in the kit as individual tablets. The tablets may be administered to the subject by swallowing both tablets at the same time, or one tablet directly following the other.

By sequential administration means the polypeptide and thrombolytic agent are administered to a subject sequentially. The polypeptide and thrombolytic agent are present in the kit as separate, unmixed preparations. There is a time interval between doses. For example, one component might be administered up to 336, 312, 288, 264, 240, 216, 192, 168, 144, 120, 96, 72, 48, 24, 20, 16, 12, 8, 4, 2, 1, or 0.5 hours after the other component.

In sequential administration, one component may be administered once, or any number of times and in various doses before and/or after administration of another component. Sequential administration may be combined with simultaneous or sequential administration.

The medical uses of the polypeptide construct described below, also apply to the composition comprising a polypeptide construct as disclosed herein and at least one polypeptide thrombolytic agent, for simultaneous, separate or sequential administration to a subject as disclosed here above.

Thrombolytic agents according to the invention may include, for example, staphylokinase, tissue plasminogen activator, streptokinase, single chain streptokinase, urokinase and acyl plasminogen streptokinase complex.

The single domain antibodies may be joined to form any of the polypeptide constructs disclosed herein comprising more than one single domain antibody using methods known in the art or any future method. For example, they may be fused by chemical cross-linking by reacting amino acid residues with an organic derivatisation agent such as described by Blattler et al, Biochemistry 24,1517-1524; EP294703. Alternatively, the single domain antibody may be fused genetically at the DNA level i.e. a polynucleotide construct formed which encodes the complete polypeptide construct comprising one or more anti-target single domain antibodies and one or more anti-serum protein single domain antibodies. A method for producing bivalent or multivalent VHH polypeptide constructs is disclosed in PCT patent application WO 96/34103. One way of joining multiple single domain antibodies is via the genetic route by linking single domain antibody coding sequences either directly or via a peptide linker. For example, the C-terminal end of the first single domain antibody may be linked to the N-terminal end of the next single domain antibody. This linking mode can be extended in order to link additional single domain antibodies for the construction and production of tri-, tetra-, etc. functional constructs.

The polypeptide constructs disclosed herein may be made by the skilled artisan according to methods known in the art or any future method. For example, VHHs may be obtained using methods known in the art such as by immunising a camel and obtaining hybridoma's therefrom, or by cloning a library of single domain antibodies using molecular biology techniques known in the art and subsequent selection by using phage display.

One aspect of the present invention relates to the finding that polypeptides represented by SEQ ID NOs: 1 to 7 as in Table 30 derived from Camelidae VHHs, bind to vWF and inhibit its interaction with collagen.

Therefore, one embodiment of the present invention is a polypeptide construct wherein at least one single domain antibody corresponds to a sequence represented by any of SEQ ID NOs: 1 to 7.

Another embodiment of the present invention is a polypeptide construct corresponding to a sequence represented by any of SEQ ID NOs: 8 to 12. Said sequences correspond to monospecific polypeptide constructs (such as in SEQ ID No. 8 and 11) or heterospecific polypeptide constructs comprising VHHs of different sequences (such as in SEQ ID No. 9, 10 and 12), both directed against vWF.

Another embodiment of the present invention a polypeptide construct comprising one or more single domain antibodies directed against vWF.

Platelet aggregation is a very complex phenomenon and in an in vivo situation, the interaction of vWF with collagen only takes place at high shear as observed in small arteries. To assess platelet aggregation under high shear, the inventors performed perfusion experiments. Example 16 represents shear data obtained with the specific vWF-A3 binders SEQ ID No. 1 to 12. This experiment is representative for the interactions that take place upon damage of the vessel wall in a small artery (for example during angioplasty).

Surprisingly, monovalent VHH's perform very well in a platelet aggregation experiment under high shear: 50% inhibition of platelet aggregation was obtained at a concentration between 0.08 and 0.3 µg/ml. In comparison, the IgG vWF-specific antibody inhibiting the interaction with collagen, 82D6A3, inhibits 50% of platelet aggregation at approximately a twenty-fold higher concentration (Vanhoorelbeke K. et al, *Journal of Biological Chemistry,* 2003, 278: 37815-37821). These results were unexpected given that the IC50 values for the monovalent VHH's are up to 7 times fold worse in ELISA then the IC50 value of the IgG of 82D6A3.

This clearly proves that the large size of said antibodies is not suited to interaction with macromolecules which are starting, or are in the process of aggregating, such as those involved in platelet-mediated aggregation. vWF forms multimers of up to 60 monomers (final multimers of up to 20 million dalton in size). Indeed, it has been shown that not all A3 domains are accessible to 82D6A3 (Dongmei W U, Blood, 2002, 99, 3623 to 3628). Furthermore the large size of conventional antibodies, would restrict tissue penetration, for example, during platelet-mediated aggregation at the site of a damaged vessel wall.

Nanobodies have a unique structure that consists of a single variable domain. VHH molecules derived from Camelidae antibodies are among the smallest intact antigen-binding domains known (approximately 15 kDa, or 10 times smaller than a conventional IgG) and hence are well suited towards delivery to dense tissues and for accessing the limited space between macromolecules participating in or starting the process of platelet mediated aggregation.

To our knowledge, this is the first time that experiments show, that the small size of a nanobody is advantagous over a large intact antibody for inhibition of interactions between such large macromolecules.

Despite the small size of nanobodies, and thus advantages for penetration, it is still surprising that such a small molecule can inhibit interactions between large polymers such as vWF (up to 60 monomers) and collagen and with such a high efficiency. It has been described that only the large multimeric forms of vWF are hemostatically active (Furlan, M., 1996, *Ann. Hematol.* 72:341-348). Binding of multimeric vWF to collagen occurs with ~100-fold higher affinity than binding of monomeric vWF fragments.

The results from the high shear experiments indicate that a lower dose may be administered to patients. Therefore, fewer side effects are expected (such as immunogenicity or bleeding problems).

The present invention also relates to the finding that the polypeptides corresponding to a sequence represented by any of SEQ ID NOs 23 to 31 from single domain llama antibodies, bind to the A1 domain of vWF.

Therefore, another embodiment of the present invention is a polypeptide construct comprising one or more single domain antibodies, wherein at least one single domain antibody corresponds to a sequence represented by any of SEQ ID NOs: 23 to 31.

Another embodiment of the present invention a polypeptide construct corresponding to a sequence represented by any of SEQ ID NOs: 32 to 34. Said sequences correspond to bivalent polypeptide constructs comprising VHHs of the same sequences, both directed against vWF A1 domain.

The inventors have performed perfusion experiment a flow chamber, to study the effect of polypeptide constructs comprising sequences represented by SEQ ID NOs: 23 to 31 upon platelet aggregation under high shear. Example 25 provides shear data obtained with the specific vWF-A1 binders SEQ ID No. 23 to 31

The present invention also relates to the finding that the polypeptides corresponding to a sequence represented by any of SEQ ID NOs 62 to 65 from single domain llama antibodies, bind selectively to the A1 domain of the active conformation of vWF (such as after being bound to collagen) rather than to freely circulating unactivated vWF. This results in antithrombotic agents that are both safer and more efficacious. As used herein, "selective binding" in reference to vWF A1 domains means that the llama antibodies have at least a tenfold and preferably a hundredfold greater affinity for the active conformation of vWF compared to the unactivated form.

Therefore, another embodiment of the present invention is a polypeptide construct comprising one or more single domain antibodies, wherein at least one single domain antibody corresponds to a sequence represented by any of SEQ ID NOs: 62 to 65.

In another embodiment of the present invention, a polypeptide construct comprises one or more single domain antibodies directed to the same target, and further comprises one or more single domain antibodies directed to the same target but to a different epitope in the same domain.

For example, the sequences represented by SEQ ID NOs: 9, 10 and 12 are heterospecific polypeptide constructs comprising VHHs directed to different epitopes in the A3 domain of vWF. Therefore, another embodiment of the present invention a polypeptide construct corresponding to a sequence represented by any of SEQ ID NOs: 9, 10 and 12.

Another embodiment of the present invention is a polypeptide construct wherein the number of single domain antibodies directed to the same target is two or more.

The sequences represented by SEQ ID NOs: 8 and 11 are polypeptide constructs comprising VHHs directed to the same epitopes in the A3 domain of vWF, wherein the both VHHs have identical sequences. Therefore, another embodiment of the present invention is a polypeptide construct corresponding to a sequence represented by any of SEQ ID NOs: 8 and 11.

In another embodiment of the present invention, a polypeptide construct comprises one or more single domain antibodies directed to one domain of the same target, and one or more single domain antibodies directed to the same target but to another domain of the same target. Examples of different domains might be the A1 and A3 domains of vWF In another example, the sequences represented by SEQ ID NOs: 20, 21 and 22 are heterospecific polypeptide constructs comprising VHHs directed to epitopes on different domains of vWF i.e. A1 and A3 of vWF. Therefore, another embodiment of the present invention is a polypeptide construct corresponding to a sequence represented by any of SEQ ID NOs: 20, 21 and 22.

It is aspect of the invention that at least one VHH directed to the A1 domain in a heterospecific polypeptide construct recognizes the active conformation of vWF. Such a VHH corresponds to a sequence represented by any of SEQ ID NOs: 62 to 65.

Such polypeptide constructs may have superior antithrombotic effects compared to the monomeric VHH's. Perfusion experiment were performed in a flow chamber, to study platelet aggregation under high shear to study the effects of these polypeptide constructs. Example 30 represents shear data obtained with the heterospecific polypeptide construct comprising anti vWF-A1 VHH and anti-vWF-A3 VHH.

The present invention also relates to the finding that the polypeptides represented by SEQ ID NOs 35 to 37 from single domain llama antibodies, bind to collagen type I and/or type III.

Therefore, another embodiment of the present invention is a polypeptide construct, wherein at least one single domain antibody corresponds to a sequence represented by any of SEQ ID NOs: 35 to 37.

In another embodiment of the present invention, a polypeptide construct comprises one or more single domain antibodies directed to the collagen I and/or type III, and one or more single domain antibodies directed to the same target but to a different epitope in the same domain. The sequences represented by 3P1-31_3P2-31 and 3L-41_3P2-31 are heterospecific polypeptide constructs comprising VHHs directed to different epitopes in collagen type I. Therefore, another embodiment of the present invention a polypeptide construct corresponding to a sequence represented by any of SEQ ID NOs: 46 and 47.

Another aspect of the invention is a polypeptide construct comprising one or more single domain antibodies directed to the platelet glycoprotein Ib.

A murine anti-human vWF monoclonal antibody, AJvW-2 (IgG), was developed that inhibited the interaction between platelet glycoprotein Ib (gpIb) and von Willebrand factor (vWF) during the ristocetin- and botrocetin-induced aggregation of human platelets (PCT application number WO 00/10601). AJvW-2 Fab, inhibits repetitive coronary artery thrombosis without bleeding time prolongation in dogs (Kageyama S et al, Thromb Res., 2001 Mar. 1; 101(5):395-404) and prevents thrombus deposition and neointima formation after balloon injury in guinea pigs (Kageyama S, et al, Arterioscler Thromb Vasc Biol. 2000 October; 20(10): 2303-8).

Antibody 6B4 is a monoclonal antibody (MoAb) raised against purified human gpIb (PCT application number WO 01/10911 A2). When injected into baboons, intact IgG and its F(ab')2 fragments caused almost immediate thrombocytopenia, due to the bivalency of F(ab')2 which mediates platelet crosslinking, or Fc:Fc receptor interactions which mediate activation of platelet aggregation (Cauwenberghs N. et al, Arteriosclerosis, Thrombosis and Vascular biology, 2000, 20: 1347 and see, for example, Cadroy Y et al, Blood, 1994, 83: 3218-3224, Becker B H et al, blood, 1989, 74: 690-694, Ravanat C. et al, Thromb. Haemost. 1999, 82: 528a abstract). Platelet deposition onto collagen-rich bovine pericardium was inhibited when Fab fragments were injected into the baboons before a thrombus was generated. However, when the Fab fragments were injected after a thrombus was allowed to form, no inhibition of further thrombosis was observed.

It was shown that the affinity of the Fab fragment for the gpIb receptor on the platelet dropped by a factor of 10 as compared to the intact IgG or F(ab')2 (KD=49.2 nM, 4.7 nM and 6.4 nM respectively). Also the IC50 value for ristocetin-induced platelet aggregation was up to 10-fold worse for Fab as compared to IgG or F(ab')2 (IC50 of 40 nM, 4.5 nM and 7.7 nM respectively).

It might be expected that the undesirable thrombocytopenia caused by Fc:Fc receptor mediated activation of platelet aggregation and/or F(ab')2-mediated crosslinking of platelets which has been observed when using intact IgG or F(ab')2 therapeutically in vivo, will be avoided by the use of VHH, since VHH contains no Fc and it is not bivalent. No loss of affinity and activity will be obtained as observed with the Fab fragment of 6B4 as nanobodies are already single domain molecules.

Humanised Antibodies

The discovery of naturally occurring single domain antibodies in llama, dromedary and camel revealed a new class of therapeutic molecules which combine the advantages of monoclonal antibodies for example specificity, low toxicity with the advantages of small molecules for example tissue penetration and stability. Unfortunately, the development of appropriate therapeutic products based on these proteins has the drawback of being Camelidae derived, and thus not human. Non-human proteins contain amino acid residues that can be immunogenic when injected into a human patient. Although studies have shown that Camelidae-derived VHH are not immunogenic when injected in mice, replacing Camelidae residues by human residues is preferable. These humanized polypeptides should be substantially non-immunogenic in humans, but retain the affinity and activity of the wild type polypeptide.

By humanised is meant mutated so that immunogenicity upon administration in human patients is minor or nonexistent. Humanising a polypeptide, according to the present invention, comprises a step of replacing one or more of the Camelidae amino acids by their human counterpart as found in the human consensus sequence, without that polypeptide losing its typical character, i.e. the humanisation does not significantly affect the antigen binding capacity of the resulting polypeptide.

The inventors have determined the amino acid residues of the antibody variable domain (VHH) which may be modified without diminishing the native affinity of the domain for antigen and while reducing its immunogenicity with respect to a heterologous species; the use of VHHs having modifications at the identified residues which are useful for administration to heterologous species; and to the VHH so modified. More specifically, the invention relates to the preparation of modified VHHs, which are modified for administration to humans, the resulting VHH themselves, and the use of such "humanized" VHHs in the treatment of diseases in humans.

The inventor have also found that humanization of VHH polypeptides requires the introduction and mutagenesis of only a limited number of amino acids in a single polypeptide chain without dramatic loss of binding and/or inhibition activity. This is in contrast to humanization of scFv, Fab, (Fab)2 and IgG, which requires the introduction of amino acid changes in two chains, the light and the heavy chain and the preservation of the assembly of both chains.

A humanisation technique may be performed by a method comprising the replacement of any of the following residues either alone or in combination: FR1 positions 1, 5, 28 and 30, the hallmark amino acid at position 37, 44, 45 and 47 in FR2, FR3 residues 74, 75, 76, 83, 84, 93 and 94 and positions 103, 104, 108 and 111 in FR4; numbering according to the Kabat numbering. Examples of such humanized sequences are given in Table 30, SEQ ID No. 2, 38 to 41.

Polypeptides represented in example 63 and 64 have a high degree of homology to human germline VH DP-47. Further humanization required the introduction and mutagenesis of a limited amount of amino acids in a single polypeptide chain. This is in contrast to humanization of scFv, Fab, (Fab)2 and IgG, which requires the introduction of amino acid changes in two chains, the light and the heavy chain and the preservation of the assembly of both chains.

The polypeptides contain human-like residues in FR2. Humanization required mutagenesis of residues in FR1 at position 1 and 5 which were introduced by the primer used for repertoire cloning and do not occur naturally in the llama sequence. Mutagenesis of those residues did not result in loss of binding and/or inhibition activity. Humanization of FR1 also required mutagenesis of position 28 and 30. Mutagenesis of those residues also did not result in loss of binding and/or inhibition activity.

Humanization also required mutagenesis of residues in FR3 at position 74, 75, 76, 83, 84, 93, 94. Mutagenesis of those residues did not result in loss of binding and/or inhibition activity.

Humanization also required mutagenesis of residues in FR4 at position 104, 108 and 111. Mutagenesis of Q108L resulted in lower production level in *Escherichia coli*. Position 108 is solvent exposed in camelid VHH, while in human antibodies this position is buried at the VH-VL interface (Spinelli, 1996; Nieba, 1997). In isolated VHs position 108 is solvent exposed. The introduction of a non-polar hydrophobic Leu instead of polar uncharged Gln can have a drastic effect on the intrinsic foldability/stability of the molecule.

One embodiment of the present invention is a method for humanizing a VHH comprising the steps of:
(a) replacing of any of the following residues either alone or in combination:
  FR1 positions 1, 5, 28 and 30,
  the hallmark amino acid at position 37, 44, 45 and 47 in FR2,
  FR3 residues 74, 75, 76, 83, 84, 93 and 94,
  and positions 103, 104, 108 and 111 in FR4;
numbering according to the Kabat numbering.

Examples of such humanized sequences are given in Table 30, SEQ ID No. 2, 38 to 41.

The use of antibodies derived from sources such as mouse, sheep, goat, rabbit etc., and humanised derivatives thereof as a treatment for conditions which require a modulation of platelet-associated aggregation, is problematic for several reasons. Traditional antibodies are not stable at room temperature, and have to be refrigerated for preparation and storage, requiring necessary refrigerated laboratory equipment, storage and transport, which contribute towards time and expense. Refrigeration is sometimes not feasible in developing countries. The yields of expression of said Fab molecules are very low and the method of production is very labor intensive. Furthermore, the manufacture or small-scale production of said antibodies is expensive because the mammalian cellular systems necessary for the expression of intact and active antibodies require high levels of support in terms of time and equipment, and yields are very low. Furthermore, traditional antibodies have a binding activity which depends upon pH, and hence are unsuitable for use in environments outside the usual physiological pH range such as, for example, in treating gastric bleeding, gastric surgery. Furthermore, traditional antibodies are unstable at low or high pH and hence are not suitable for oral administration. However, it has been demonstrated that camelid antibodies resist harsh conditions, such as extreme pH, denaturing reagents and high temperatures (Ewert S et al, Biochemistry 2002 Mar. 19; 41(11):3628-36), so making them suitable for delivery by oral administration. Furthermore, traditional antibodies have a binding activity which depends upon temperature, and hence are unsuitable for use in assays or kits performed at temperatures outside biologically active-temperature ranges (e.g. 37±20° C.).

The polypeptide constructs represented by SEQ ID NOs: 1 to 47 and 49 to 65 and their derivatives not only possess the advantageous characteristics of conventional antibodies, such as low toxicity and high selectivity, but they also exhibit additional properties. They are more soluble, meaning they may be stored and/or administered in higher concentrations compared with conventional antibodies. They are stable at room temperature meaning they may be prepared, stored and/or transported without the use of refrigeration equipment, conveying a cost, time and environmental savings (described in example 61). Other advantageous characteristics as compared to conventional antibodies include short half-life in the circulation which may be modulated according to the invention by, for example, albumin-coupling, a bispecific nanobody with one specificity against albumin and the other against the target, Fc coupling, VHH coupling (bivalent VHHs) or by pegylation (described in example 41 until 54). A short and controllable half-life is desirable for surgical procedures, for example, which require an inhibition of platelet-mediated aggregation for a limited time period. Also, when bleeding problems occur or other complications, dosage can be lowered immediately. The polypeptides of the present invention also retain binding activity at a pH and temperature outside those of usual physiological ranges, which means they may be useful in situations of extreme pH and temperature which require a modulation of platelet-mediated aggregation, such as in gastric surgery, control of gastric bleeding, assays performed at room temperature etc. The polypeptides of the present invention also exhibit a prolonged stability at extremes of pH, meaning they would be suitable for delivery by oral administration. The polypeptides of the present invention may be cost-effectively produced through fermentation in convenient recombinant host organisms such as *Escherichia coli* and yeast; unlike conventional antibodies which also require expensive mammalian cell culture facilities, achievable levels of expression are high. Examples of yields of the polypeptides of the present invention are 1 to 10 mg/ml (*E. coli*) and up to 1 g/l (yeast). The polypeptides of the present invention also exhibit high binding affinity for a broad range of different antigen types, and ability to bind to epitopes not recognised by conventional antibodies; for example they display long CDR-based loop structures with the potential to penetrate into cavities and exhibit enzyme function inhibition. Furthermore, since binding often occurs through the CDR3 loop only, it is envisaged that peptides derived from CDR3 could be used therapeutically (Desmyter et al., *J Biol Chem*, 2001, 276: 26285-90). The preparation of such peptide is described in Example 65. The polypeptides of the invention are also able to retain full binding capacity as fusion protein with an enzyme or toxin. Furthermore, it might be expected that the undesirable thrombocytopenia caused by Fc:Fc receptor mediated activation of platelet aggregation and/or F(ab')(2)-mediated crosslinking of platelets which has been observed when using intact IgG or F(ab')(2) therapeutically in vivo (see Cauwenberghs N. et al, Arteriosclerosis, Thrombosis and Vascular biology, 2000, 20: 1347), will be avoided in the use of VHH, since VHH contains no Fc and it is not bivalent. Thus the polypeptides represented by SEQ ID NOs: 1 to 15, 20 to 47, 62 to 65, homologues or functional portions thereof provide a considerable cost and time saving in the treatment and diagnosis of conditions related to platelet-mediated aggregation, and the patient in need of said polypeptides would encounter fewer of the problems associated with conventional agents.

Platelet-mediated aggregation is the process wherein vWF-bound collagen adheres to platelets and/or platelet receptors (examples of both are gpIa/IIa, gpIb, or collagen), ultimately resulting in platelet activation. Platelet activation leads to fibrinogen binding, and finally to platelet aggregation. It is within the scope of the present invention to provide polypeptides which modulate the processes which comprise platelet-mediated aggregation such as vWF-collagen binding, vWF-platelet receptor adhesion, collagen-platelet receptor adhesion, platelet activation, fibrinogen binding and/or platelet aggregation. Said polypeptides are derived from Camelidae antibodies directed towards vWF, vWF A1, A1 domain of activated vWF or A3 domains, gpIb or collagen, and share the same advantages as the polypeptides represented by SEQ ID NOs: 1 to 15, 20 to 47 and 62 to 65, as described above.

According to an aspect of the invention a polypeptide construct may be a homologous sequence of a full-length polypeptide construct. According to another aspect of the invention, a polypeptide construct may be a functional portion of a full-length polypeptide construct. According to another aspect of the invention, a polypeptide construct may be a homologous sequence of a full length polypeptide construct. According to another aspect of the invention, a polypeptide construct may be a functional portion of a homologous sequence of a full length polypeptide construct. According to an aspect of the invention a polypeptide construct may comprise a sequence of a polypeptide construct.

According to an aspect of the invention a single domain antibody used to form a polypeptide construct may be a complete single domain antibody (e.g. a VHH) or a homologous sequence thereof. According to another aspect of the invention, a single domain antibody used to form the polypeptide construct may be a functional portion of a complete single domain antibody. According to another aspect of the invention, a single domain antibody used to form the polypeptide construct may be a homologous sequence of a complete single domain antibody. According to another aspect of the invention, a single domain antibody used to form the polypeptide construct may be a functional portion of a homologous sequence of a complete single domain antibody.

Another aspect of the present invention are the single domain antibodies corresponding to any of SEQ ID NOs: 1 to 7, 16 to 19, 23 to 31, 35 to 41, and 49 to 65, a homologous sequence thereof, and/or a functional portion thereof.

According to another aspect of the invention a polypeptide construct may be an homologous sequence of the parent sequence. According to another aspect of the invention, a polypeptide construct may be a functional portion parent sequence. According to another aspect of the invention, a polypeptide construct may be a functional portion of a homologous sequence of the parent sequence.

As used herein, an homologous sequence may comprise additions, deletions or substitutions of one or more amino acids, which do not substantially alter the functional characteristics of the polypeptide. The number of amino acid deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A homologous sequence according to the present invention includes polypeptides extended by the addition of amino acids to form human heavy chain antibody or human single domain heavy chain antibody, which do not substantially alter the functional characteristics of the unmodified polypeptide.

A homologous sequence of the present invention may include a polypeptide represented by any of SEQ ID NOs: 1 to 47 and 49 to 65, which has been humanised (as described in examples 63 and 64.

A homologous sequence of the present invention may include a sequence corresponding to the sequence of any of SEQ ID NOs: 1 to 47 and 49 to 65 which exists in other Camelidae species such as, for example, camel, llama, dromedary, alpaca, guanaco etc.

Where homologous sequence indicates sequence identity, it means a sequence which presents a high sequence identity (more than 70%, 75%, 80%, 85%, 90%, 95% or 98% sequence identity) with the parent sequence, and is preferably characterised by similar properties of the parent sequence, namely affinity, said identity calculated using known methods.

Alternatively, an homologous sequence may also be any amino acid sequence resulting from allowed substitutions at any number of positions of the parent sequence according to the formula below:
Ser substituted by Ser, Thr, Gly, and Asn;
Arg substituted by one of Arg, His, Gln, Lys, and Glu;
Leu substituted by one of Leu, Ile, Phe, Tyr, Met, and Val;
Pro substituted by one of Pro, Gly, Ala, and Thr;
Thr substituted by one of Thr, Pro, Ser, Ala, Gly, His, and Gln;
Ala substituted by one of Ala, Gly, Thr, and Pro;
Val substituted by one of Val, Met, Tyr, Phe, Ile, and Leu;
Gly substituted by one of Gly, Ala, Thr, Pro, and Ser;
Ile substituted by one of Ile, Met, Tyr, Phe, Val, and Leu;
Phe substituted by one of Phe, Trp, Met, Tyr, Ile, Val, and Leu;
Tyr substituted by one of Tyr, Trp, Met, Phe, Ile, Val, and Leu;
His substituted by one of His, Glu, Lys, Gln, Thr, and Arg;
Gln substituted by one of Gln, Glu, Lys, Asn, His, Thr, and Arg;
Asn substituted by one of Asn, Glu, Asp, Gln, and Ser;
Lys substituted by one of Lys, Glu, Gln, His, and Arg;
Asp substituted by one of Asp, Glu, and Asn;
Glu substituted by one of Glu, Asp, Lys, Asn, Gln, His, and Arg;
Met substituted by one of Met, Phe, Ile, Val, Leu, and Tyr.

A homologous according to the present invention may refer to nucleotide sequences of more than 50, 100, 200, 300, 400, 500, 600, 800 or 1000 nucleotides able to hybridize to the reverse-complement of the nucleotide sequence capable of encoding a polypeptide under stringent hybridisation conditions (such as the ones described by SAMBROOK et al., Molecular Cloning, Laboratory Manuel, Cold Spring, Harbor Laboratory press, New York).

As used herein, a functional portion refers to a single domain antibody of sufficient length such that the interaction of interest is maintained with affinity of $1 \times 10^{-6}$ M or better.

Alternatively a functional portion of a single domain antibody of the invention comprises a partial deletion of the complete amino acid sequence and still maintains the binding site(s) and protein domain(s) necessary for the binding of and interaction with the target.

Alternatively a functional portion of any of SEQ ID NO: 1 to 7 is a polypeptide which comprises a partial deletion of the complete amino acid sequence and which still maintains the binding site(s) and protein domain(s) necessary for the inhibition of binding of vWF to collagen.

Alternatively a functional portion of any of SEQ ID NOs: 23 to 31 and 62 to 65 is a polypeptide which comprises a partial deletion of the complete amino acid sequence and which still maintains the binding site(s) and protein domain(s) necessary for the binding of and interaction with the A1 domain of vWF.

Alternatively a functional portion of any of SEQ ID NOs: 35 to 37 is a polypeptide which comprises a partial deletion of the complete amino acid sequence and which still maintains the binding site(s) and protein domain(s) necessary for the binding of and interaction with collagen.

Alternatively a functional portion comprises a partial deletion of the complete amino acid sequence of a polypeptide and which still maintains the binding site(s) and protein domain(s) necessary for the binding of and interaction with the antigen against which it was raised. It includes, but is not limited to VHH domains.

As used herein, a functional portion as it refers to a polypeptide sequence refers to less than 100% of the sequence (e.g., 99%, 90%, 80%, 70%, 60% 50% etc.), but comprising 5 or more amino acids.

A portion as it refers to a nucleotide sequence encoding a polypeptide sequence refers to less than 100% of the sequence (e.g., 99%, 90%, 80%, 70%, 60% 50% etc.), but comprising 15 or more nucleotides.

An aspect of the present invention is the administration of a polypeptide construct according to the invention can avoid the need for injection. Conventional antibody-based therapeutics have significant potential as drugs because they have exquisite specificity to their target and a low inherent toxicity, however, they have one important drawback: they are relatively unstable, and are sensitive to breakdown by proteases. This means that conventional antibody drugs cannot be administered orally, sublingually, topically, nasally, vaginally, rectally or by inhalation because they are not resistant to the low pH at these sites, the action of proteases at these sites and in the blood and/or because of their large size. They have to be administered by injection (intravenously, subcutaneously, etc.) to overcome some of these problems. Administration by injection requires specialist training in order to use a hypodermic syringe or needle correctly and safely. It further requires sterile equipment, a liquid formulation of the therapeutic polypeptide, vial packing of said polypeptide in a sterile and stable form and, of the subject, a suitable site for entry of the needle. Furthermore, subjects commonly experience physical and psychological stress prior to and upon receiving an injection.

An aspect of the present invention overcomes these problems of the prior art, by providing the polypeptides constructs of the present invention. Said constructs are sufficiently small, resistant and stable to be delivered orally, sublingually, topically, nasally, vaginally, rectally or by inhalation substantial without loss of activity. The polypeptides constructs of the present invention avoid the need for injections, are not only cost/time savings, but are also more convenient and more comfortable for the subject.

One embodiment of the present invention is a polypeptide construct as disclosed herein for use in treating, preventing and/or alleviating the symptoms of disorders susceptible to modulation by a substance that controls platelet mediated aggregation which is able pass through the gastric environment without the substance being inactivated.

As known by persons skilled in the art, once in possession of said polypeptide construct, formulation technology may be applied to release a maximum amount of polypeptide in the right location (in the stomach, in the colon, etc.). This method of delivery is important for treating, prevent and/or alleviate the symptoms of disorders whose targets are located in the gut system.

An aspect of the invention is a method for treating, preventing and/or alleviating the symptoms of a disorder susceptible to modulation by a substance that controls platelet mediated aggregation which is able pass through the gastric environment without being inactivated, by orally administering to a subject a polypeptide construct as disclosed herein.

Another embodiment of the present invention is a use of a polypeptide construct as disclosed herein for the preparation of a medicament for treating, preventing and/or alleviating the symptoms of disorders susceptible to modulation by a substance that controls platelet mediated aggregation which is able pass through the gastric environment without being inactivated.

An aspect of the invention is a method for delivering a substance that controls platelet mediated aggregation to the gut system without said substance being inactivated, by orally administering to a subject a polypeptide construct as disclosed herein.

An aspect of the invention is a method for delivering a substance that controls platelet mediated aggregation to the bloodstream of a subject without the substance being inactivated, by orally administering to a subject a polypeptide construct as disclosed herein.

Another embodiment of the present invention is a polypeptide construct as disclosed herein for use in treating, preventing and/or alleviating the symptoms or disorders susceptible to modulation by a substance that controls platelet mediated aggregation delivered to the vaginal and/or rectal tract.

In a non-limiting example, a formulation according to the invention comprises a polypeptide construct as disclosed herein, in the form of a gel, cream, suppository, film, or in the form of a sponge or as a vaginal ring that slowly releases the active ingredient over time (such formulations are described in EP 707473, EP 684814, U.S. Pat. No. 5,629,001).

An aspect of the invention is a method for treating, preventing and/or alleviating the symptoms of disorders susceptible to modulation by a substance that controls platelet mediated aggregation delivered to the vaginal and/or rectal tract, by vaginally and/or rectally administering to a subject a polypeptide construct as disclosed herein.

Another embodiment of the present invention is a use of a polypeptide construct as disclosed herein for the preparation of a medicament for treating, preventing and/or alleviating the symptoms of disorders susceptible to modulation by a substance that controls platelet mediated aggregation delivered to the vaginal and/or rectal tract.

An aspect of the invention is a method for delivering a substance that controls platelet mediated aggregation to the vaginal and/or rectal tract without being said substance being inactivated, by administering to the vaginal and/or rectal tract of a subject a polypeptide construct as disclosed herein.

An aspect of the invention is a method for delivering a substance that controls platelet mediated aggregation to the bloodstream of a subject without said substance being inactivated, by administering to the vaginal and/or rectal tract of a subject a polypeptide construct as disclosed herein.

Another embodiment of the present invention is a polypeptide construct as disclosed herein, for use in treating, preventing and/or alleviating the symptoms of disorders susceptible to modulation by a substance that controls platelet mediated aggregation delivered to the nose, upper respiratory tract and/or lung.

In a non-limiting example, a formulation according to the invention, comprises a polypeptide construct as disclosed herein in the form of a nasal spray (e.g. an aerosol) or inhaler. Since the polypeptide construct is small, it can reach its target much more effectively than therapeutic IgG molecules.

An aspect of the invention is a method for treating, preventing and/or alleviating the symptoms of disorders susceptible to modulation by a substance that controls platelet mediated aggregation delivered to the upper respiratory tract and lung, by administering to a subject a polypeptide construct as disclosed herein, by inhalation through the mouth or nose.

Another embodiment of the present invention is a use of a polypeptide construct as disclosed herein for the preparation of a medicament for treating, preventing and/or alleviating the symptoms of disorders susceptible to modulation by a substance that controls platelet mediated aggregation delivered to the nose, upper respiratory tract and/or lung, without said polypeptide being inactivated.

An aspect of the invention is a method for delivering a substance that controls platelet mediated aggregation to the nose, upper respiratory tract and lung without inactivation, by administering to the nose, upper respiratory tract and/or lung of a subject a polypeptide construct as disclosed herein.

An aspect of the invention is a method for delivering a substance that controls platelet mediated aggregation to the bloodstream of a subject without inactivation by administering to the nose, upper respiratory tract and/or lung of a subject a polypeptide construct as disclosed herein.

One embodiment of the present invention is a polypeptide construct as disclosed herein for use in treating, preventing and/or alleviating the symptoms of disorders susceptible to modulation by a substance that controls platelet mediated aggregation delivered to the intestinal mucosa, wherein said disorder increases the permeability of the intestinal mucosa. Because of their small size, a polypeptide construct as disclosed herein can pass through the intestinal mucosa and reach the bloodstream more efficiently in subjects suffering from disorders which cause an increase in the permeability of the intestinal mucosa.

An aspect of the invention is a method for treating, preventing and/or alleviating the symptoms of disorders susceptible to modulation by a substance that controls platelet mediated aggregation delivered to the intestinal mucosa, wherein said disorder increases the permeability of the intestinal mucosa, by orally administering to a subject a polypeptide construct as disclosed herein.

This process can be even further enhanced by an additional aspect of the present invention—the use of active transport carriers. In this aspect of the invention, VHH is fused to a carrier that enhances the transfer through the intestinal wall into the bloodstream. In a non-limiting example, this "carrier" is a second VHH which is fused to the therapeutic VHH. Such fusion constructs are made using methods known in the art. The "carrier" VHH binds specifically to a receptor on the intestinal wall which induces an active transfer through the wall.

Another embodiment of the present invention is a use of a polypeptide construct as disclosed herein for the preparation of a medicament for treating, preventing and/or alleviating the symptoms of disorders susceptible to modulation by a substance that controls platelet mediated aggregation delivered to the intestinal mucosa, wherein said disorder increases the permeability of the intestinal mucosa.

An aspect of the invention is a method for delivering a substance that controls platelet mediated aggregation to the intestinal mucosa without being inactivated, by administering orally to a subject a polypeptide construct of the invention.

An aspect of the invention is a method for delivering a substance that controls platelet mediated aggregation to the bloodstream of a subject without being inactivated, by administering orally to a subject a polypeptide construct of the invention.

This process can be even further enhanced by an additional aspect of the present invention—the use of active transport carriers. In this aspect of the invention, a polypeptide construct as described herein is fused to a carrier that enhances the transfer through the intestinal wall into the bloodstream. In a non-limiting example, this "carrier" is a VHH which is fused to said polypeptide. Such fusion constructs made using methods known in the art. The "carrier" VHH binds specifically to a receptor on the intestinal wall which induces an active transfer through the wall.

One embodiment of the present invention is a polypeptide construct as disclosed herein for use in treating, preventing and/or alleviating the symptoms of disorders susceptible to modulation by a substance that controls platelet mediated aggregation which is able pass through the tissues beneath the tongue effectively. A formulation of said polypeptide construct as disclosed herein, for example, a tablet, spray, drop is placed under the tongue and adsorbed through the mucus membranes into the capillary network under the tongue.

An aspect of the invention is a method for treating, preventing and/or alleviating the symptoms of disorders susceptible to modulation by a substance that controls platelet mediated aggregation which is able pass through the tissues beneath the tongue effectively, by sublingually administering to a subject a polypeptide construct as disclosed herein.

Another embodiment of the present invention is a use of a polypeptide construct as disclosed herein for the preparation of a medicament for treating, preventing and/or alleviating the symptoms of disorders susceptible to modulation by a substance that controls platelet mediated aggregation which is able to pass through the tissues beneath the tongue.

An aspect of the invention is a method for delivering a substance that controls platelet mediated aggregation to the tissues beneath the tongue without being inactivated, by administering sublingually to a subject a polypeptide construct as disclosed herein.

An aspect of the invention is a method for delivering a substance that controls platelet mediated aggregation to the bloodstream of a subject without being inactivated, by administering orally to a subject a polypeptide construct as disclosed herein.

One embodiment of the present invention is a polypeptide construct as disclosed herein for use in treating, preventing and/or alleviating the symptoms of disorders susceptible to modulation by a substance that controls platelet mediated aggregation which is able pass through the skin effectively. A formulation of said polypeptide construct, for example, a cream, film, spray, drop, patch, is placed on the skin and passes through.

An aspect of the invention is a method for treating, preventing and/or alleviating the symptoms of disorders susceptible to modulation by a substance that controls platelet mediated aggregation which is able pass through the skin effectively, by topically administering to a subject a polypeptide construct as disclosed herein.

Another embodiment of the present invention is a use of a polypeptide construct as disclosed herein for the preparation of a medicament for treating, preventing and/or alleviating the symptoms of disorders susceptible to modulation by a substance that controls platelet mediated aggregation which is able pass through the skin effectively.

An aspect of the invention is a method for delivering a substance that controls platelet mediated aggregation to the skin without being inactivated, by administering topically to a subject a polypeptide construct as disclosed herein.

An aspect of the invention is a method for delivering a substance that controls platelet mediated aggregation to the bloodstream of a subject, by administering topically to a subject a polypeptide construct as disclosed herein.

In another embodiment of the present invention, a polypeptide construct as disclosed herein further comprises a carrier single domain antibody (e.g. VHH) which acts as an active transport carrier for transport of said polypeptide construct via the lung lumen to the blood. A polypeptide construct further comprising a carrier that binds specifically to a receptor present on the mucosal surface (bronchial epithelial cells) resulting in the active transport of the polypeptide from the lung lumen to the blood. The carrier single domain antibody may be fused to the polypeptide construct. Such fusion constructs made using methods known in the art and are describe herein. The "carrier" single domain antibody binds specifically to a receptor on the mucosal surface which induces an active transfer through the surface.

Another aspect of the present invention is a method to determine which single domain antibodies (e.g. VHHs) are actively transported into the bloodstream upon nasal administration. Similarly, a naïve or immune VHH phage library can be administered nasally, and after different time points after administration, blood or organs can be isolated to rescue phages that have been actively transported to the bloodstream. A non-limiting example of a receptor for active transport from the lung lumen to the bloodstream is the Fc receptor N (FcRn). One aspect of the invention includes the VHH molecules identified by the method. Such VHH can then be used as a carrier VHH for the delivery of a therapeutic VHH to the corresponding target in the bloodstream upon nasal administration.

One embodiment of the present invention is a polypeptide construct as disclosed herein for use in treating, preventing and/or alleviating the symptoms of disorders relating to platelet-mediated aggregation or dysfunction thereof. Said disorders include, thrombotic thrombocytopenic purpura (TTP), transient cerebral ischemic attack, unstable or stable angina pectoris, cerebral infarction, myocardial infarction, peripheral arterial occlusive disease, restenosis. Said disorders further include those arising from coronary by-pass graft, coronary artery valve replacement and coronary interventions such angioplasty, stenting, or atherectomy.

Other disorders are any of the formation of a non-occlusive thrombus, the formation of an occlusive thrombus, arterial thrombus formation, acute coronary occlusion, restenosis, restenosis after PCTA or stenting, thrombus formation in stenosed arteries, hyperplasia after angioplasty, atherectomy or arterial stenting, occlusive syndrome in a vascular system or lack of patency of diseased arteries.

One aspect of the invention is a polypeptide construct as disclosed herein for use in the treatment, prevention and/or alleviation of disorders or conditions relating to platelet-mediated aggregation or dysfunction thereof, wherein said polypeptide construct is administered intravenously, subcutaneously, orally, sublingually, topically, nasally, vaginally, rectally or by inhalation.

Another aspect of the invention is the use of a polypeptide construct as disclosed herein for the preparation of a medicament for the treatment, prevention and/or alleviation of disorders or conditions relating to platelet-mediated aggregation or dysfunction thereof, wherein said polypeptide construct is administered intravenously, subcutaneously, orally, sublingually, topically, nasally, vaginally, rectally or by inhalation.

Another aspect of the invention is a method of treating, preventing and/or alleviating disorders or conditions relating to relating to platelet-mediated aggregation or dysfunction thereof, comprising administering to a subject a polypeptide construct as disclosed herein, wherein said heterospecific polypeptide construct is administered intravenously, subcutaneously, orally, sublingually, topically, nasally, vaginally, rectally or by inhalation.

Another aspect of the invention is a polypeptide construct as disclosed herein for use in the treatment, prevention and/or alleviation of disorders or conditions relating to platelet-mediated aggregation or dysfunction thereof.

Another aspect of the invention is a use of a polypeptide as disclosed herein for the preparation of a medicament for the treatment, prevention and/or alleviation of disorders or conditions relating to platelet-mediated aggregation or dysfunction thereof.

One can use a polypeptide construct of the present invention in order to screen for agents that modulate the binding of the polypeptide to a vWF (or gpIb or collagen). When identified in an assay that measures binding or said polypeptide displacement alone, agents will have to be subjected to functional testing to determine whether they act as modulators of platelet-mediated aggregation.

In an example of a displacement experiment, phage or cells expressing vWF or a fragment thereof are incubated in binding buffer with, for example, a polypeptide represented by SEQ ID NO: 1 which has been labeled, in the presence or absence of increasing concentrations of a candidate modulator. To validate and calibrate the assay, control competition reactions using increasing concentrations of said polypeptide and which is unlabeled, can be performed. After incubation, cells are washed extensively, and bound, labelled polypeptide is measured as appropriate for the given label (e.g., scintillation counting, fluorescence, etc.). A decrease of at least 10% in the amount of labelled polypeptide bound in the presence of candidate modulator indicates displacement of binding by the candidate modulator. Candidate modulators are considered to bind specifically in this or other assays described herein if they displace 50% of labelled polypeptide (sub-saturating polypeptide dose) at a concentration of 1 μM or less. Of course, the above method might easily be applied to screening for candidate modulators which alter the binding between the polypeptides represented by SEQ ID NOs: 2 to 15, 20 to 47 and 62 to 65 or the polypeptide constructs disclosed herein, and macromolecules involved in platelet-mediated aggregation such as, for example, vWF, gpIb or collagen, or a fragment thereof.

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of, for example, the polypeptide represented by SEQ ID NO: 1 from the aqueous phase to a vWF, or fragment thereof immobilized in a membrane on the sensor. This change in mass is measured as resonance units versus time after injection or removal of the said polypeptide or candidate modulator and is measured using a Biacore Biosensor (Biacore AB). vWF, or fragment thereof can be for example immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for the binding of a polypeptide construct of the invention in an SPR assay can be fine-tuned by one of skill in the art using the conditions reported by Sarrio et al. as a starting point. Of course, the above method might easily be applied to screening for candidate modulators which alter the binding between the polypeptide constructs disclosed herein and macromolecules involved in platelet-mediated aggregation such as, for example, vWF, gpIb or collagen, or a fragment thereof.

SPR can assay for modulators of binding in at least two ways. First, a polypeptide represented by SEQ ID NO: 1, for example, can be pre-bound to immobilized vWF, or fragment thereof, followed by injection of candidate modulator at a concentration ranging from 0.1 nM to 1 µM. Displacement of the bound polypeptide can be quantitated, permitting detection of modulator binding. Alternatively, the membrane-bound vWF, or fragment thereof can be pre-incubated with a candidate modulator and challenged with, for example, a polypeptide represented by SEQ ID NO: 1. A difference in binding affinity between said polypeptide and vWF, or fragment thereof pre-incubated with the modulator, compared with that between said polypeptide and vWF, or fragment thereof in absence of the modulator will demonstrate binding or displacement of said polypeptide in the presence of modulator. In either assay, a decrease of 10% or more in the amount of said polypeptide bound in the presence of candidate modulator, relative to the amount of said polypeptide bound in the absence of candidate modulator indicates that the candidate modulator inhibits the interaction of vWF, or fragment thereof and said polypeptide. Of course, the above method might easily be applied to screening for candidate modulators which alter the binding between the polypeptides represented by SEQ ID NOs: 2 to 15, 20 to 47 and 62 to 65 or the polypeptide constructs disclosed herein, and macromolecules involved in platelet-mediated aggregation such as, for example, vWF, gpIb, or collagen, or a fragment thereof.

Another method of detecting inhibition of binding of, for example, a polypeptide represented by SEQ ID NOs: 1 to 15, 20 to 34, 38 to 45 or 62 to 65 to vWF, or fragments thereof uses fluorescence resonance energy transfer (FRET). FRET is a quantum mechanical phenomenon that occurs between a fluorescence donor (D) and a fluorescence acceptor (A) in close proximity to each other (usually <100 Å of separation) if the emission spectrum of D overlaps with the excitation spectrum of A. The molecules to be tested, e.g. a polypeptide represented by SEQ ID NO: 1 and a vWF, or fragment thereof, are labelled with a complementary pair of donor and acceptor fluorophores. While bound closely together by the vWF:polypeptide interaction, the fluorescence emitted upon excitation of the donor fluorophore will have a different wavelength from that emitted in response to that excitation wavelength when the said polypeptide and vWF, or fragment thereof are not bound, providing for quantitation of bound versus unbound molecules by measurement of emission intensity at each wavelength. Donor fluorophores with which to label the vWF, or fragment thereof are well known in the art. Of particular interest are variants of the A. Victoria GFP known as Cyan FP (CFP, Donor (D)) and Yellow FP (YFP, Acceptor (A)). As an example, the YFP variant can be made as a fusion protein with vWF, or fragment thereof. Vectors for the expression of GFP variants as fusions (Clontech) as well as fluorophore-labeled reagents (Molecular Probes) are known in the art. The addition of a candidate modulator to the mixture of fluorescently-labelled polypeptide and YFP-vWF will result in an inhibition of energy transfer evidenced by, for example, a decrease in YFP fluorescence relative to a sample without the candidate modulator. In an assay using FRET for the detection of vWF:polypeptide interaction, a 10% or greater decrease in the intensity of fluorescent emission at the acceptor wavelength in samples containing a candidate modulator, relative to samples without the candidate modulator, indicates that the candidate modulator inhibits the vWF:polypeptide interaction. Of course, the above method might easily be applied to screening for candidate modulators which alter the binding between the polypeptides represented by any of SEQ ID NOs: 2 to 15, 20 to 47, 62 to 65 or the polypeptide constructs disclosed herein, and macromolecules involved in platelet-mediated aggregation such as, for example, vWF, gpIb or collagen, or a fragment thereof.

A variation on FRET uses fluorescence quenching to monitor molecular interactions. One molecule in the interacting pair can be labeled with a fluorophore, and the other with a molecule that quenches the fluorescence of the fluorophore when brought into close apposition with it. A change in fluorescence upon excitation is indicative of a change in the association of the molecules tagged with the fluorophore:quencher pair. Generally, an increase in fluorescence of the labeled vWF, or fragment thereof is indicative that the polypeptide molecule (e.g. a polypeptide construct of the invention) bearing the quencher has been displaced. For quenching assays, a 10% or greater increase in the intensity of fluorescent emission in samples containing a candidate modulator, relative to samples without the candidate modulator, indicates that the candidate modulator inhibits vWF:polypeptide interaction. Of course, the above method might easily be applied to screening for candidate modulators which alter the binding between the polypeptide constructs disclosed herein, and macromolecules involved in platelet-mediated aggregation such as, for example, vWF, gpIb or collagen, or a fragment thereof.

In addition to the surface plasmon resonance and FRET methods, fluorescence polarization measurement is useful to quantitate binding. The fluorescence polarization value for a fluorescently-tagged molecule depends on the rotational correlation time or tumbling rate. Complexes, such as those formed by vWF, or fragment thereof associating with a fluorescently labelled polypeptide (e.g. a fluorescently-labeled polypeptide represented by any of SEQ ID NOs: 1 to 15, 20 to 34, 38 to 45 and 62 to 65), have higher polarization values than uncomplexed, labeled polypeptide. The inclusion of a candidate inhibitor of the vWF:polypeptide interaction results in a decrease in fluorescence polarization, relative to a mixture without the candidate inhibitor, if the candidate inhibitor disrupts or inhibits the interaction of vWF, or fragment thereof with said polypeptide. Fluorescence polarization is well suited for the identification of small molecules that disrupt the formation of vWF:polypeptide complexes. A decrease of 10% or more in fluorescence polarization in samples containing a candidate modulator, relative to fluorescence polarization in a sample lacking the candidate modulator, indicates that the candidate modulator inhibits the vWF:polypeptide interaction. Of course, the above method might easily be applied to screening for candidate modulators which alter the binding between the polypeptide constructs disclosed herein, and macromolecules involved in platelet-mediated aggregation such as, for example, vWF, gpIb or collagen, or a fragment thereof.

Another alternative for monitoring vWF:polypeptide interactions uses a biosensor assay. ICS biosensors have been described in the art (Australian Membrane Biotechnology Research Institute; Cornell B, Braach-Maksvytis V, King L, Osman P, Raguse B, Wieczorek L, and Pace R. "A biosensor that uses ion-channel switches" Nature 1997, 387, 580). In this technology, the association of vWF, or fragment thereof and a polypeptide (e.g. a polypeptide represented by any of SEQ ID NOs: 1 to 15, 20 to 34, 38 to 45 and 62 to 65) is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of vWF, or fragment thereof and said polypeptide. It is important to note that in assays testing the interaction of vWF, or fragment thereof with a polypeptide (such as for example, a polypeptide represented by any of SEQ ID NOs: 1 to 15, 20 to 34, 38 to 45 and 62 to 65), it is possible that a modulator of the interaction need not necessarily interact directly with the domain(s) of the proteins that physically interact with said polypeptide. It is also possible that a modulator will interact at a location removed from the site of interaction and cause, for example, a conformational change in the vWF. Modulators (inhibitors or agonists) that act in this manner are nonetheless of interest as agents to modulate platelet-mediated aggregation. Of course, the above method might easily be applied to screening for candidate modulators which alter the binding between the polypeptide constructs disclosed herein, and macromolecules involved in platelet-mediated aggregation such as, for example, vWF, gpIb or collagen, or a fragment thereof.

Any of the binding assays described can be used to determine the presence of an agent in a sample, e.g., a tissue sample, that binds to vWF, or fragment thereof, or that affects the binding of, for example, a polypeptide represented by any of SEQ ID NO: 1 to 15, 20 to 34, 38 to 45 or 62 to 65 to the vWF. To do so a vWF, or fragment thereof is reacted with said polypeptide in the presence or absence of the sample, and polypeptide binding is measured as appropriate for the binding assay being used. A decrease of 10% or more in the binding of said polypeptide indicates that the sample contains an agent that modulates the binding of said polypeptide to the vWF, or fragment thereof. Of course, the above generalised method might easily be applied to screening for candidate modulators which alter the binding between the polypeptide constructs disclosed herein, and macromolecules involved in platelet-mediated aggregation such as, for example, vWF, gpIb or collagen, or a fragment thereof.

Cells

A cell that is useful according to the invention is preferably selected from the group consisting of bacterial cells such as, for example, *E. coli*, yeast cells such as, for example, *S. cerevisiae*, *P. pastoris*, insect cells or mammalian cells.

A cell that is useful according to the invention can be any cell into which a nucleic acid sequence encoding a polypeptide comprising any of SEQ ID NOs: 1 to 47 and 49 to 65 or a polypeptide construct of the invention according to the invention can be introduced such that the polypeptide is expressed at natural levels or above natural levels, as defined herein. Preferably a polypeptide of the invention that is expressed in a cell exhibits normal or near normal pharmacology, as defined herein. Most preferably a polypeptide of the invention that is expressed in a cell comprises the nucleotide sequence capable of encoding the amino acid sequences presented in Table 30 or capable of encoding a amino acid sequence that is at least 70% identical to the amino acid sequence presented in Table 30.

According to a preferred embodiment of the present invention, a cell is selected from the group consisting of COS7-cells, a CHO cell, a LM (TK-) cell, a NIH-3T3 cell, HEK-293 cell, K-562 cell or a 1321N1 astrocytoma cell but also other transfectable cell lines.

In general, "therapeutically effective amount", "therapeutically effective dose" and "effective amount" means the amount needed to achieve the desired result or results (treating or preventing platelet aggregation). One of ordinary skill in the art will recognize that the potency and, therefore, an "effective amount" can vary for the various compounds that inhibit platelet-mediated aggregation used in the invention. One skilled in the art can readily assess the potency of the compound.

As used herein, the term "compound" refers the polypeptide constructs disclosed herein, or to a nucleic acid capable of encoding said polypeptide, or an agent identified according to the screening method described herein or said polypeptide comprising one or more derivatised amino acids.

By "pharmaceutically acceptable" is meant a material that is not biologically or otherwise undesirable, i.e., the material may be administered to an individual along with the compound without causing any undesirable biological effects or interacting in a deleterious manner with any of the other components of the pharmaceutical composition in which it is contained.

The invention disclosed herein is useful for treating or preventing a condition of platelet-mediated aggregation, in a subject and comprising administering a pharmaceutically effective amount of a compound or composition that inhibits BTK and that inhibits platelet-mediated aggregation.

The invention disclosed herein is useful for treating or preventing the first steps of thrombus formation, in a subject and comprising administering a pharmaceutically effective amount of a compound or composition according to the invention.

The invention disclosed herein is useful for treating or preventing restenosis, in a subject and comprising administering a pharmaceutically effective amount of a compound or composition according to the invention.

One aspect of the present invention is the use of compounds of the invention for treating or preventing a condition of platelet-mediated aggregation, in a subject and comprising administering a pharmaceutically effective amount of a compound in combination with another, such as, for example, aspirin.

One aspect of the present invention is the use of compounds of the invention for treating or preventing a condition of platelet-mediated aggregation, in a subject and comprising administering a pharmaceutically effective amount of a compound in combination with another, such as, for example, a thrombolytic agent.

Another aspect of the present invention is a use of a compound of the invention for treating or preventing plaque or thrombus in an individual. Said plaque or thrombus formation may be under conditions of high sheer. In both thrombosis and reocclusion, the reversible adhesion or tethering of the platelets at high shear rate is followed by a firm adhesion through the collagen receptor on platelets resulting in platelet activation; the tethering of platelets by vWF to collagen exposed in the damaged vessel wall is especially important under high shear conditions. The inventors have found that polypeptide constructs of the present invention unexpected performed well under high sheer conditions (e.g. Example 16.)

The present invention is not limited to the administration of formulations comprising a single compound of the invention. It is within the scope of the invention to provide combination treatments wherein a formulation is administered to a patient in need thereof that comprises more than one compound of the invention.

Conditions of platelet-mediated aggregation include, but are not limited to, unstable angina, stable angina, angina pectoris, embolus formation, deep vain thrombosis, hemolytic uremic syndrome, hemolytic anemia, acute renal failure, thrombolytic complications, thrombotic thrombocytopenic purpura, disseminated intravascular comgelopathy, thrombosis, coronary heart disease, thromboembolic complications, myocardial infarction, restenosis, and atrial thrombosis formation in atrial fibrillation, chronic unstable angina, transient ischemic attacks and strokes, peripheral vascular disease, arterial thrombosis, pre-eclampsia, embolism, restenosis and/or thrombosis following angioplasty, carotid endarterectomy, anastomosis of vascular grafts, and chronic exposure to cardiovascular devices. Such conditions may also result from thromboembolism and reocclusion during and after thrombolytic therapy, after angioplasty, and after coronary artery bypass.

It is well known in the art how to determine the inhibition of platelet-mediated aggregation using the standard tests described herein, or using other similar tests. Preferably, the method would result in at least a 10% reduction in platelet-mediated aggregation, including, for example, 15%, 20%, 25%, 30%, 40%, 50%, 60%, 70%, 80%, 90%, 100%, or any amount in between, more preferably by 90%.

Similarly, the method would result in at least a 10% reduction in intracellular calcium mobilisation including, for example, 15%, 20%, 25%, 30%, 40%, 50%, 60%, 70%, 80%, 90%, 100%. Similarly, the method would result in at least a 10% reduction in the level of phosphorylated PLCg 2 including, for example, 15%, 20%, 25%, 30%, 40%, 50%, 60%, 70%, 80%, 90%, 100%.

The reduction can be measured, for example, by comparing the optical impedence in a chronology platelet aggregometer. Any other known measurement method may also be used. For example, (1) upon collagen stimulation, the level of collagen-induced intracellular calcium mobilization increases over time and so the measurement may include measuring the level of collagen-induced intracellular calcium or (2) upon collagen stimulation, the level of phosphorylated PLCg 2 increases over time and so the measurement may include measuring the level of phosphorylated PLCg 2.

The cells can be contacted in vitro, for example, by adding a compound of the invention to the culture medium (by continuous infusion, by bolus delivery, or by changing the medium to a medium that contains the compound) or by adding the compound to the extracellular fluid in vivo (by local delivery, systemic delivery, inhalation, intravenous injection, bolus delivery, or continuous infusion). The duration of "contact" with a cell or population of cells is determined by the time the compound is present at physiologically effective levels or at presumed physiologically effective levels in the medium or extracellular fluid bathing the cell or cells. Preferably, the duration of contact is 1-96 hours, and more preferably, for 24 hours, but such time would vary based on the half life of the compound and could be optimized by one skilled in the art using routine experimentation.

The compound useful in the present invention can be formulated as pharmaceutical compositions and administered to a mammalian host, such as a human patient or a domestic animal in a variety of forms adapted to the chosen route of administration, i.e., orally or parenterally, by intranasally by inhalation, intravenous, intramuscular, topical or subcutaneous routes.

The compound of the present invention can also be administered using gene therapy methods of delivery. See, e.g., U.S. Pat. No. 5,399,346, which is incorporated by reference in its entirety. Using a gene therapy method of delivery, primary cells transfected with the gene for the compound of the present invention can additionally be transfected with tissue specific promoters to target specific organs, tissue, grafts, tumors, or cells.

Thus, the present compound may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compound may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the present compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compound to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. Also the dosage of the compound varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

The invention provides for an agent that is a modulator of platelet-mediated aggregation.

The candidate agent may be a synthetic agent, or a mixture of agents, or may be a natural product (e.g. a plant extract or culture supernatant). A candidate agent according to the invention includes a small molecule that can be synthesized, a natural extract, peptides, proteins, carbohydrates, lipids etc.

Candidate modulator agents from large libraries of synthetic or natural agents can be screened. Numerous means are currently used for random and directed synthesis of saccharide, peptide, and nucleic acid based agents. Synthetic agent libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural agents in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and agents are readily modified through conventional chemical, physical, and biochemical means.

Useful agents may be found within numerous chemical classes. Useful agents may be organic agents, or small organic agents. Small organic agents have a molecular weight of more than 50 yet less than about 2,500 daltons, preferably less than about 750, more preferably less than about 350 daltons. Exemplary classes include heterocycles, peptides, saccharides, steroids, and the like. The agents may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

For primary screening, a useful concentration of a candidate agent according to the invention is from about 10 mM to about 100 µM or more (i.e. 1 mM, 10 mM, 100 mM, 1 M etc.). The primary screening concentration will be used as an upper limit, along with nine additional concentrations, wherein the additional concentrations are determined by reducing the primary screening concentration at half-log intervals (e.g. for 9 more concentrations) for secondary screens or for generating concentration curves.

High Throughput Screening Kit

A high throughput screening kit according to the invention comprises all the necessary means and media for performing the detection of an agent that modulates platelet-mediated aggregation by interacting with a target of the invention, such as for example vWF, or fragment thereof in the presence of a polypeptide (for example, a polypeptide represented by SEQ ID NOs: 1 to 15, 20 to 34, 38 to 45, 62 to 65 or a polypeptide construct), preferably at a concentration in the range of 1µM to 1 mM. The kit comprises the following. Recombinant cells of the invention, comprising and expressing the nucleotide sequence encoding vWF, or fragment thereof, which are grown according to the kit on a solid support, such as a microtiter plate, more preferably a 96 well microtiter plate, according to methods well known to the person skilled in the art especially as described in WO 00/02045. Alternatively vWF, or fragment thereof is supplied in a purified form to be immobilized on, for example, a 96 well microtiter plate by the person skilled in the art. Alternatively vWF, or fragment thereof is supplied in the kit pre-immobilized on, for example, a 96 well microtiter plate. Alternatively, in cases where the macromolecule to be screened against is gpIb, gpIa/IIa, or collagen, the above embodiments would carry gpIb, gpIa/IIa, or collagen polypeptide or polynucleic acid respectively in place of vWF. Kit may contain more than one macromolcule (e.g. vWF, gpIb or collagen macromolecule and/or polynucleic acid). Modulator agents according to the invention, at concentrations from about 1 µM to 1 mM or more, are added to defined wells in the presence of an appropriate concentration of polypeptide construct said concentration of said polypeptide preferably in the range of 1 µM to 1 mM. Kits may contain more than one polypeptide Binding assays are performed as according to the methods already disclosed herein and the results are compared to the baseline level of, for example vWF, or fragment thereof binding to a polypeptide, such as, for example, a polypeptide represented by any of SEQ ID NOs: 2 to 15, 20 to 34, 38 to 45 or 62 to 65, but in the absence of added modulator agent. Wells showing at least 2 fold, preferably 5 fold, more preferably 10 fold and most preferably a 100 fold or more increase or decrease in vWF-polypeptide binding (for example) as compared to the level of activity in the absence of modulator, are selected for further analysis.

Other Kits Useful According to the Invention

The invention provides for kits useful for screening for modulators of platelet-mediated aggregation, as well as kits useful for diagnosis of diseases or disorders characterised by dysregulation platelet-mediated aggregation. Kits useful according to the invention can include an isolated vWF, or fragment thereof. Alternatively, or in addition, a kit can comprise cells transformed to express vWF, or fragment thereof. In a further embodiment, a kit according to the invention can comprise a polynucleotide encoding vWF, or fragment thereof. In a still further embodiment, a kit according to the invention may comprise the specific primers useful for amplification of vWF, or fragment thereof. Alternatively, in cases where the macromolecule to be screened against is gpIb, or collagen, the above embodiments would carry gpIb, gpIa/IIa, or collagen polypeptide or polynucleic acid, or fragment thereof respectively in place of vWF. Kit may contain more than one macromolcule (e.g. vWF, gpIb, or collagen macromolecule or polynucleic acid, or fragment thereof). Kits useful according to the invention can comprise an isolated polypeptide represented by any of SEQ ID NOs: 1 to 15, 20 to 47 or 62 to 65, a homologue thereof, or a functional portion thereof, or a polypeptide construct according to the invention. A kit according to the invention can comprise cells transformed to express said polypeptide. Kits may contain more than one polypeptide. In a further embodiment, a kit according to the invention can comprise a polynucleotide encoding a macromolecule, for example, vWF, gpIb, or collagen, or fragment thereof. In a still further embodiment, a kit according to the invention may comprise the specific primers useful for amplification of a macromolecule such as, for example, vWF gpIb, or collagen, or fragment thereof. All kits according to the invention will comprise the stated items or combinations of items and packaging materials therefore. Kits will also include instructions for use.

Medical Devices

The invention also provides for invasive medical devices coated with a polypeptide construct of the invention or an agent resulting from a screening method of the invention for use in devices requiring the same. Non-limiting examples of devices include surgical tubing, occlusion devices, prosthetic devices. Application for said devices include surgical procedures which require a modulation of platelet-mediated aggregation around the site of invasion.

One embodiment of the present is a method for treating invasive medical devices to prevent platelet-mediate aggregation around the site of invasion comprising the step of coating said device with a polypeptide construct or agent according to the invention.

Another embodiment of the present is a invasive medical devices that circumvents platelet-mediate aggregation around the site of invasion, wherein said device is coated with a polypeptide construct or agent according to the invention.

EXAMPLES

The invention is illustrated by the following non-limiting examples.

Legend to Examples

Example 1. Immunization of llama002

Example 2. Repertoire cloning

Example 3. Rescue of the library, phage preparation

Selection for binders for vWF inhibiting the interaction with collagen:

Example 4. Selection for binders for vWF inhibiting the interaction with collagen first and second round of panning Example 5. Functional characterization of vWF binders
Inhibition of binding of vWF to collagen by VHH
Example 6. Expression and purification of VHH
Example 7. ELISA binding to vWF
Example 8. Specificity of the VHHs
Example 9. Inhibition ELISA with purified VHH
Example 10. Sequencing of the clones
Example 11. Epitope mapping
Example 12. Bivalent and bispecific VHHs expression and purification
Example 13. Binding in ELISA to vWF
Example 14. Inhibition ELISA with purified VHH
Example 15. Stability of bivalent or bispecific constructs in human plasma
Example 16. Evaluate inhibition by VHH at high shear.
Selection of binders for vWF inhibiting the interaction with platelets:
Example 17. Selection of binders for vWF inhibiting the interaction with platelets panning
Example 18. Screening for binding to the A1 domain of vWF
Example 19. Selection of binders for vWF inhibiting the interaction with platelets MATCHM
Example 20. ELISA binding to vWF of purified VHH
Example 21. Inhibition ELISA with purified VHH
Example 22. Sequencing of the clones
Example 23. Evaluate inhibition by VHH at high shear.
Example 24. Bivalent VHHs expression and purification
Example 25. Evaluate inhibition by VHH at high shear.
Make bispecific constructs for vWF-specific VHH:
Example 26. Construction and sequence of bispecific constructs
Example 27. Expression and purification of bispecific constructs
Example 28. Binding to vWF
Example 29. Inhibition of binding of vWF to collagen by the bispecific constructs as compared to the monovalent VHHs
Example 30. Evaluate inhibition by VHH at high shear.
Screening for binders for collagen type I and type III:
Example 31. Selection of binders for collagen type I
Example 32. Test VHH in ELISA for binding to collagen type I and type III.
Example 33. Sequencing of the clones
Example 34. Binding of purified VHH to collagen type I and type III
Example 35. Selection of binders for collagen type I inhibiting the interaction with vWF
Example 36. Test VHH in ELISA for binding to collagen type I and type III.
Example 37. Sequencing of the clones
Example 38. Binding of purified VHH to collagen type I and type III
Example 39. Test inhibition of binding of vWF to collagen by collagen-specific VHH in ELISA
Example 40. Test inhibition of platelet aggregation by collagen-specific VHH at low and at high shear
Improved half-life of VHH:
Example 41. Immunization of llamas
Example 42. Repertoire cloning
Example 43. Rescue of the library, phage preparation
Example 44. Phage ELISA
Example 45. Selection first and second round of biopanning
Example 46. Screening of individual clones after biopanning
Example 47. HinfI pattern and sequencing
Example 48. Test cross-reactivity with albumin of different species
Example 49. Expression and purification
Example 50. ELISA on MSA of the purified nanobodies
Example 51. Construction and sequence of bispecific constructs
Example 52. Expression and purification of bispecific constructs
Example 53. Functionality of both VHHs in the bispecific construct
Example 54. Inhibition of binding of vWF to collagen by the bispecific constructs as compared to the monovalent VHHs
Selection of binders for gpIb inhibiting the interaction with vWF:
Example 55. Selection of binders for rgpIb
Example 56. Screening for binders in ELISA.
Example 57. Binding of purified VHH to rgpIb
Example 58. Sequencing of the clones
Example 59. Test inhibitory properties of VHHs specific for gpIb
Example 60. Evaluate inhibition by VHH at high shear.
Coating of stents, tubings, balloons, catheters, transplantation material with VHH:
Example 61. Stability of VHH
Example 62. VHH immobilized in a polymer
Humanisation of C37:
Example 63. Alignment of C37 with DP-47
Example 64. Mutagenesis of C37
Fragments of anti-VWF VHHs
Example 65. Expression of a VHH-CDR3 fragment of vWF-C37
Example 66. Selection via first and second round biopanning on recombinant A1 (rA1)
Example 67. Screening of individual clones after biopanning
Example 68. HinfI pattern and sequencing
Example 69. Inhibition ELISA

EXAMPLES

Example 1: Immunization of Llama002

One llama was immunized with a cocktail of vWF and collagen type I and type III. Those antigens are all involved in the first interactions leading to platelet aggregation (FIG. 1). The immunization scheme is summarized in Table 1

Example 2: Repertoire Cloning

Peripheral blood lymphocytes (PBLs) were isolated by centrifugation on a density gradient (Ficoll-Paque Plus Amersham Biosciences). PBLs were used to extract total RNA (Chomczynski and Sacchi 1987). cDNA was prepared on 100 μg total RNA with MMLV Reverse Transcriptase (Gibco BRL) using oligo d(T) oligonucleotides. The cDNA was purified with a phenol/chloroform extraction, followed by an ethanol precipitation and subsequently used as template to amplify the VHH repertoire.

In a first PCR, the repertoire of both conventional (1.6 kb) and heavy-chain (1.3 kb) antibody gene segments were amplified using a leader specific primer (5'-GGCTGAGCTCGGTGGTCCTGGCT-3'; SEQ ID NO: 66) and the oligo d(T) primer (5'-AACTGGAAGAATTCGCGGCCGCAGGAATTTTTTTTTTTTTTTTTT-3'; SEQ ID NO: 67). The resulting DNA fragments were separated by agarose gel electrophoresis and the 1.3 kb fragment, encoding heavy-chain antibody segments was purified from the agarose gel. A second PCR was performed using a mixture of FR1 reverse primers and the same oligo d(T) forward primer. The PCR products were digested with SfiI (introduced in the FR1 primer) and BstEII (naturally occurring in FR4). Following gel electrophoresis, the DNA fragment of approximately 400 basepairs were purified from gel and ligated into the corresponding restriction sites of phagemid pAX004 to obtain a library of cloned VHHs after electroporation of *Escherichia coli* TG1. The size of the library was $1.4 \times 10^7$ cfu, and all clones contained insert of the correct size.

Example 3: Rescue of the Library, Phage Preparation

Figure 2:
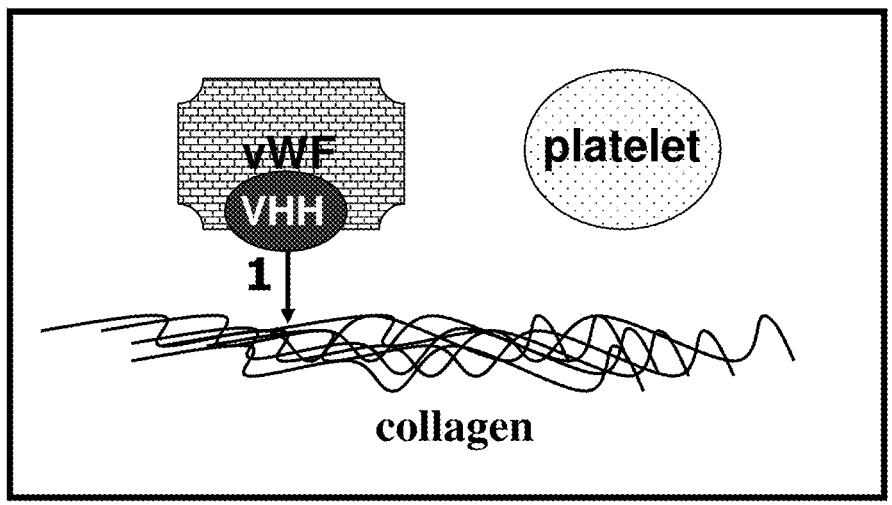

The library was grown at 37° C. in 10 ml 2×TY medium containing 2% glucose, and 100 µg/ml ampicillin, until the OD600 nm reached 0.5. M13KO7 phages ($10^{12}$) were added and the mixture was incubated at 37° C. for 2×30 minutes, first without shaking, then with shaking at 100 rpm. Cells were centrifuged for 10 minutes at 4500 rpm at room temperature. The bacterial pellet was resuspended in 50 ml of 2×TY medium containing 100 µg/ml ampicillin and 25 µg/ml kanamycin, and incubated overnight at 37° C. with vigorously shaking at 250 rpm. The overnight cultures were centrifuged for 15 minutes at 10000 rpm at 4° C. Phages were PEG precipitated (20% poly-ethylene-glycol and 1.5 M NaCl) and centrifuged for 30 minutes at 10000 rpm. The pellet was resuspended in 20 ml PBS. Phages were again PEG precipitated and centrifuged for 30 minutes at 20000 rpm and 4° C. The pellet was dissolved in 5 ml PBS-1% casein. Phages were titrated by infection of TG1 cells at OD600 nm=0.5 and plating on LB agar plates containing 100 µg/ml ampicillin and 2% glucose. The number of transformants indicates the number of phages (=pfu). The phages were stored at −80° C. with 15% glycerol.
Selection for Binders for vWF Inhibiting the Interaction with Collagen (FIG. 2)

Example 4: Selection for Binders for vWF Inhibiting the Interaction with Collagen: First and Second Round of Panning A well in a microtiterplate was coated with 2 µg/ml vWF or with PBS containing 1% casein. After overnight incubation at 4° C., the wells were blocked with PBS containing 1% casein, for 3 hours at RT. 200 µl phages was added to the wells. After 2 hours incubation at RT, the wells were washed 10× with PBS-Tween and 10× with PBS. Phages were specifically eluted with 100 µl of 100 µg/ml collagen type III. Elutions were performed for overnight at room temperature. Eluted phages were allowed to infect exponentially growing TG1 cells, and were then plated on LB agar plates containing 100 µg/ml ampicillin and 2% glucose. This experiment was repeated for a second round of panning, under the same conditions as described above. The results from the panning are presented in Table 2.

Example 5: Functional Characterization of vWF Binders: Inhibition of Binding of vWF to Collagen by VHH A microtiter plate was coated overnight at 4° C. with collagen type III at 25 µg/ml in PBS. The plate was washed five times with PBS-Tween and blocked for 2 hours at room temperature with PBS containing 1% casein. The plate was washed five times with PBS-tween. 100 µl of 2 µg/ml vWF (vWF is pre-incubated at 37° C. for 15 minutes) was mixed with 20 µl periplasmic extract containing a VHH antibody (described in Example 6) and incubated for 90 minutes at room temperature in the wells of the microtiterplate. The plate was washed five times with PBS-tween. An anti-vWF-HRP monoclonal antibody (DAKO) was diluted 3,000-fold in PBS and incubated for 1 hour. The plate was washed five times with PBS-Tween and vWF-binding was detected with $ABTS/H_2O_2$. Signals were measured after 30 minutes at 405 nm. The results are presented in Table 3, showing that inhibitors are obtained after the first and second round of panning.

Example 6: Expression and Purification of VHH

Plasmid was prepared for binders for vWF inhibiting the interaction with collagen typeIII and was transformed into WK6 electrocompetent cells. A single colony was used to start an overnight culture in LB containing 2% glucose and 100 µg/ml ampicillin. This overnight culture was diluted 100-fold in 300 ml TB medium containing 100 µg/ml ampicillin, and incubated at 37° C. until OD600 nm=0.5. 1 mM IPTG was added and the culture was incubated for 3 more hours at 37° C. or overnight at 28° C.

Cultures were centrifuged for 20 minutes at 10000 rpm at 4° C. The pellet was frozen overnight or for 1 hour at −20° C. Next, the pellet was thawed at room temperature for 40 minutes, re-suspended in 20 ml PBS and shaken on ice for 1 hour. Periplasmic fraction was isolated by centrifugation for 20 minutes at 4° C. at 20000 rpm. The supernatant containing the VHH was loaded on Ni-NTA and purified to homogeneity. The yield of VHH was calculated according to the extinction coefficient. Results are summarized in Table 4.

Example 7: ELISA: Binding to vWF

Figure 3:
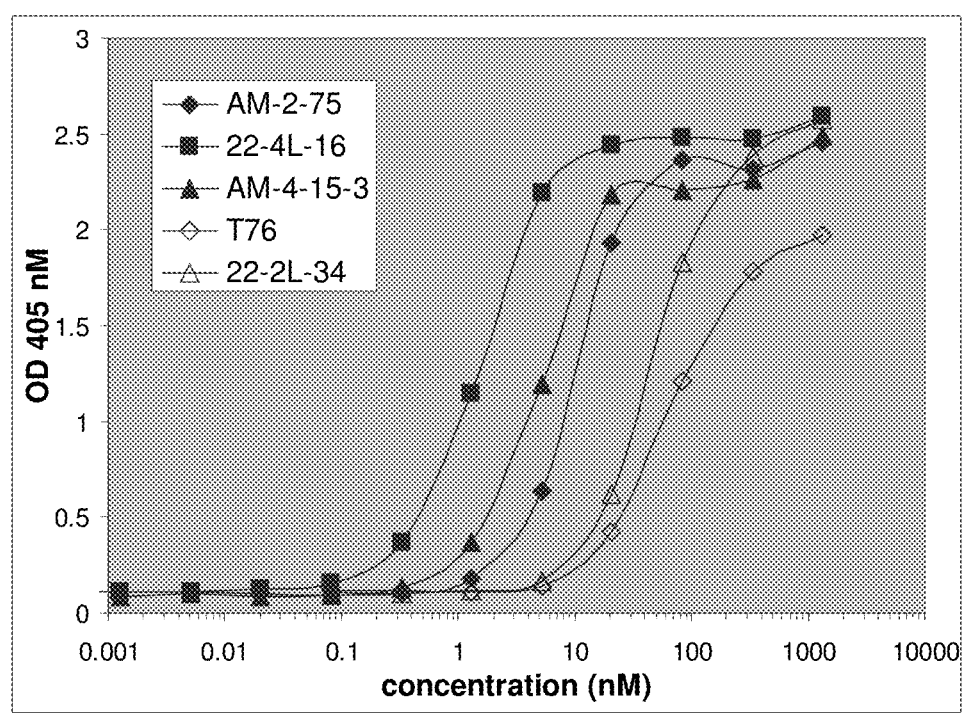

A microtiter plate was coated with 2 µg/ml vWF, overnight at 4° C. Plates were blocked for two hours at room temperature with 300 µl 1% casein in PBS. The plates were washed three times with PBS-Tween. Dilution series of all purified samples were incubated for 2 hours at RT. Plates were washed six times with PBS-Tween, after which binding of VHH was detected by incubation with mouse anti-myc mAB 1/2000 in PBS for 1 hour at RT followed by anti-mouse-HRP conjugate 1/1000 in PBS, also for 1 hour at RT. Staining was performed with the substrate $ABTS/H_2O_2$ and the signals were measured after 30 minutes at 405 nm. The binding as a function of concentration of purified VHH is indicated in FIG. 3.

Example 8: Specificity of the VHHs

Microtiterplates were coated with 2 µg/ml vWF and 3 other antigens not involved in platelet aggregation, but that were also immunized in llama 002. ELISA was performed as described in Example 7 with 670, 67 and 6.7 nM VHH. Results are summarized in Table 5. The results show that the inhibitory VHH are specific for vWF.

Example 9: Inhibition ELISA with Purified VHH

Figure 4:
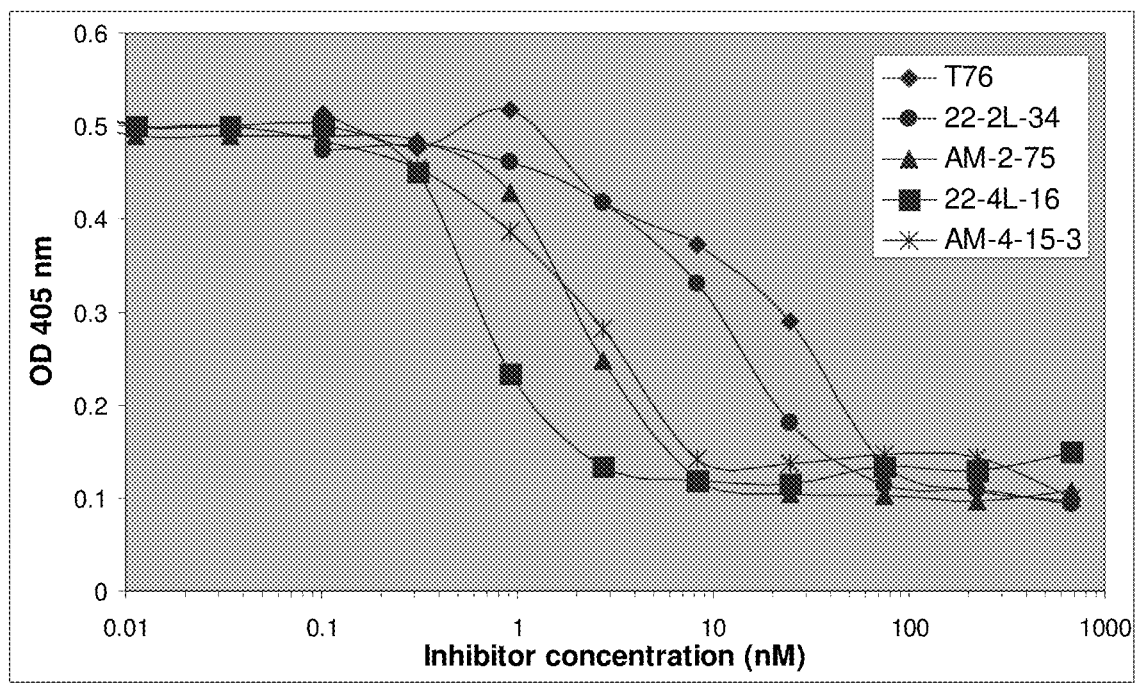

Inhibition ELISA was performed as described in Example 5 but with decreasing concentrations of VHH and with human plasma at a dilution of 1/60 instead of with purified vWF or with human undiluted plasma. Results are represented in FIG. 4. The concentration of VHH resulting in 50% inhibition (IC50) is given in Table 6.

Example 10: Sequencing of the Clones

Clones were sequenced with M13 universal reverse primer. Amino acid sequences are shown in Table 30 (SEQ ID numbers 1, 3, 4, 5, 6 and 7).

Example 11: Epitope Mapping

Cloning the A3 Domain of vWF in pBAD-Oprl-ss

The pBAD-Oprl-strep-spec vector was used to display the VWF A3 domain as a fusion with Oprl on the surface of UT5600 E. coli cells (F-ara-14 leuB6 azi-6 lacY1 proC14 tsx-67 entA403 trpE38 rfbD1 rpsL109 xyl-5 mtl-1 thi1 DompT fepC266) (Cote-Sierra et al, 1998, Gene, 221: 25-34). The gene coding for the A3 domain of vWF (201aa) was amplified by PCR using the A3for (SEQ ID NO: 68) and A3back (SEQ ID NO: 69) PCR primers.

```
A3for:
CTG GTG CTG CAG AGG TGA AGC TTC GGA GAG GGG CTG

CAG ATC

A3back:
ATC CAT GCA AAT CCT CTA GAA TCC AGA GCA CAG TTT

GTG GAG
```

Fragment and vector were digested with HindIII and XbaI, ligated and transformed in UT5600 (=pBAD-vWFA1/pBAD-vWFA3). Transformed cells were plated on LB agar plates containing 20 µg/ml streptomycin, 50 µg/ml spectinomycin.

Figure 5:

The pBAD-vWFA3 plasmid was transformed in UT5600 F-cells and plated on LB agar plates with 20 µg/ml streptomycin, 50 µg/ml spectinomycin. A single colony was used to inoculate LB medium with 20 µg/ml streptomycin, 50 µg/ml spectinomycin. Cells were grown overnight at 37° C. at 200 rpm. The next day, cells were induced with 0.2% arabinose and incubated for 1 more hour at 37° C. at 150 rpm. Total cell lysates were boiled in reducing sample buffer, loaded on a 12% SDS-PAGE and transferred to nitrocellulose for Western blotting. Transferred proteins were detected using a monoclonal anti-Oprl antibody (SH2.2) (Cote-Sierra et al, 1998, Gene, 221: 25-34). An anti-mouse IgG conjugated with alkaline phosphatase was applied (Sigma), and the blots were developed with BCIP/NBT (FIG. 5). The pBAD-vWF-A3 plasmids were transformed in UT5600 F-cells and plated on LB agar plates with 20 µg/ml streptomycin, 50 µg/ml spectinomycin. A single colony was used to inoculate LB medium with 20 µg/ml streptomycin, 50 µg/ml spectinomycin. Cells were grown overnight at 37° C. at 200 rpm. The next day, cells were induced with 0.2% arabinose and incubated for 1 more hour at 37° C. at 150 rpm. A microtiter plate was coated overnight at 4° C. with the monoclonal anti-Oprl antibody (SH2.2) diluted 1/1000 in PBS and blocked for 2 hours at RT with PBS containing 1% casein. After induction, total cells were allowed to bind to the plate for 1 hour at room temperature. The plates were washed five times with PBS-Tween. Phage preparations of single colonies were allowed to bind for two hours at room temperature. The plates were washed five times with PBS-Tween. An anti-M13 HRP conjugate was used for detection of phage binding to E. coli cells expressing the A3 domain or to an irrelevant antigen on their surface. The plates were washed five times with PBS-Tween. Staining was performed with ABTS/$H_2O_2$ and signals were measured after 30 minutes at 405 nm. Results are summarized in Table 7.

Example 12: Bivalent and Bispecific VHHs: Expression and Purification

The E. coli production vector pAX11 was designed (FIG. 6), which allows the two-step cloning of bivalent or bispecific VHH.

The carboxy terminal VHH is cloned first with PstI and BstEII, while in the second step the other VHH is inserted by SfiI and NotI, which do not cut within the first gene fragment. The procedure avoids the enforcement of new sites by amplification and thus the risk of introducing PCR errors. The sequence is shown in Table 30 (SEQ ID numbers 8, 9, 10, 11 and 12).

Protein was expressed and purified as described in Example 6. An extra purification step was needed on superdex 75 for removal of some monovalent degradation product (5-10%). Yields obtained for 1 liter expression and purification of bivalent protein in E. coli are summarized in Table 8.

Example 13: Binding in ELISA to vWF

Binding to vWF was tested in ELISA as described in Example 7 and compared to binding of monovalent VHH. The results are shown in FIG. 7. It is clear from the results that bivalent and bispecific VHH show stronger binding to VWF when compared to monovalent VHH.

Example 14: Inhibition ELISA with Purified VHH

Inhibition for binding of vWF to collagen was tested for monovalent as compared to bivalent VHHs as described in Example 5. Instead of using purified vWF, human, baboon and pig plasma was used in parallel at a dilution of 1/60. IC50 values are summarized in Table 9.

Example 15: Stability of Bivalent or Bispecific Constructs in Human Plasma

Stability of bivalent constructs was tested by incubation at 37° C. in human plasma. AM-4-15-3/AM2-75 was incubated in human plasma at a concentration of 38 µg/ml at 37° C. A sample was removed after 1, 2, 3, 6 and 24 hours incubation. Samples were diluted 10-fold and analyzed by Western blot. Results are summarized in FIG. 8 and show that the bivalent construct is stable for at least 24 hours at 37° C. in human plasma.

Example 16: Evaluation of Inhibition by VHH at High Shear

Figure 9:
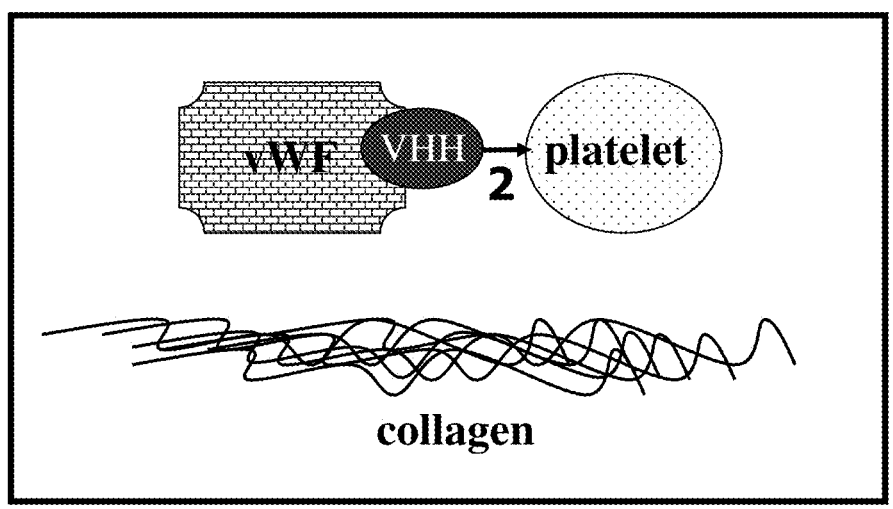

Glass coverslips (18×18 mm, Menzel Gläser) were cleaned overnight by a chromosulfuric acid (2% chromium trioxide) solution and rinsed with distilled water before spraying. Monomeric collagen type III was solubilized in 50 mmol/L acetic acid and sprayed with a density of 30 µg/cm² on glass coverslips with a retouching airbrush (Badger model 100, Badger Brush Co). After the spraying procedure, the collagen surface was blocked for 1 hour with 1% human albumin in PBS (10 mmol/L phosphate buffer, pH 7.4, and 0.15 mol/L NaCl) to prevent nonspecific protein binding during the subsequent perfusion. Perfusion studies over collagen type III were carried out in a specially devised small parallel-plate perfusion chamber with well-defined rheological characteristics accommodating a glass coverslip. Whole blood was obtained by venipuncture from volunteers. Blood was drawn through the perfusion chamber by a Harvard infusion pump (pump 22, model 2400-004; Harvard, Natick, Mass.). The perfusion time was 5 minutes. Triplicate coverslips were inserted in the chamber. Five milliliters of whole blood was pre-warmed at 37° C. for 5 minutes with or without addition of VHH, and then recirculated through the chamber for 5 minutes at a wall shear rate of 300 s$^{-1}$ or 1600 s$^{-1}$. The coverslips were removed, rinsed, fixed with 0.05% glutaraldehyde, dehydrated with methanol, and stained with May-Grünwald/Giemsa. Platelet adhesion was quantitated with a light microscope (1,000× magnification) connected to a computerized image analyzer (AMS 40-10, Saffron Walden, UK). Platelet adhesion was expressed as the percentage of the surface covered with platelets. Results are summarized in Table 10 and 11.
Selection of Binders for vWF Inhibiting the Interaction with Platelets (FIG. 9).

Example 17: Selection of Binders for vWF Inhibiting the Interaction with Platelets: Panning Immunotubes were coated with 2 µg/ml vWF or with PBS containing 1% casein. After overnight incubation at 4° C., the tubes were blocked with PBS containing 1% casein, for 3 hours at RT. 200 µl phages were added to the immunotubes with a final volume of 2 ml in PBS. After 2 hours incubation at RT, the immunotubes were washed 10× with PBS-Tween and 10× with PBS. Bound phages were eluted with 2 ml 0.2 M glycin buffer pH=2.4. Elutions were performed for 20 minutes at room temperature. Eluted phages were allowed to infect exponentially growing TG1 cells, and were then plated on LB agar plates containing 100 µg/ml ampicillin and 2% glucose. The results from the panning are presented in Table 12.

Example 18: Screening for Binding to the A1 Domain of vWF

The pBAD-Oprl-strep-spec vector was used to display the VWF A1 domain as a fusion with Oprl on the surface of UT5600 E. coli cells (F-ara-14 leuB6 azi-6 lacY1 proC14 tsx-67 entA403 trpE38 rfbD1 rpsL109 xyl-5 mtl-1 thi1 DompT fepC266) (Cote-Sierra et al, 1998, Gene, 221: 25-34). The gene coding for the A1 domain of vWF (219aa) was amplified by PCR using the A1 for (SEQ ID NO: 70) and A1 back (SEQ ID NO: 71) PCR primers.

```
A1for:
CCG GTG AGC CCC ACC ACT CTA AGC TTG GAG GAC ATC

TCG GAA CCG

A1back:
CCC CAG GGT CGA AAC CCT CTA GAG CCC CGG GCC CAC

AGT GAC
```

Figure 10:
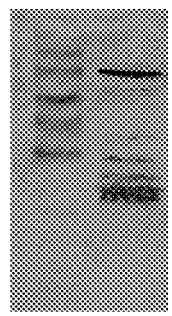

Fragment and vector were digested with HindIII and XbaI, ligated and transformed in UT5600 (=pBAD-vWFA1/pBAD-vWFA3). Transformed cells were plated on LB agar plates containing 20 µg/ml streptomycin, 50 µg/ml spectinomycin.
The pBAD-vWFA1 plasmid was transformed in UT5600 F-cells and plated on LB agar plates with 20 µg/ml streptomycin, 50 µg/ml spectinomycin. A single colony was used to inoculate LB medium with 20 µg/ml streptomycin, 50 µg/ml spectinomycin. Cells were grown overnight at 37° C. at 200 rpm. The next day, cells were induced with 0.2% arabinose and incubated for 1 more hour at 37° C. at 150 rpm. Total cell lysates were boiled in reducing sample buffer, loaded on a 12% SDS-PAGE and transferred to nitrocellulose for Western blotting. Transferred proteins were detected using a monoclonal anti-Oprl antibody (SH2.2) (Cote-Sierra et al, 1998, Gene, 221: 25-34). An anti-mouse IgG conjugated with alkaline phosphatase was applied (Sigma), and the blots were developed with BCIP/NBT as shown in FIG. 10.
The ELISA was performed as described in Example 11. Results are summarized in Table 13. The results indicate that vWF-A1 domain-specific VHH are obtained.

Example 19: Selection of Binders for vWF Inhibiting the Interaction with Platelets: MATCHM E. coli cells expressing the A1 domain of vWF (Example 18) were used for a MATCHM experiment: UT5600 cells transformed with pBAD-Oprl-A1 were grown and induced with 0.2% arabinose. Cells were washed and incubated with the phages for 1 hour at RT. This mixture was washed 7 times with PBS-Tween and phages were eluted with exponentially growing TG1 cells. We performed a first and a second round of selection. Results are summarized in Table 14.

Example 20: ELISA: Binding to vWF of Purified VHH

Figure 11:
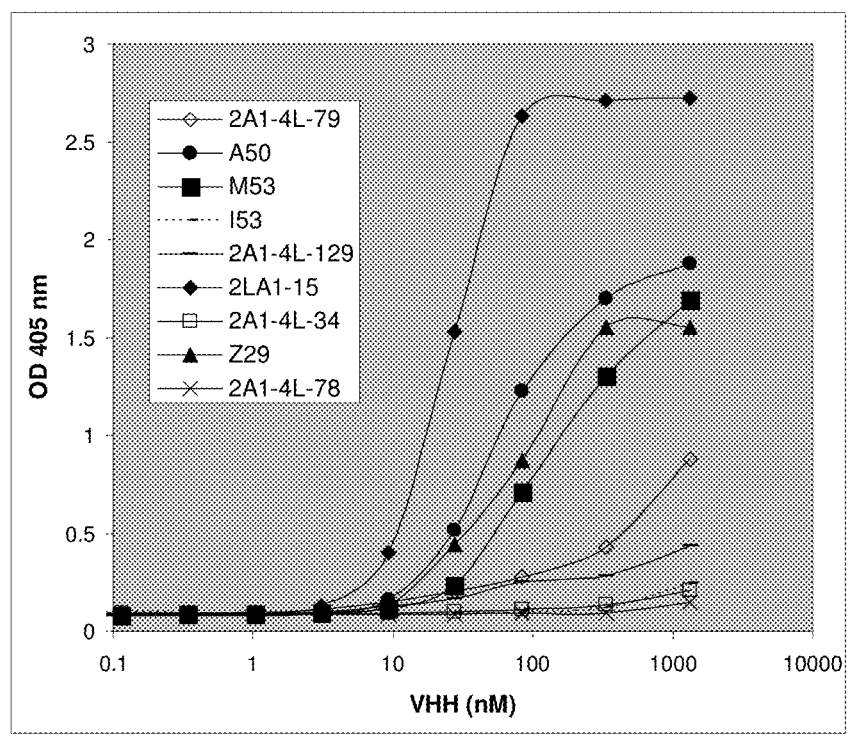

VHH specific for the A1 domain of vWF were expressed and purified as described in Example 6. Binding in ELISA to vWF was measured as described in Example 7. Results are shown in FIG. 11.

Example 21: Inhibition ELISA with Purified VHH

A microtiter plate was coated overnight at 4° C. with an antibody specific for platelet receptor gpIb at 5 µg/ml in PBS. The plate was washed five times with PBS-Tween, and blocked with 300 µl PBS-1% casein for 2 hours at room temperature. The plate was washed 3 times with PBS-Tween. Platelet receptor gpIb (gpIb) was applied to the wells of the microtiter plate at a concentration of 1 µg/ml and allowed to bind for 2 hours at room temperature. The plate was washed five times with PBS-Tween. VHH (A38 (negative control) and A50 (vWF A1 binder)) was added at decreasing concentration. Plasma containing vWF was pre-incubated at a dilution of 1/128 at 37° C. for 5 minutes. Risto was added at a final concentration of 760 µg/ml and added to the VHH. This mixture was incubated for 30 minutes at room temperature. 100 µl of this mixture was then applied to a microtiter plate well and incubated for 90 minutes at room temperature. The plate was washed five times with PBS-Tween. A anti-vWF-HRP monoclonal antibody was diluted 3.000-fold in PBS and incubated for 1 hour. The plate was washed five times with PBS-tween and vWF-binding was detected with ABTS/$H_2O_2$. Signals were measured after 30 minutes at 405 nm. Results are summarized in FIG. 12.

Example 22: Sequencing of the Clones

Clones were sequenced with M13 universal reverse primer. Amino acid sequences are shown in Table 30 (SEQ ID numbers 23, 24, 25, 26, 27, 28, 29, 30 and 31).

Example 23: Evaluate Inhibition by VHH at High Shear

Shear experiments were performed as described in Example 16. Platelet adhesion was expressed as the percentage of the surface covered with platelets. Results are summarized in Table 15 and 16.

Example 24: Bivalent VHHs: Expression and Purification

Bivalent molecules were constructed as described in Example 12. The sequence is shown in Table 30 (SEQ ID numbers 32, 33 and 34).

Protein was expressed and purified as described in Example 6. An extra purification step was needed on superdex 75 for removal of some monovalent degradation product (5-10%).

Example 25: Evaluate Inhibition by VHH at High Shear

Shear experiments were performed as described in Example 16. Platelet adhesion was expressed as the percentage of the surface covered with platelets. Results are summarized in Table 17 and 18.

Figure 13:
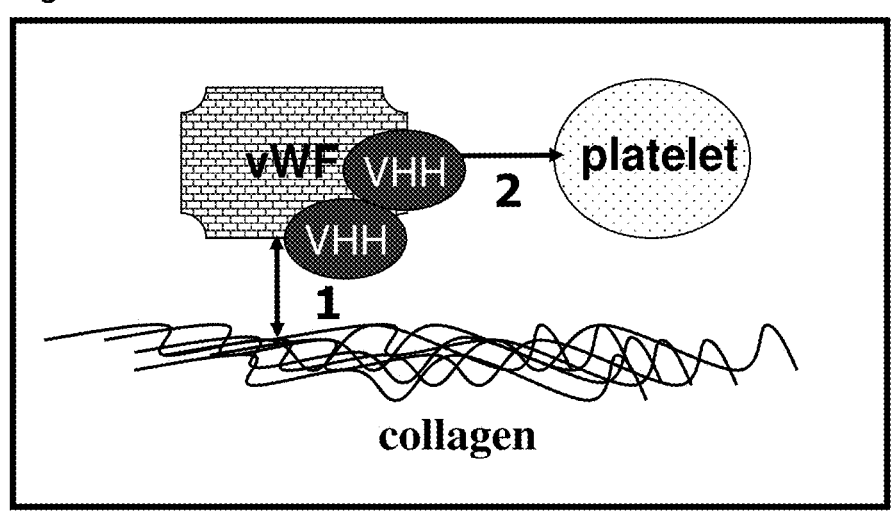

Make Bispecific Constructs for vWF-Specific VHH (FIG. 13)

Example 26: Construction and Sequence of Bispecific Constructs

Constructs were made as described in Example 12, with one VHH specific for vWF and inhibiting the interaction with collagen, and the second VHH also specific for vWF but inhibiting the interaction with platelet receptor gpIb. Sequences are shown in Table 30 (SEQ ID NOs: 20, 21 and 22)

Example 27: Expression and Purification of Bispecific Constructs

Protein was expressed and purified as described in Example 6. A extra purification step was needed on superdex 75 for removal of some monovalent degradation product (5-10%). Yields obtained for 1 liter expression and purification of bispecific protein in *E. coli* are summarized in Table 19.

Example 28: Binding to vWF

Figure 14:
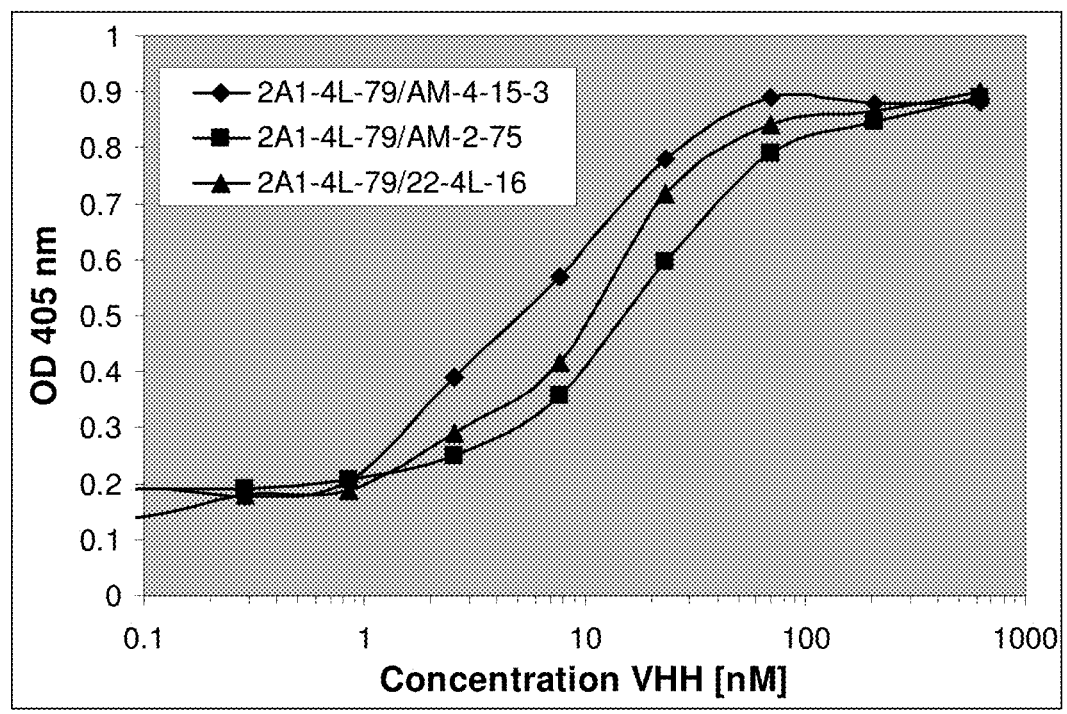

Binding to vWF was tested in ELISA as described in example 7. Results are shown in FIG. 14.

Example 29: Inhibition of Binding of vWF to Collagen by the Bispecific Constructs as Compared to the Monovalent VHHs Inhibition for binding of vWF to collagen was tested for monovalent as compared to bispecific constructs as described in example 5. IC50 values are summarized in Table 20.

Example 30: Evaluate Inhibition by VHH at High Shear

Shear experiments were performed as described in Example 16. Platelet adhesion was expressed as the percentage of the surface covered with platelets. Results are summarized in Table 21 and 22.

Figure 15:
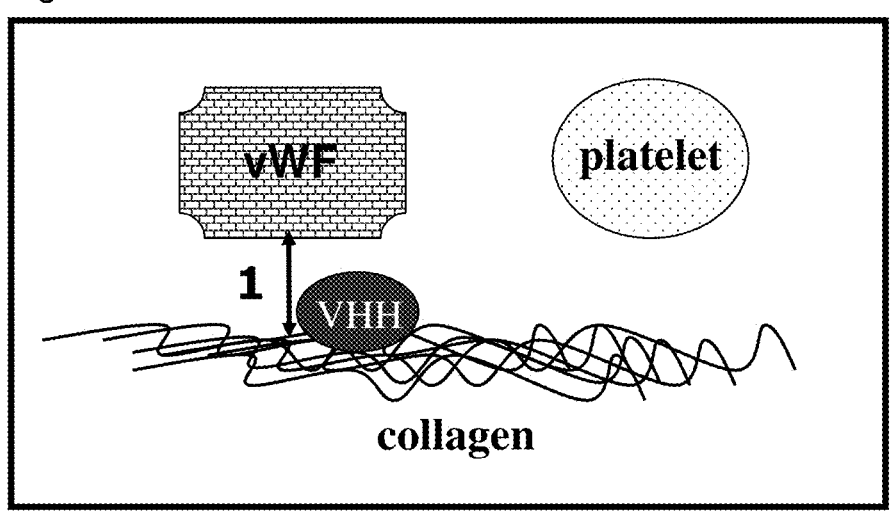

Screening for Binders for Collagen Type I and Type III (FIG. 15)

Example 31: Selection of Binders for Collagen Type I

A microtiterplate was coated with 25 µg/ml collagen type I. Phages were prepared as described in Example 3 and allowed to bind to the well of a microtiterplate that was blocked for 2 hours. After washing, phages were eluted with 0.1 M glycin buffer pH=4.5. Results are summarized in Table 23.

Example 32: Test VHH in ELISA for Binding to Collagen Type I and Type III

Clones were tested for binding in ELISA as described in example 7 but then on collagen type I or type III coated wells at 25 µg/ml in PBS. The results are summarized in Table 24.

Example 33: Sequencing of the Clones

Clones were sequenced with M13 universal reverse primer. Amino acid sequences are shown in Table 30 (SEQ ID numbers 35, 36 and 37).

Example 34: Binding of Purified VHH to Collagen Type I and Type III

VHH were expressed and purified as described in Example 6. A microtiterplate was coated with 25 µg/ml collagen typeI or typeIII and blocked. Binders were applied in duplo dilutions and binding was detected as described in Example 7. Results are summarized in FIG. 16.

Example 35: Selection of Binders for Collagen Type I Inhibiting the Interaction with vWF A microtiterplate was coated with 25 µg/ml collagen type I. Phages were prepared as described in Example 3 and allowed to bind to the well of a microtiterplate that was blocked for 2 hours. After washing, phages were eluted with 300 µg/ml vWF. A second and third round of selection were performed in the same way.

Example 36: Test VHH in ELISA for Binding to Collagen Type I and Type III

Clones were tested for binding to collagen type I and type III in ELISA as described in Example 34.

Example 37: Sequencing of the Clones

Clones were sequenced with M13 universal reverse primer.

Example 38: Binding of Purified VHH to Collagen Type I and Type III

VHH were expressed and purified as described in example 6. A microtiterplate was coated with 25 µg/ml collagen typeI or typeIII and blocked. Binders were applied in duplo dilutions and binding was detected as described in Example 34.

Example 39: Test Inhibition of Binding of vWF to Collagen by Collagen-Specific VHH in ELISA Inhibition was tested as described in Example 5.

Example 40: Test Inhibition of Platelet Aggregation by Collagen-Specific VHH at Low and at High Shear Shear experiments were performed as described in Example 16. Platelet adhesion was expressed as the percentage of the surface covered with platelets.
Improved Half-Life of VHH Example 41: Immunization of Llamas One llama was immunized with human serum albumin (HSA). The immunization scheme is summarized in Table 25.

Example 42: Repertoire Cloning

The library was prepared as described in Example 2. The size of the library was $2 \times 10^7$ cfu, and all clones contained insert of the correct size.

Example 43: Rescue of the Library, Phage Preparation

Phages were prepared as described in Example 3.

Example 44: Phage ELISA

Figure 17:
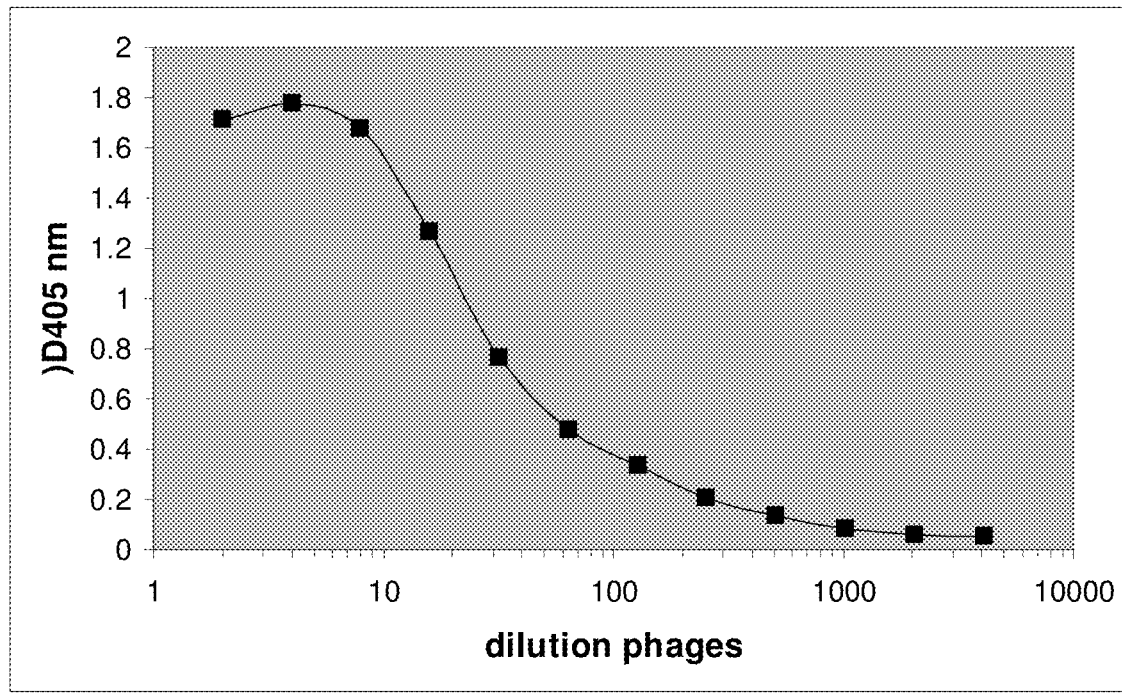

A microtiter plate (Maxisorp) was coated overnight at 4° C. with PBS-1% casein or with 5 µg/ml HSA (human serum albumin). The plate was washed 3 times with PBS-Tween (0.05% Tween20) and blocked for 2 hours at room temperature with 200 µl PBS-1% casein. The plate was washed five times with PBS-Tween. Phages were prepared as described above and applied to the wells in consecutive twofold dilutions. Plates were washed five times with PBS-Tween. Bound phage were detected with a mouse monoclonal antibody anti-M13 conjugated with horse radish peroxidase (HRP) diluted 1/2000 in PBS. The plates were washed five times with PBS-Tween. Staining was performed with ABTS/$H_2O_2$ and signals were measured after 30 minutes at 405 nm. Results are shown in FIG. 17 and indicate the presence of HSA-specific nanobodies in the library.

Example 45: Selection: First and Second Round of Biopanning

A well in a microtiterplate was coated with 10 µg/ml mouse serum albumin (MSA), or with PBS containing 1% casein. After overnight incubation at 4° C., the wells were blocked with PBS containing 1% casein, for 3 hours at RT. 200 µl phages was added to the wells. After 2 hours incubation at RT, the wells were washed 10× with PBS-Tween and 10× with PBS. Bound phages were eluted with 100 µl 0.2 M glycin buffer pH=2.4. Elutions were performed for 20 minutes at room temperature. Eluted phages were allowed to infect exponentially growing *E. coli* TG1 cells, and were then plated on LB agar plates containing 100 µg/ml ampicillin and 2% glucose. A second round was performed with the same conditions as described above. Results are summarized in Table 26.

Example 46: Screening of Individual Clones after Biopanning

ELISA: Binding to Human Serum Albumin (HSA) and Mouse Serum Albumin (MSA)

Periplasmic extract was prepared as described in Example 6.

A microtiter plate was coated with 5 µg/ml HSA, with 5 µg/ml mouse serum albumin (MSA) or with PBS-1% casein, overnight at 4° C. Plates were blocked for two hours at room temperature with 300 µl 1% casein in PBS. The plates were washed three times with PBS-Tween. Periplasmic fraction was prepared for 23 individual clones after the first and second round of selection, and allowed to bind to the wells of the microtiterplate. Plates were washed six times with PBS-Tween, after which binding of nanobody was detected by incubation with mouse anti-Histidine monoclonal antibody Serotec MCA 1396 (1/1000 dilution) in PBS for 1 hour at RT followed by anti-mouse-alkaline phosphatase conjugate 1/2000 in PBS, also for 1 hour at RT. Staining was performed with the substrate PNPP (p-nitrophenyl-phosphate, 2 mg/ml in 1M diethanolamine, 1 mM $Mg_2SO_4$, pH9.8) and the signals were measured after 30 minutes at 405 nm. Results are summarized in Table 27.

Example 47: HinfI Pattern and Sequencing

A PCR was performed on positive clones after the second round of panning, with a set of primers binding to a sequence in the vector. The PCR product was digested with the restriction enzyme HinfI and loaded on a agarose gel. 4 clones were selected with a different HinfI-pattern for further evaluation. Those clones were sequenced, and results are summarized in Table 30 (SEQ ID numbers 16, 17, 18 and 19).

Example 48: Test Cross-Reactivity with Albumin of Different Species

Figure 18:
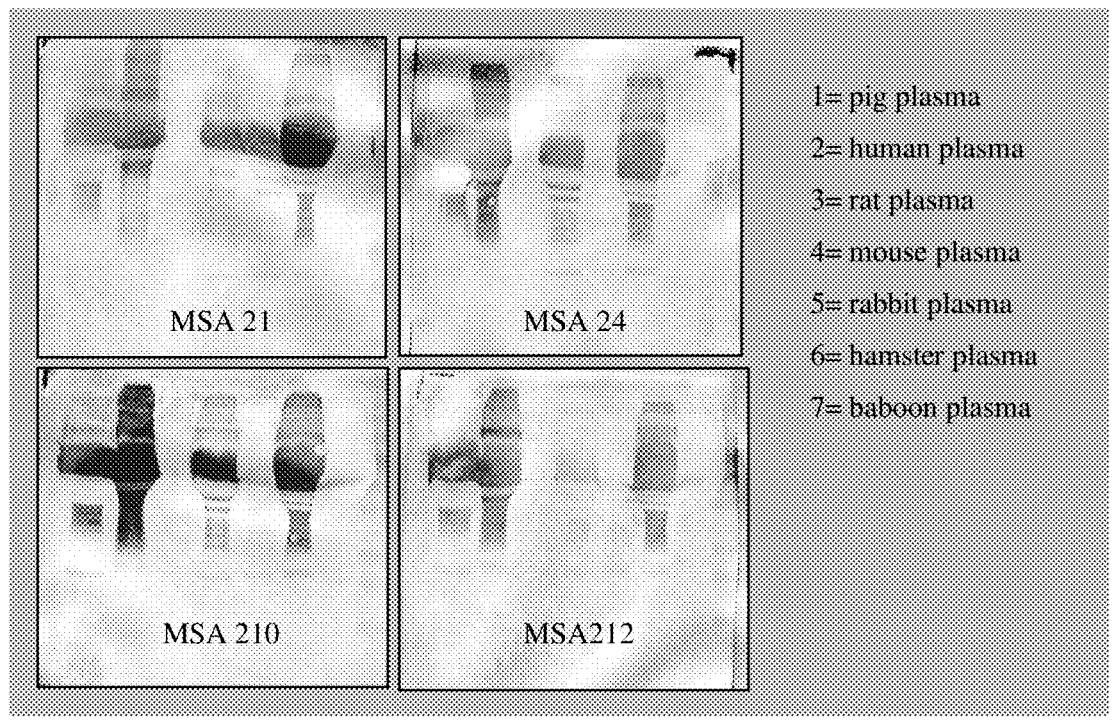

A SDS-PAGE was run for plasma (1/10 dilution) from different species (baboon, pig, hamster, human, rat. mouse and rabbit) and blotted on a nitrocellulose membrane. Phages were prepared for clones MSA 21. MSA 24, MSA 210, MSA212 and a irrelevant nanobody as described in Example 3. Phages were allowed to bind to the nitrocellulose blotted serum albumins and unbound phages were washed away. Binding was detected with a anti-M13 polyclonal antibody coupled to HRP. DAP was used as a substrate for detection. Results are shown in FIG. 18.

From these results we can conclude that all 4 binders are cross-reactive between pig, human, mouse (less for MSA212) and hamster serum albumin. MSA 21 is also cross-reactive with rabbit serum albumin. With the irrelevant nanobody no binding was observed (not shown).

As a control experiment, a SDS-PAGE was run with the different plasma samples diluted 1/100 in PBS. The gel was stained with coomassie. We can conclude from FIG. 19 that albumin levels in all plasma samples are high except for rabbit plasma, with low levels of albumin.

Example 49: Expression and Purification

Protein was expressed and purified as described in Example 6.

Example 50: ELISA on MSA of the Purified Nanobodies

Figure 20:
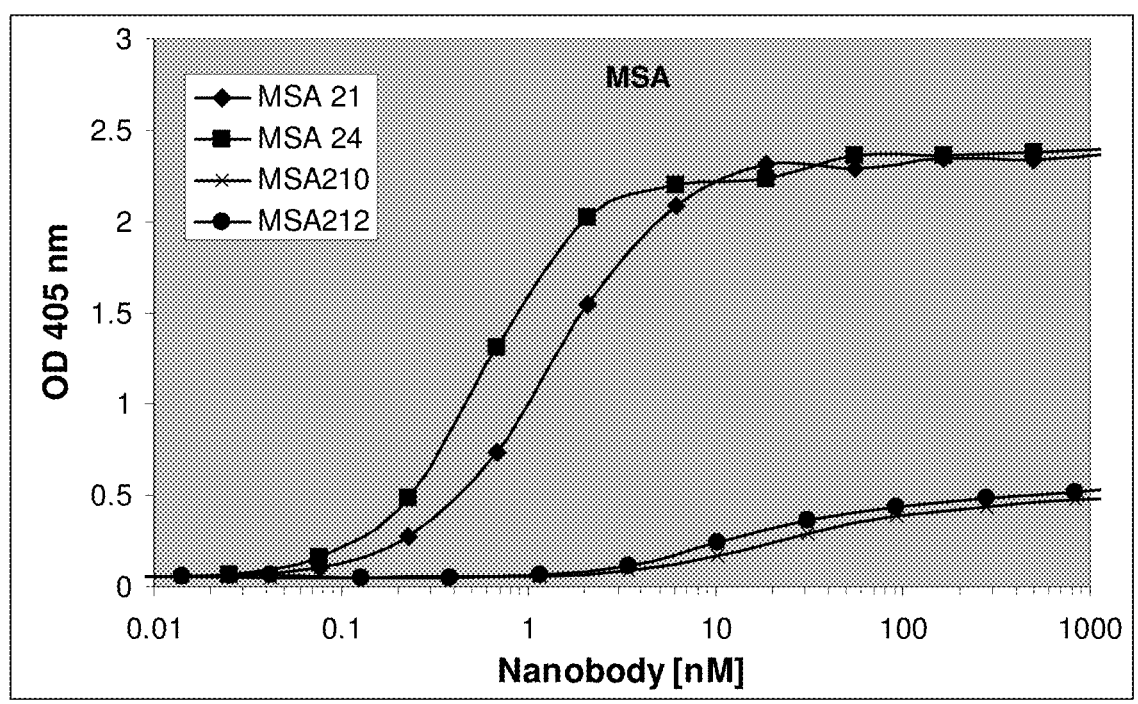

A microtiterplate was coated with 5 µg/ml MSA overnight at 4 C. After washing, the plate was blocked for 2 hours at RT with PBS-1% casein. Samples were applied in duplicate starting at a concentration of 2500 nM at 1/3 dilutions and allowed to bind for 2 hours at RT. A polyclonal rabbit anti-nanobody serum was added at 1/1000 (K208) for one hour at RT. Detection was with anti-rabbit alkaline phosphatase conjugate at 1/1000 and staining with PNPP. Results are shown in FIG. 20.

Example 51: Construction and Sequence of Bispecific Constructs

Figure 21:
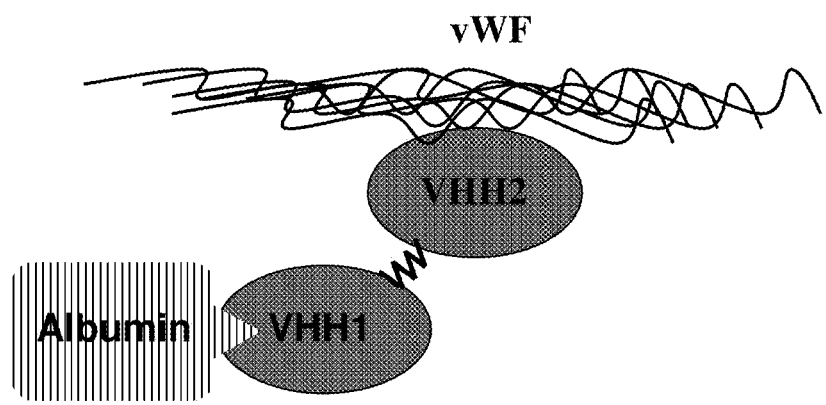

Bispecific constructs were prepared with the first VHH specific for albumin (MSA21) and the second VHH specific for vWF (FIG. 21). Constructs were made as described in Example 12. Sequences are shown in Table 30 (SEQ ID numbers 13, 14 and 15)

Example 52: Expression and Purification of Bispecific Constructs

Protein was expressed and purified as described in Example 6. A extra purification step was needed on superdex 75 for removal of some monovalent degradation product (5-10%).

Example 53: Functionality of Both VHHs in the Bispecific Construct

Figure 22:
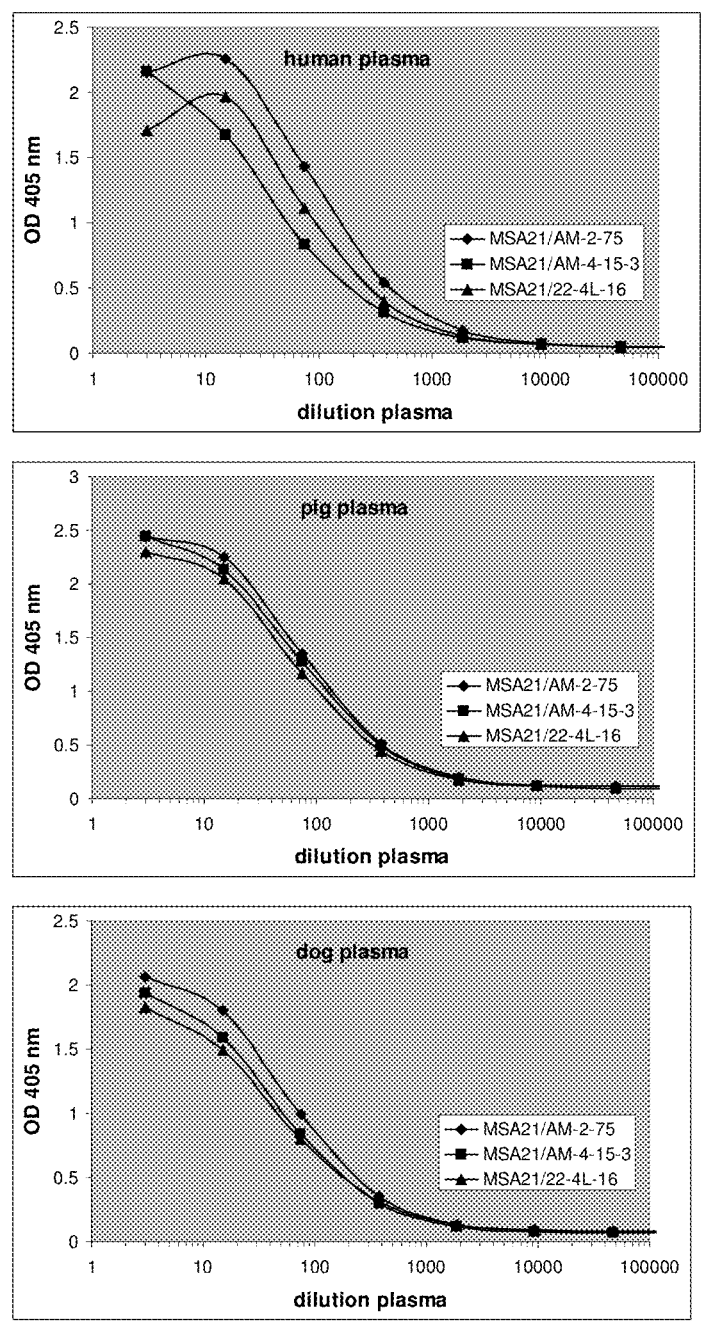

A microtiterplate was coated with 5 µg/ml mouse serum albumin overnight at 4° C. After washing the plate, wells were blocked for 2 hours with PBS-1% casein. The bispecific proteins were allowed to bind to the wells for 2 hours at RT. After washing, human, dog and pig plasma was added at different dilutions and allowed to bind for 2 hours at RT. Binding of vWF was detected with anti-vWF-HRP from DAKO at 1/3000 dilution. Staining was performed with ABTS/$H_2O_2$. Results are shown in FIG. 22 and indicate that functionality of both VHHs is retained in the bispecific construct.

Example 54: Inhibition of Binding of vWF to Collagen by the Bispecific Constructs as Compared to the Monovalent VHHs Inhibition for binding of vWF to collagen was tested for monovalent as compared to bispecific constructs as described in Example 5. IC50 values are summarized in Table 28. Results indicate that the inhibitory properties of the VHH are retained in the bispecific construct.
Selection of Binders for gpIb Inhibiting the Interaction with vWF (FIG. 23)
Immunization, repertoire cloning and phage preparation were performed as described in Examples 1, 2, 3.

Example 55: Selection of Binders for rgpIb

A microtiterplate was coated with a mouse mAb against rgpIb. The plate was blocked and rgpIb was allowed to bind for 2 hours at RT at 5 µg/ml. The plate was washed. Phages were prepared as described above and allowed to bind to the wells of the microtiterplate. After washing, phages were eluted with 0.1 M glycin buffer pH=4.5. A second round of panning was performed in the same way.

Example 56: Screening for Binders in ELISA

Periplasmic extract was prepared as described in Example 6.
The supernatant was applied to wells coated with mAb and subsequently gpIb, as described in Example 55. Dilution series of all purified samples were incubated for 2 hours at RT. Plates were washed six times with PBS-Tween, after which binding of VHH was detected by incubation with mouse anti-His-HRP mAB 1/2000 in PBS for 1 hour at RT followed by staining with the substrate ABTS/$H_2O_2$. The signals were measured after 30 minutes at 405 nm.

Example 57: Binding of Purified VHH to rgpIb

Periplasmic fraction was prepared as described in Example 6. The supernatant containing the VHH was loaded on Ni-NTA and purified to homogeneity. The yield of VHH was calculated according to the extinction coefficient. ELISA was performed as described in Example 55.

Example 58: Sequencing of the Clones

Clones were sequenced with M13 universal reverse primer.

Example 59: Test Inhibitory Properties of VHHs Specific for gpIb

VHHs were tested for inhibition in ELISA as described in Example 21.

Example 60: Evaluate Inhibition by VHH at High Shear

Shear experiments were performed as described in Example 16. Platelet adhesion was expressed as the percentage of the surface covered with platelets.
Coating of Stents, Tubing, Balloons, Catheters, Transplantation Material with VHH

Example 61: Stability of VHH

VHH C37 was incubated at 37° C. and inhibition of binding of vWF to collagen was measured at different time points by ELISA as described in Example 7. Results were compared to VHH stored at −20° C. and are presented in FIG. 24. Shown for comparison are the activities of a scFv against B3 antigen (Reiter et al, Protein Engineering, 1994, 7: 697-704), and said scFv modified by the introduction of a disulphide bond between framework residues 44 and 105 to enhance its stability (dsFv). The dsFv lost 40% of its activity after 60 hours incubation at 37° C. After one year of incubation at 37° C., C37 was analyzed for its inhibitory properties as compared to C37 stored in the freezer. The ELISA was performed as described in Example 5 with human plasma at a final dilution of 1/200. The results are shown in FIG. 25 and indicate that functionality is fully retained (IC50 value of 0.085 versus 0.1 µg/ml for C37 stored at 37° C. versus −20° C.). Therefore, it is expected that VHH will have a long shelf-life.

Example 62: VHH Immobilized in a Polymer

Figures 26, 27:
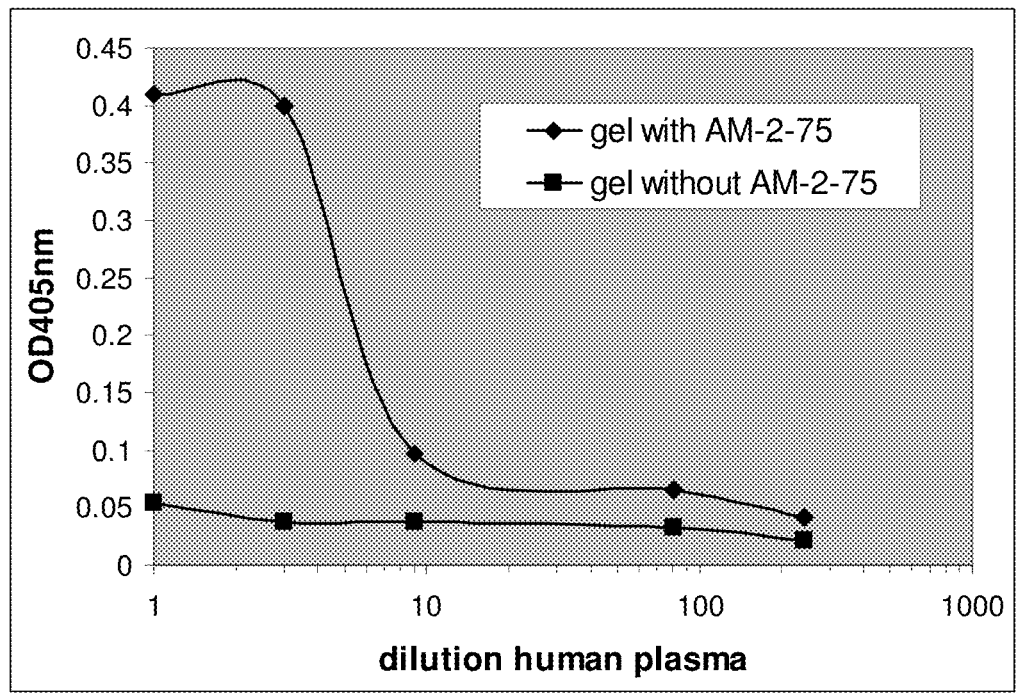

A mixture was prepared of 0.5 ml of 30% acrylamide; 1 ml of 1M Tris pH=7.5; 3.5 ml H2O; 35 µl of 10% APS; 3.5

µl TEMED. In some wells, VHH C37 was added at a final concentration of 10 µg/ml. The mixture was allowed to polymerize in the wells of a 96-well plate for 3 hours at RT. Human plasma was added at different dilutions starting with undiluted plasma. After 1 hour incubation at RT, the plate was washed and anti-vWF-HRP (DAKO) was added at 1/2000, for 1 hour at RT. After washing the plate, substrate (ABTS/$H_2O_2$) was added and OD405 nm was measured. The result is shown in FIG. 26. The results indicate that VHH remain functional upon immobilization in a polymer.

Humanisation of C37

Example 63: Alignment of C37 with DP-47

Alignment of the C37 nanobody (SEQ ID NO: 1) and a human VH3 germline (DP-47) revealed a high degree of homology:

4 AA changes in FR1 on position 1, 5, 28 and 30
4 AA changes in FR3 on position 74, 75, 84 and 94
3 AA changes in FR4 on position 104, 108 and 111
as is shown in FIG. 27

Example 64: Mutagenesis of C37

C37 was mutated by using a non-PCR based site-directed mutagenesis method as described by Chen and Ruffner (Chen and Ruffner, Amplification of closed circular DNA in vitro, Nucleic Acids Research, 1998, 1126-1127) and commercialized by Stratagene (Quickchange site-directed mutagenesis).

Plasmid DNA was used as template in combination with 2 mutagenic primers (table 29) introducing the desired mutation(s). The 2 primers are each complementary to opposite strands of the template plasmid DNA. In a polymerase reaction using the Pfu DNA polymerase each strand is extended from the primer sequence during a cycling program using a limited amount of cycles. This results in a mixture of wild type and mutated strands. Digestion with Dpnl results in selection of mutated in vitro synthesized DNA. The DNA was precipitated and transformed to E. coli and analyzed for the required mutation by sequence analysis. The clone with the correct sequence was named C37-hum, the amino acid sequence is in Table 30 SEQ ID NO: 2.

Figure 28:
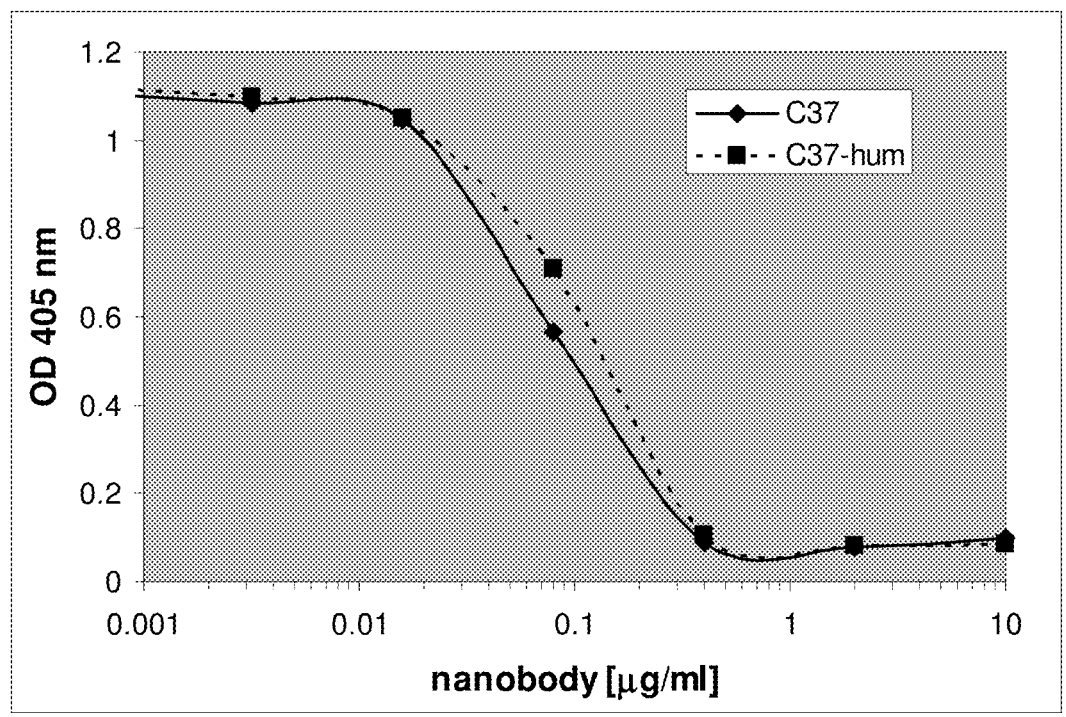

Expression and purification of C37-hum was performed as described in Example 6. Inhibition of binding of vWF to collagen for C37 was compared to C37-hum as described in Example 5. Results are shown in FIG. 28. It clearly shows that the humanized version of C37 remains fully functional.

The positions that still need to be humanized are: Q1, Q5, D104, Q108 and I111. We can humanize position 1 and 5 without loss of inhibition since these amino acids were introduced by the FR1 primer and do not occur naturally in the llama sequence. We can also humanize position 111 since we isolated a VHH identical to C37 except for I111V (AM-2-75 SEQ ID number 3) with the same functional characteristics (Example 9 and Table 6).

Position 108 is solvent exposed in camelid VHH, while in human antibodies this position is buried at the VH-VL interface (Spinelli, 1996; Nieba, 1997). In isolated VHs position 108 is solvent exposed. The introduction of a non-polar hydrophobic Leu instead of polar uncharged Gln can have a drastic effect on the intrinsic foldability/stability of the molecule.

Fragments of anti-VWF VHHs

Example 65: Expression of a VHH-CDR3 Fragment of vWF-C37

The CDR3 region of C37 was amplified by using a sense primer located in the framework 4 region (Forward: CCCCTGGTCCCAGTTCCCTC; SEQ ID NO: 72) and an anti-sense primer located in the framework 3 region (Reverse: TGTGCTCGCGGGGCCGGTAC; SEQ ID NO: 73).

In order to clone the CDR-3 fragment in pAX10, a second round PCR amplification was performed with following primers introducing the required restriction sites:

```
Reverse primer Sfi1 (SEQ ID NO: 74):
GTCCTCGCAACTGCGGCCCAGCCGGCCTGTGCTCGCGGGGCCGGTAC Forward primer Not1 (SEQ ID NO: 75):
GTCCTCGCAACTGCGCGGCCGCCCCCTGGTCCCAGTTCCCTC
```

The PCR reactions were performed in 50 ml reaction volume using 50 pmol of each primer. The reaction conditions for the primary PCR were 11 min at 94° C., followed by 30/60/120 sec at 94/55/72° C. for 30 cycles, and 5 min at 72° C. All reaction were performed with 2.5 mM MgCl2, 200 mM dNTP and 1.25 U AmpliTaq God DNA Polymerase (Roche Diagnostics, Brussels, Belgium).

After cleavage with Sfi1 and Not1 the PCR product was cloned in pAX10.

Isolation of Conformation-Specific Anti-vWF VHH's

Example 66: Selection Via First and Second Round Biopanning on Recombinant A1 (rA1)

A well in a microtiter plate was coated with 5 µg/ml recombinant A1 domain of vWF (rA1), or with PBS containing 1% casein. After overnight incubation at 4° C., the wells were blocked with PBS containing 1% casein, for 3 hours at RT. 200 µl phages was added to the wells. After 2 hours incubation at RT, the wells were washed 10× with PBS-Tween and 10× with PBS. Bound phages were eluted with 100 µl 0.2 M glycin buffer, pH 2.4. Elutions were performed for 20 minutes at room temperature. Eluted phages were allowed to infect exponentially growing E. coli TG1 cells, and were then plated on LB agar plates containing 100 µg/ml ampicillin and 2% glucose. A second round was performed with the same conditions as described above but phages were re-suspended in 10 µg/ml vWF. The wells of the microtiterplate were washed 7 times for 30 minutes with 10 µg/ml vWF. Results are summarized in Table 31.

Example 67: Screening of Individual Clones after Biopanning

ELISA: Binding to rA1 and vWF

A single colony was used to start an overnight culture in LB containing 2% glucose and 100 µg/ml ampicillin. This overnight culture was diluted 100-fold in TB medium containing 100 µg/ml ampicillin, and incubated at 37° C. until OD600 nm=0.5. 1 mM IPTG was added and the culture was incubated for 3 more hours at 37° C. or overnight at 28° C. Cultures were centrifuged for 20 minutes at 10,000 rpm at 4° C. The pellet was frozen overnight or for 1 hour at −20° C. Next, the pellet was thawed at room temperature for 40 minutes, re-suspended in PBS and shaken on ice for 1 hour. Periplasmic fraction was isolated by centrifugation for 20 minutes at 4° C. at 20.000 rpm. The supernatant containing the VHH was used for further analysis.

A microtiter plate was coated with 2 µg/ml rA1 or with 1 µg/ml vWF, overnight at 4° C. Plates were blocked for two hours at room temperature with 300 µl 1% casein in PBS. The plates were washed three times with PBS-Tween. Periplasmic fraction was prepared for 192 individual clones after the second round of selection, and allowed to bind to the wells of the microtiter plate. Plates were washed six times with PBS-Tween, after which binding of nanobody was detected by incubation with rabbit polyclonal anti-nanobody (1/2000 dilution) in PBS for 1 hour at RT followed by goat anti-rabbit-HRP conjugate 1/2000 in PBS, also for 1 hour at RT. Staining was performed with the substrate ABTS/H2O2 and the signals were measured after 30 minutes at 405 nm. Results are summarized in Table 32. We can conclude that 50 clones bind to rA1 and not to vWF.

Example 68: HinfI Pattern and Sequencing

Figure 29:
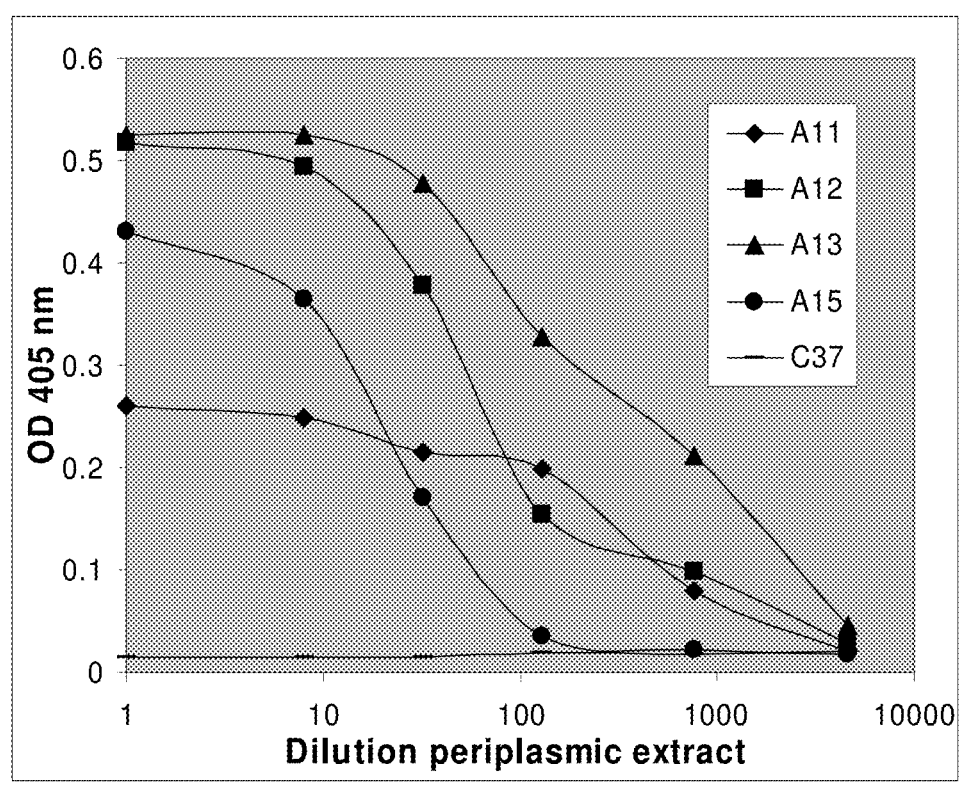

A PCR was performed on positive clones for rA1 and negative for vWF, after the second round of panning, with a set of primers binding to a sequence in the vector. The PCR product was digested with the restriction enzyme HinfI and loaded on a agarose gel. 30 clones were selected with a different HinfI-pattern for further evaluation. Those clones were tested in more detail by ELISA as described in example 67. Out of the 30 clones, 4 were shown to clearly have a much higher affinity for rA1 than for vWF. The data are shown in FIG. 29 (binding to rA1) and 30 (binding to vWF). These clones were sequenced, and results are summarized in Table 30 (SEQ ID numbers 62 to 65).

Example 69: Inhibition ELISA

Inhibition by nanobodies for binding of vWF to gpIb was determined by ELISA. A microtiter plate was coated overnight at 4° C. with an antibody specific for platelet receptor gpIb at 5 µg/ml in PBS. The plate was washed five times with PBS-Tween, and blocked with 300 µl PBS-1% casein for 2 hours at room temperature. The plate was washed 3 times with PBS-Tween. Plasma was applied to the wells of the microtiter plate at a 1/2 dilution and allowed to bind for 1.5 hours at 37 C. The plate was washed five times with PBS-Tween. VHH was added at decreasing concentration. Plasma containing vWF was pre-incubated at a dilution of 1/50 at 37° C. for 5 minutes. Ristocetin was added at a final concentration of 1 mg/ml and added to the VHH. This mixture was incubated for 1 hour 37 C. 50 µl of this mixture was then applied to a microtiter plate well and incubated for 90 minutes at 37 C. The plate was washed five times with PBS-Tween. An anti-vWF-HRP monoclonal antibody was diluted 3,000-fold in PBS and incubated for 1 hour. The plate was washed five times with PBS-tween and vWF-binding was detected with ABTS/H2O2. Signals were measured after 30 minutes at 405 nm.

FIGURES

FIG. 1. Interactions involved in the first steps of platelet aggregation.

FIG. 2. Interactions involved in the first steps of platelet aggregation. A VHH is indicated inhibiting the interaction between vWF and collagen.

FIG. 3. Binding to vWF as determined by ELISA, by purified VHH as described in Example 7.

FIG. 4. ELISA to test inhibition by VHH of binding of vWF to collagen as described in Example 9.

FIG. 5. Western blot showing expression of A3 domain of vWF as a fusion with Oprl on the surface of E. coli as described in Example 11.

FIG. 6. Restriction map of multiple cloning site of PAX011 for construction of bivalent or bispecific nanobodies.

FIG. 7. Binding in ELISA to purified vWF, for monovalent versus bivalent and bispecific VHH as described in Example 13.

Figure 8:
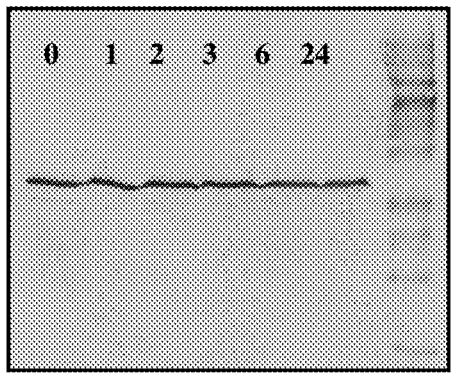

FIG. 8. Stability of bispecifc VHH in human plasma upon incubation at 37° C. for up to 24 hours as described in Example 15.

FIG. 9. Interactions involved in the first steps of platelet aggregation. A VHH is indicated inhibiting the interaction between vWF and platelets.

FIG. 10. Western blot showing expression of A1 domain of vWF as a fusion with Oprl on the surface of E. coli as described in Example 18.

FIG. 11. Binding to vWF as determined by ELISA, by purified VHH as described in Example 20.

Figure 12:
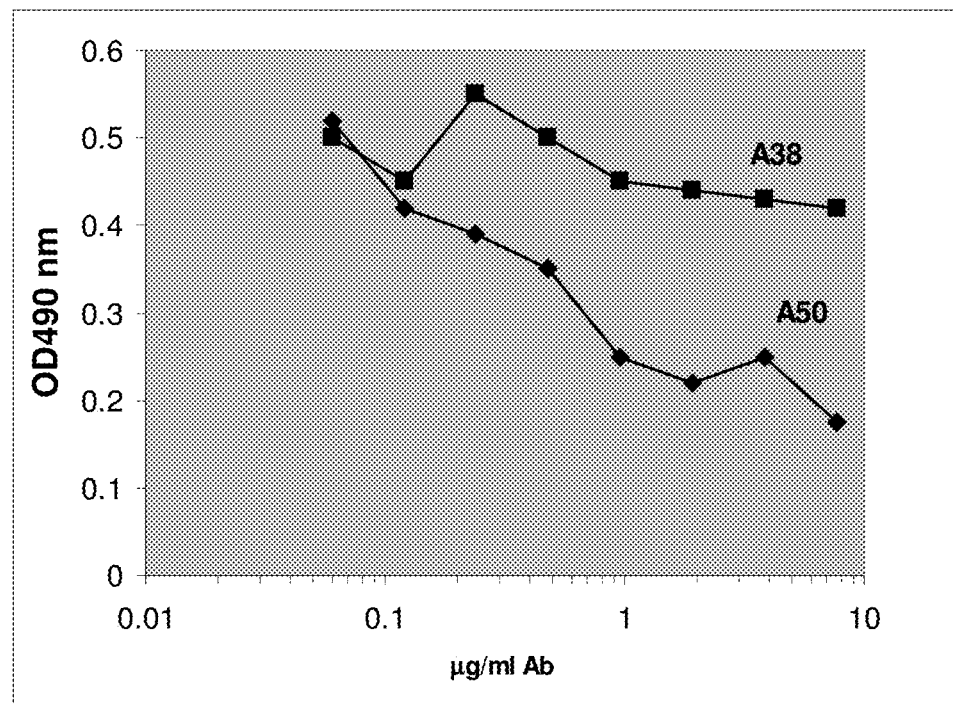

FIG. 12. Inhibition of binding of gpIb to VWF by A50 and A38 (negative control) as described in Example 21.

FIG. 13. Interactions involved in the first steps of platelet aggregation. A bispecific constructs is indicated with one VHH specific for vWF and inhibiting the interaction between vWF and collagen and the second VHH specific for vWF but inhibiting the interaction between vWF and platelets.

FIG. 14. Binding in ELISA to vWF as described in Example 28.

FIG. 15. Interactions involved in the first steps of platelet aggregation. A VHH is indicated specific for collagen and inhibiting the interaction between vWF and collagen.

Figure 16:
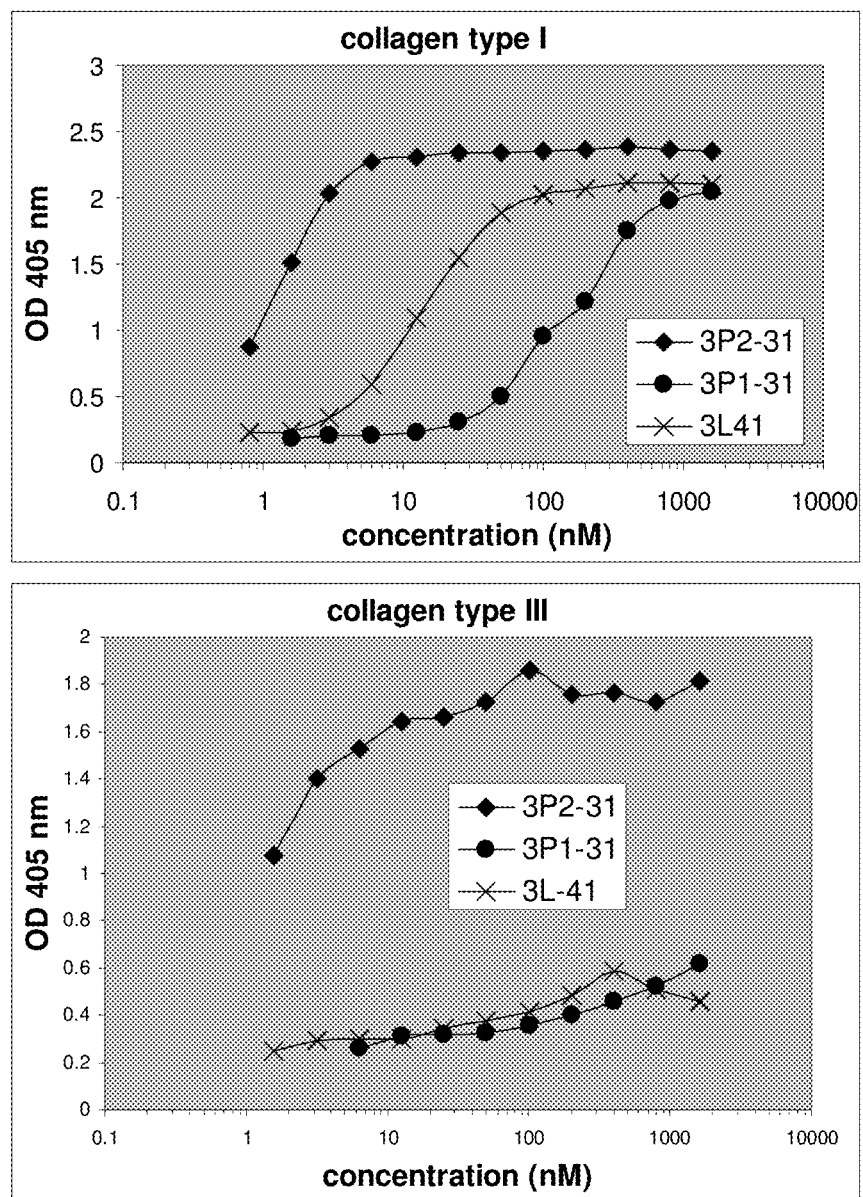

FIG. 16. Binding of purified VHH to collagen type I and type III in ELISA as described in Example 34.

FIG. 17. Phage ELISA to show that HSA-specific nanobodies are present in the library as described in Example 44.

FIG. 18. Binding of phages expressing the albumin binders, to plasma blotted on nitrocellulose as described in Example 48.

Figure 19:
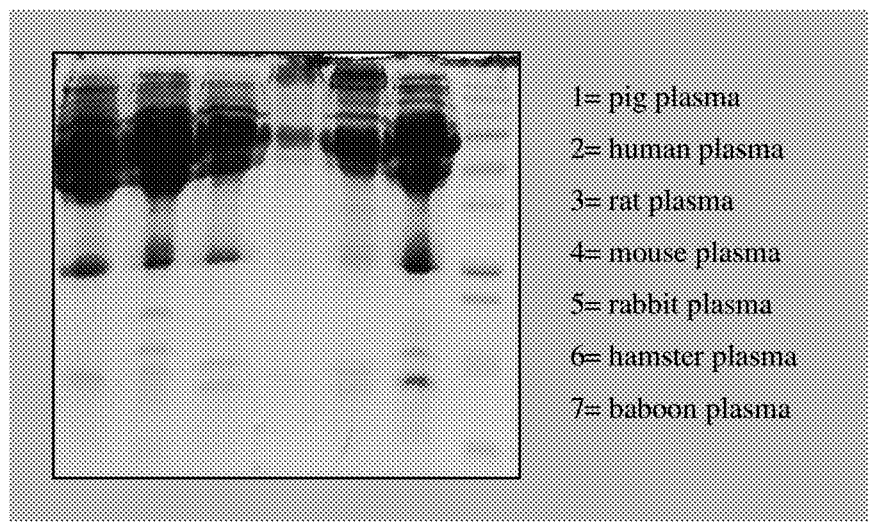

FIG. 19. Coomassie staining of plasma samples on SDS-PAGE as described in Example 48.

FIG. 20. Binding of purified nanobodies to mouse albumin as determined by ELISA as described in Example 50.

FIG. 21. Bispecific constructs with one VHH binding to albumin and a second VHH binding to vWF for improvement of half-life as described in Example 51.

FIG. 22. Sandwich ELISA showing the functionality of both VHHs in a bispecific construct as described in Example 53.

Figure 23:
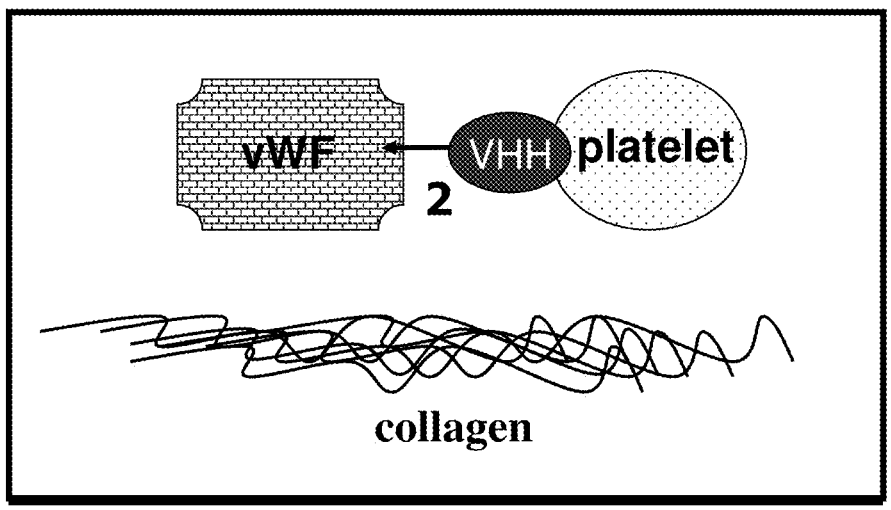

FIG. 23. Interactions involved in the first steps of platelet aggregation. A VHH is indicated specific for gpIb and inhibiting the interaction between vWF and platelets.

Figure 24:
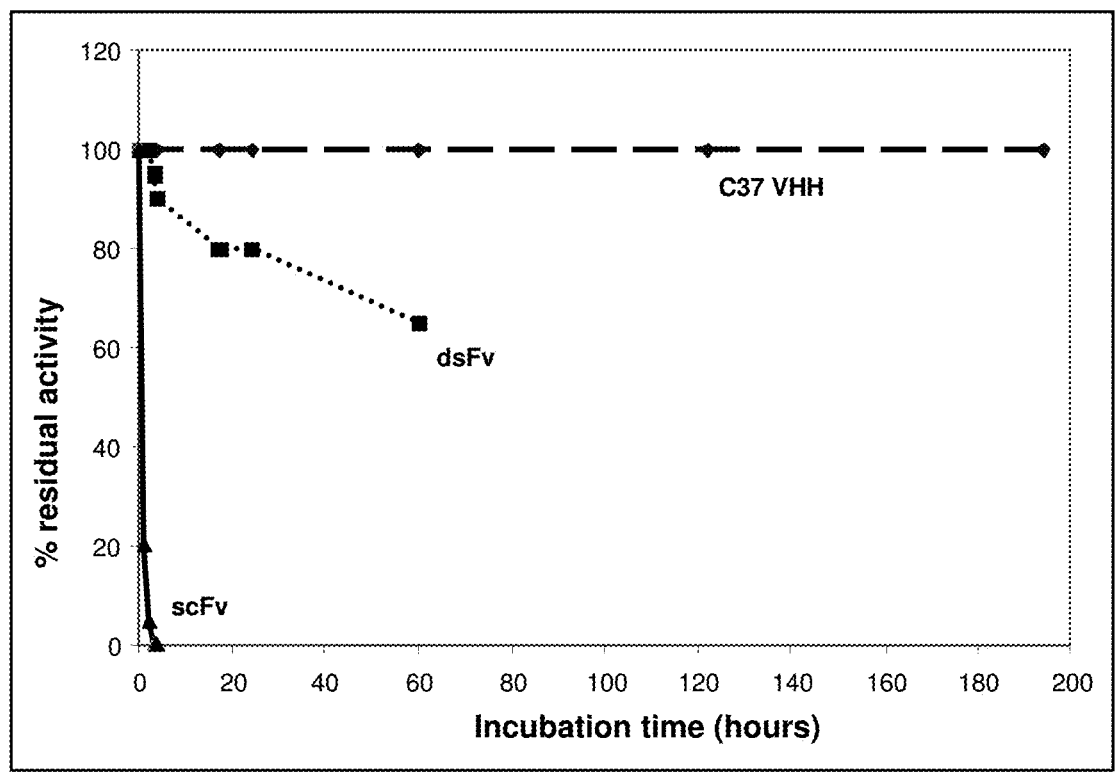
Figure 25:
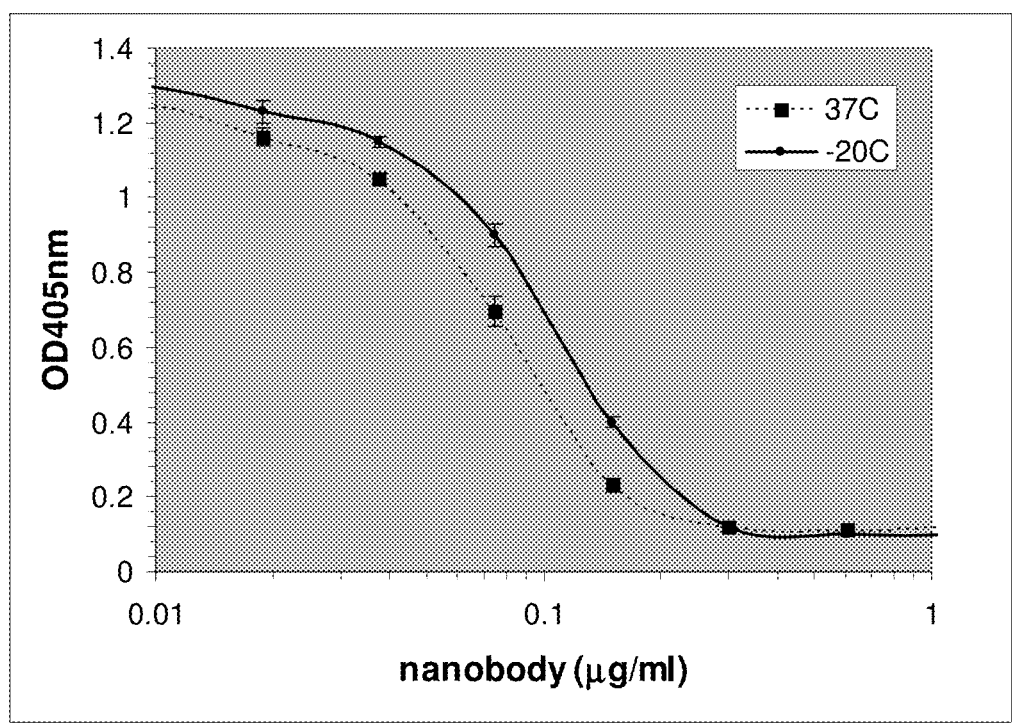

FIG. 24. Residual activity for C37 stored at −20° C. as compared to C37 incubated at 37° C. for up to 194 hours. C37 stability is compared to stability of a scFv specific for B3 antigen and a stabilized form, dsFv (stabilized by 2 disulphide bonds) as described in Example 61.

FIG. 25. Inhibitory activity for C37 stored at −20° C. as compared to C37 incubated at 37° C. for 1 year as described in Example 61.

FIG. 26. Binding of vWF from human plasma to C37 immobilized in acrylamide as described in Example 62.

FIG. 27. Amino acid alignment of C37 with human germline sequence DP-47 as described in Example 63.

FIG. 28. Inhibition of binding of vWF to collagen as determined by ELISA for C37 and C37 hum as described in Example 64.

Figure 30:
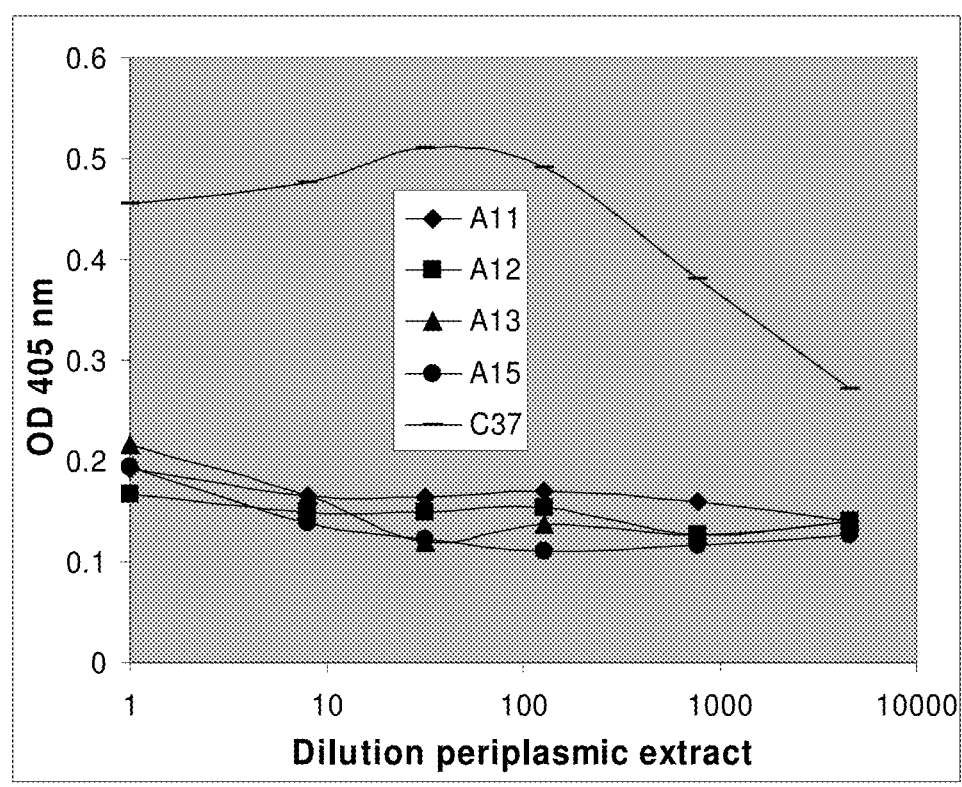

FIG. 29. Binding of A11, A12, A13, A14, A15 and A16 clones to rA1 as measured in ELISA FIG. 30. Binding of A11, A12, A13, A14, A15 and A16 clones to vWF as measured in ELISA

TABLES

Table 1. Immunization scheme used for llama 002 according to Example 1.

Table 2. Plaque forming units (pfu) after one or two round(s) of panning on vWF as compared to PBS-casein as described in Example 4. Pfu vWF (antigen) divided by pfu casein (a specific binding)=enrichment.

Table 3. Number of inhibitors versus the number of clones tested after the first and the second round of panning as described in Example 5.

Table 4. Yield (mg/liter culture) after expression and purification of VHH grown in WK6 E. coli cells as described in Example 6.

Table 5. OD 405 nm for binding of VHH in ELISA to vWF and 3 antigens that were also immunized in llama002 according to Example 8.

Table 6. Concentration of VHH (nM) needed to inhibit binding of vWF to collagen by 50% (IC50) as described in Example 9.

Table 7. Epitope mapping of VHH binding to vWF and inhibiting the interaction with collagen as described in example 11.

Table 8. Yields of purified protein (mg) per liter of culture for bivalent and bispecific VHHs as described in Example 12.

Table 9. IC50 values for monovalent as compared to bivalent and bispecific VHHs. Inhibition was tested with human, pig and baboon plasma as described in Example 14.

Table 10. Inhibition of platelet aggregation at high shear ($1600\ s^{-1}$) as described in Example 16.

Table 11. Inhibition of platelet aggregation at low shear ($300\ s^{-1}$) as described in Example 16.

Table 12. Plaque forming units (pfu) after one round of panning on vWF as described in Example 17. Pfu vWF (antigen) divided by pfu casein (a-specific binding)=enrichment.

Table 13. Results of screening in ELISA of individual colonies for binding to vWF and to the A1 domain of vWF as described in Example 18.

Table 14. Results after one round of MATCHM on pBAD-Oprl-A1 cells as described in Example 19.

Table 15. Inhibition of platelet aggregation at high shear ($1600\ s^{-1}$) as described in Example 23.

Table 16. Inhibition of platelet aggregation at low shear ($300\ s^{-1}$) as described in Example 23.

Table 17. Inhibition of platelet aggregation at high shear ($1600\ s^{-1}$) as described in Example 25.

Table 18. Inhibition of platelet aggregation at low shear ($300\ s^{-1}$) as described in Example 25.

Table 19. Yields after expression and purification of bispecific constructs as described in Example 27.

Table 20. IC50 values for bispecific nanobodies for the A1 and A3 domain of vWF as described in Example 29.

Table 21. Inhibition of platelet aggregation at high shear ($1600\ s^{-1}$) as described in Example 30.

Table 22. Inhibition of platelet aggregation at low shear ($300\ s^{-1}$) as described in Example 30.

Table 23. Plaque forming units (pfu) after one round of panning on collagen type I as described in Example 31. Pfu vWF (antigen) divided by pfu casein (a-specific binding)=enrichment.

Table 24. Number of clones binding to collagen type I and type III after one round of selection as described in Example 32.

Table 25. Immunization scheme for human serum albumin according to example 41.

Table 26. Results after one and two rounds of panning on mouse serum albumin as described in Example 45.

Table 27. Clones were selected after one and two rounds of selection and periplasmic extracts were prepared. These clones were analyzed in ELISA for binding to human and mouse albumin as described in Example 46.

Table 28. IC50 values for bispecific nanobodies against albumin and against vWF as described in Example 54.

Table 29. Sequences of the primers used for humanization of C37 as described in Example 64.

Table 30. Amino acid sequence listing of the peptides of the present invention and of human von Willebrand factor (vWF). The sequence of human vWF indicates A1 and A3 domains respectively in bold lettering.

Table 31. Results after two panning rounds on rA1 domain of vWF as described in Example 66.

Table 32. ELISA analyses of selected clones for binding to rA1 and vWF as described in Example 67.

TABLE 1

Immunization scheme used for llama 002 according to Example 1.

| Llama002 Day of immunization | vWF | Collagen Type I | Collagen Type III |
| --- | --- | --- | --- |
| 0 | 100 μg | 100 μg | 100 μg |
| 7 | 100 μg | 100 μg | 100 μg |
| 14 | 50 μg | 50 μg | 50 μg |
| 21 | 50 μg | 50 μg | 50 μg |
| 28 | 50 μg | 50 μg | 50 μg |
| 35 | 50 μg | 50 μg | 50 μg |

TABLE 2

Plaque forming units (pfu) after one or two round(s) of panning on vWF as compared to PBS-casein as described in example 4. Pfu vWF (antigen) divided by pfu casein (a specific binding) = enrichment.

| round | Pfu vWF | Pfu casein | Enrichment |
| --- | --- | --- | --- |
| First | $1 \times 10^7$ | $2.5 \times 10^5$ | 40 |
| Second | $5 \times 10^8$ | $2.5 \times 10^6$ | 200 |

TABLE 3

Number of inhibitors versus the number of clones tested after the first and the second round of panning as described in Example 5.

| round | Number of inhibitors versus number of clones tested |
| --- | --- |
| First | 4/800 |
| Second | 4/96 |

TABLE 4

Yield (mg/liter culture) after expression and purification of VHH grown in WK6 E.coli cells as described in Example 6.

| Name VHH | Yield (mg/liter culture) |
|---|---|
| 22-2L-34 | 1.4 |
| T76 | 2.9 |
| AM-4-15-3 | 2.2 |
| 22-4L-16 | 2.8 |
| C37 | 3.8 |
| AM-2-75 | 3.6 |

TABLE 5

OD 405 nm for binding of VHH in ELISA to vWF and 3 antigens that were also immunized in llama002 according to Example 8.

| | OD405 nm | | | | | | | | | | | |
|---|---|---|---|---|---|---|---|---|---|---|---|---|
| | vWF | | | Antigen 1 | | | Antigen 2 | | | Antigen 3 | | |
| | | | | | nM | | | | | | | |
| | 670 | 67 | 6.7 | 670 | 67 | 6.7 | 670 | 67 | 6.7 | 670 | 67 | 6.7 |
| T76 | 0.77 | 0.36 | 0.13 | 0.05 | 0.05 | 0.05 | 0.06 | 0.06 | 0.04 | 0.04 | 0.04 | 0.03 |
| 22-2L-34 | 1.30 | 0.63 | 0.20 | 0.06 | 0.0 | 0.10 | 0.10 | 0.07 | 0.05 | 0.06 | 0.05 | 0.03 |
| 22-4L-16 | 1.41 | 0.86 | 0.81 | 0.08 | 0.10 | 0.11 | 0.15 | 0.11 | 0.05 | 0.08 | 0.07 | 0.03 |
| C37 | 1.51 | 1.09 | 1.06 | 0.10 | 0.10 | 0.12 | 0.12 | 0.11 | 0.08 | 0.10 | 0.08 | 0.06 |
| AM-2-75 | 1.57 | 1.10 | 1.04 | 0.09 | 0.11 | 0.12 | 0.14 | 0.11 | 0.09 | 0.10 | 0.13 | 0.05 |
| AM-4-15-3 | 1.32 | 1.06 | 0.56 | 0.09 | 0.12 | 0.12 | 0.12 | 0.11 | 0.10 | 0.10 | 0.10 | 0.08 |

TABLE 6

Concentration of VHH (nM) needed to inhibit binding of vWF to collagen by 50% (IC50) as described in Example 9.

| Name VHH | IC50 (nM) human plasma 1/60 | IC50 (nM) undiluted human plasma |
|---|---|---|
| 22-2L-34 | 10 | — |
| T76 | 30 | — |
| AM-4-15-3 | 7 | 200 |
| 22-4L-16 | 4 | 1000 |
| C37 | 3 | — |
| AM-2-75 | 2 | 100 |

TABLE 7

Epitope mapping of VHH binding to vWF and inhibiting the interaction with collagen as described in Example 11.

| Name VHH | Binding to A3 domain of vWF |
|---|---|
| 22-2L-34 | Yes |
| T76 | No |
| 22-4L-16 | No |
| C37 | Yes |
| AM-2-75 | Yes |

TABLE 8

Yields of purified protein (mg) per liter of culture for bivalent and bispecific VHHs as described in Example 12.

| NH2-terminal VHH | COOH-terminal VHH | Yield mg/liter culture |
|---|---|---|
| AM-2-75 | AM-4-15-3 | 3.2 |
| AM-4-15-3 | AM-4-15-3 | 2.3 |
| AM-4-15-3 | AM-2-75 | 4.0 |
| AM-2-75 | AM-2-75 | 1.0 |
| AM-2-75 | 22-4L-16 | 3.0 |

TABLE 9

IC50 values for monovalent as compared to bivalent and bispecific VHHs. Inhibition was tested with human, pig and baboon plasma as described in Example 14.

| First VHH | Second VHH | IC50 (ng/ml) human plasma | IC50 (ng/ml) baboon plasma | IC50 (ng/ml) pig plasma |
|---|---|---|---|---|
| AM-2-75 | | 150 | 400 | 50 |
| AM-4-15-3 | | 50 | 200 | 40 |
| 22-4L-16 | | 15 | 70 | 7 |
| AM-2-75 | AM-4-15-3 | 3 | 5 | 6 |
| AM-4-15-3 | AM-2-75 | 2 | 8 | 3 |
| AM-4-15-3 | AM-4-15-3 | 5 | 10 | 7 |
| AM-2-75 | 22-4L-16 | 8 | 20 | 10 |
| AM-2-75 | AM-2-75 | 5 | | |

TABLE 10

Inhibition of platelet aggregation at high shear (1600 s$^{-1}$) as described in Example 16.

| | Concentration [μg/ml] | % inhibition |
|---|---|---|
| AM-2-75 | 0.2 | 0 |
| AM-2-75 | 0.3 | 12 |
| AM-2-75 | 0.4 | 56 |
| AM-2-75 | 0.6 | 97 |
| AM-2-75 | 0.8 | 96 |
| AM-4-15-3 | 0.05 | 0 |
| AM-4-15-3 | 0.1 | 75 |
| AM-4-15-3 | 0.25 | 74 |
| AM-4-15-3 | 0.5 | 86 |
| AM-4-15-3 | 1 | 91 |
| 22-4L-16 | 0.1 | 32 |
| 22-4L-16 | 0.5 | 54 |
| 22-4L-16 | 0.75 | 86 |
| 22-4L-16 | 2 | 97 |
| 22-4L-16 | 10 | 99 |

TABLE 10-continued

Inhibition of platelet aggregation at high shear (1600 s$^{-1}$) as described in Example 16.

| | Concentration [μg/ml] | % inhibition |
|---|---|---|
| AM-4-15-3/AM-4-15-3 | 0.05 | 0 |
| AM-4-15-3/AM-4-15-3 | 0.075 | 23 |
| AM-4-15-3/AM-4-15-3 | 0.1 | 37 |
| AM-4-15-3/AM-4-15-3 | 0.15 | 56 |
| AM-4-15-3/AM-4-15-3 | 0.2 | 98 |
| AM-4-15-3/AM-4-15-3 | 1.9 | 100 |
| AM-4-15-3/AM-2-75 | 1.9 | 100 |
| AM-2-75/AM-4-15-3 | 0.05 | 2 |
| AM-2-75/AM-4-15-3 | 0.1 | 36 |
| AM-2-75/AM-4-15-3 | 0.2 | 96 |
| AM-2-75/AM-4-15-3 | 0.35 | 91 |
| AM-2-75/AM-4-15-3 | 0.4 | 98 |
| AM-2-75/AM-2-75 | 0.04 | 5 |
| AM-2-75/AM-2-75 | 0.1 | 26 |
| AM-2-75/AM-2-75 | 0.2 | 52 |
| AM-2-75/AM-2-75 | 0.3 | 80 |
| AM-2-75/AM-2-75 | 0.4 | 99 |
| AM-2-75/AM-2-75 | 0.83 | 100 |
| AM-2-75/22-4L-16 | 1.17 | 99 |

TABLE 11

Inhibition of platelet aggregation at low shear (300 s$^{-1}$) as described in Example 16.

| | Concentration [μg/ml] | % inhibition |
|---|---|---|
| AM-2-75 | 10 | 20 |
| AM-4-15-3 | 10 | 17 |
| 22-4L-16 | 10 | 22 |
| AM-4-15-3/AM-4-15-3 | 10 | 23 |
| AM-4-15-3/AM-2-75 | 10 | 21 |
| AM-2-75/AM-4-15-3 | 10 | 18 |
| AM-2-75/AM-2-75 | 2 | 32 |
| AM-2-75/22-4L-16 | 10 | 13 |

TABLE 12

Plaque forming units (pfu) after one round of panning on vWF as described in Example 17. Pfu vWF (antigen) divided by pfu casein (a-specific binding) = enrichment

| Pfu vWF | Pfu casein | Enrichment |
|---|---|---|
| $1.5 \times 10^7$ | $1 \times 10^4$ | 1.500 |

TABLE 13

Results of screening in ELISA of individual colonies for binding to vWF and to the A1 domain of vWF as described in Example 18.

| No. clones +ve for vWF/No. tested | No. clones +ve for A1/No. tested |
|---|---|
| 344/380 | 5/570 |

TABLE 14

Results after one round of MATCHM on pBAD-Oprl-A1 cells as described in Example 19.

| Round | No. clones +ve for vWF/No. tested | No. clones +ve for A1/No. tested |
|---|---|---|
| First | — | 1/96 |
| second | 45/348 | 12/348 |

TABLE 15

Inhibition of platelet aggregation at high shear (1600 s$^{-1}$) as described in Example 23.

| | Concentration [μg/ml] | % inhibition |
|---|---|---|
| 2A1-4L-129 | 13.5 | 26 |
| 2A1-4L-129 | 20 | 50 |
| 2L-A1-15 | 9.7 | 30 |
| 2L-A1-15 | 25 | 45 |
| A50 | 10.2 | 20 |
| 2A1-4L-79 | 11.1 | 20 |
| 2A1-4L-34 | 11.1 | 3 |
| Z29 | 10.6 | 0 |
| I53 | 9.7 | 0 |
| M53 | 10.6 | 0 |

TABLE 16

Inhibition of platelet aggregation at low shear (300 s$^{-1}$) as described in Example 23.

| | Concentration [μg/ml] | % inhibition |
|---|---|---|
| 2A1-4L-129 | 10 | 0 |
| 2L-A1-15 | 10 | 3 |
| A50 | 25 | 0 |
| 2A1-4L-79 | 25 | 15 |

TABLE 17

Inhibition of platelet aggregation at high shear (1600 s$^{-1}$) as described in Example 25.

| | Concentration [μg/ml] | % inhibition |
|---|---|---|
| 2A1-4L-79/2A1-4L-79 | 25 | 54 |
| 2LA1-15/2LA1-15 | 25 | 45 |

TABLE 18

Inhibition of platelet aggregation at low shear (300 s$^{-1}$) as described in Example 25.

| | Concentration [μg/ml] | % inhibition |
|---|---|---|
| 2A1-4L-79/2A1-4L-79 | 25 | 0 |
| 2LA1-15/2LA1-15 | 25 | 23 |

TABLE 19

Yields after expression and purification of bispecific constructs as described in Example 27.

| NH2 terminal VHH | COOH-terminal VHH | Yield mg/liter culture |
|---|---|---|
| 2A1-4L-79 | AM-4-15-3 | 7.5 |
| 2A1-4L-79 | AM-2-75 | 2 |
| 2A1-4L-79 | 22-4L-16 | 2.5 |

TABLE 20

IC50 values for bispecifici nanobodies for the A1 and A3 domain of vWF as described in example 29.

| NH2-terminal VHH | COOH-terminal VHH | IC50 (ng/ml) |
|---|---|---|
| 2A1-4L-79 | AM-4-15-3 | 10 |
| AM-4-15-3 | — | 45 |
| 2A1-4L-79 | AM-2-75 | 12 |
| AM-2-75 | — | 40 |
| 2A1-4L-79 | 22-4L-16 | 10 |
| 22-4L-16 | — | 10 |
| 2A1-4L-79 | — | >10000 |

TABLE 21

Inhibition of platelet aggregation at high shear (1600 s$^{-1}$) as described in Example 30.

| | Concentration [µg/ml] | % inhibition |
|---|---|---|
| 2A1-4L-79/AM-4-15-3 | 12 | 100 |
| 2A1-4L-79/AM-2-75 | 0.02 | 0 |
| 2A1-4L-79/AM-2-75 | 0.1 | 28 |
| 2A1-4L-79/AM-2-75 | 0.5 | 79 |
| 2A1-4L-79/AM-2-75 | 1 | 95 |
| 2A1-4L-79/22-4L-16 | 12 | 96 |

TABLE 22

Inhibition of platelet aggregation at low shear (300 s$^{-1}$) as described in Example 30.

| | Concentration [µg/ml] | % inhibition |
|---|---|---|
| 2A1-4L-79/AM-4-15-3 | 10 | 15 |
| 2A1-4L-79/AM-2-75 | 10 | 25 |
| 2A1-4L-79/22-4L-16 | 10 | 27 |

TABLE 23

Plaque forming units (pfu) after one round of panning on collagen type I as described in Example 31. Pfu vWF (antigen) divided by pfu casein (a-specific binding) = enrichment.

| | |
|---|---|
| Phages eluted from collagen type I | 5 × 10$^6$ |
| Phages eluted from casein | 4 × 10$^4$ |
| Enrichment | 100 |

TABLE 24

Number of clones binding to collagen type I and type III after one round of selection as described in Example 32.

| | |
|---|---|
| Collagen Type I | 15/32 |
| Collagen Type III | 7/32 |
| Casein | 0/32 |

TABLE 25

Immunization scheme for human serum albumin according to Example 41.

| Day of immunization | HSA Llama006 |
|---|---|
| 0 | 100 µg |
| 7 | 100 µg |
| 14 | 50 µg |
| 21 | 50 µg |
| 28 | 50 µg |
| 35 | 50 µg |

TABLE 26

Results after one and two rounds of panning on mouse serum albumin as described in Example 45.

| | First round | Second round |
|---|---|---|
| Pfu mouse serum albumin | 2.5 × 10$^7$ | 2.5 × 10$^7$ |
| Pfu casein | 5 × 10$^3$ | 2.5 × 10$^3$ |
| Enrichment | 5.000 | 10.000 |

TABLE 27

Clones were selected after one and two rounds of selection and periplasmic extracts were prepared. These clones were analyzed in ELISA for binding to human and mouse albumin as described in Example 46.

| | First round | Second round |
|---|---|---|
| ELISA mouse serum albumin | 1/16 | 15/16 |
| ELISA human serum albumin | 1/16 | 15/16 |
| ELISA casein | 0/16 | 0/16 |

TABLE 28

IC50 values for bispecific nanobides against albumin and against vWF as described in Example 54.

| | IC50 (ng/ml) |
|---|---|
| AM-2-75 | 100 |
| MSA21/AM-2-75 | 60 |
| AM-4-15-3 | 155 |
| MSA21/AM-4-15-3 | 245 |
| 22-4L-16 | 100 |
| MSA21/22-4L-16 | 140 |

TABLE 29

Sequences of the primers used for humanization of C37 as described in Example 64.

| Mutation | Template | Primer sequence | SEQ ID NO |
|---|---|---|---|
| A74S+ N75K+ P84A | Wild type | 5'-AGA GAC AAC TCC AAG AAC ACG CTG TAT CTG CAA ATG AAC AGC CTG AGA GCT GAG GAC ACG-3' | 76 |
| | | Arg Asp Asn Ser Lys Asn Thr Leu Tyr Leu Gln Met Asn Ser Leu Arg Ala Glu Asp Thr | 77 |
| A74S+ | A74S+ | 5'-AT TAC TGT GCT AAA GGG GCC GGT ACT AGT T-3' | 78 |

TABLE 29-continued

Sequences of the primers used for humanization of C37 as described in Example 64.

| Muta-tion | Template | Primer sequence | SEQ ID NO |
|---|---|---|---|
| N75K+ P84A+ R94K | N75K+ P84A | Tyr Cys Ala Lys Gly Ala Gly Thr Ser | 79 |
| N28T+ N30S | A74S+ N75K+ | 5'-TCC TGT GCA GCC TCC GGA TTC ACT TTC AGT TGG TA-3' | 80 |
| A74S+ N75K+ P84A+ R94K | P84A+ R94K | Ser Cys Ala Ala Ser Gly Phe Thr Phe Ser Trp | 81 |

TABLE 30

Amino acid sequence listing of the peptides of the present invention and of human von Willebrand factor (vWF). The sequence of human vWF indicates A1 and A3 domains respectively in bold lettering.

| NAME | SEQ ID NO | SEQUENCE |
|---|---|---|
| Anti-vWF A3 VHH | | |
| C37 | 1 | QVQLQESGGGLVQPGGSLRLSCAASGFNFNWYPMSWVRQAPGKGLEWVSTIS TYGEPRYADSVKGRFTISRDNANNTLYLQMNSLRPEDTAVYYCARGAGTSSY LPQRGNWDQGTQVTISS |
| C37-hum | 2 | QVQLQESGGGLVQPGGSLRLSCAASGFTFSWYPMSWVRQAPGKGLEWVSTIS TYGEPRYADSVKGRFTISRDNSKNTLYLQMNSLRAEDTAVYYCAKGAGTSSY LPQRGNWDQGTQVTISS |
| AM-2-75 | 3 | QVQLQESGGGLVQPGGSLRLSCAASGFNFNWYPMSWVRQAPGKGLEWVSTIS TYGEPRYADSVKGRFTISRDNANNTLYLQMNSLRPEDTAVYYCARGAGTSSY LPQRGNWDQGTQVTVSS |
| 22-2L-34 | 4 | QVQLQDSGGGLVQAGGSLRLSCAASVRIFTSYAMGWFRQAPGKEREFVAAIN RSGKSTYYSDSVEGRFTISRDNAKNTVSLQMDSLKLEDTAVYYCAADYSGSY TSLWSRPERLDWGQGTQVTVFS |
| 22-4L-16 | 5 | QVQLVESGGGLVQAGGSLRLSCAASGRTFSSYAMGWFRQAPGKEREFVAAIS WSGGSTYYADSVKGRFTISRDNAKNTVYLQMNSLKPEDTAVYYCVADTGGIS WIRTQGYNYWGQGTQVTVSS |
| T76 | 6 | QVQLQESGGGLVQPGESLRLSCAASGSIFSINTMGWYGQAPGKQRELVASIT FGGVTNYADSVKGRFTISRDNTNDTVYLQMNSLKPEDTAVYICNAVTWGGLT NYWGQGTQVTVSS |
| AM-4-15-3 | 7 | QVQLQDSGGGLVQPGGSLRLACAASGSIFSINSMGWYRQAPGKQRELVAHAL ADGSASYRDSVKGRFTISRDNAKNTVYLQMNSLKPEDTAVYYCNTVPSSVTK GYWGQGTQVTVSS |
| Anti-vWF A3 domain VHH: bivalent or bispecific | | |
| AM-4-15-3/AM-4-15-3 | 8 | QVQLQDSGGGLVQPGGSLRLACAASGSIFSINSMGWYRQAPGKQRELVAHAL ADGSASYRDSVKGRFTISRDNAKNTVYLQMNSLKPEDTAVYYCNTVPSSVTK GYWGQGTQVTVSSEPKTPKPQPAAAQVQLQDSGGGLVQPGGSLRLACAASGS IFSINSMGWYRQAPGKQRELVAHALADGSASYRDSVKGRFTISRDNAKNTVY LQMNSLKPEDTAVYYCNTVPSSVTKGYWGQGTQVTVSS |
| AM-4-15-3/AM-2-75 | 9 | QVQLQDSGGGLVQPGGSLRLACAASGSIFSINSMGWYRQAPGKQRELVAHAL ADGSASYRDSVKGRFTISRDNAKNTVYLQMNSLKPEDTAVYYCNTVPSSVTK GYWGQGTQVTVSSEPKTPKPQPAAAQVQLQESGGGLVQPGGSLRLSCAASGF NFNWYPMSWVRQAPGKGLEWVSTISTYGEPRYADSVKADSPSSETTPTTRCI CNEQPETEDTAVYYCARGAGTSSYLPQRGNWDQGTQVTVSS |
| AM-2-75/AM-4-15-3 | 10 | QVQLQESGGGLVQPGGSLRLSCAASGFNFNWYPMSWVRQAPGKGLEWVSTIS TYGEPRYADSVKGRFTISRDNANNTLYLQMNSLRPEDTAVYYCARGAGTSSY LPQRGNWDQGTQVTVSSEPKTPKPQPAAAQVQLQDSGGGLVQPGGSLRLACA ASGSIFSINSMGWYRQAPGKQRELVAHALADGSASYRDSVKGRFTISRDNAK NTVYLQMNSLKPEDTAVYYCNTVPSSVTKGYWGQGTQVTVSS |
| AM-2-75/AM- | 11 | QVQLQESGGGLVQPGGSLRLSCAASGFNFNWYPMSWVRQAPGKGLEWVSTIS TYGEPRYADSVKGRFTISRDNANNTLYLQMNSLRPEDTAVYYCARGAGTSSY |

TABLE 30-continued

Amino acid sequence listing of the peptides of the present invention and of human von Willebrand factor (vWF). The sequence of human vWF indicates A1 and A3 domains respectively in bold lettering.

| NAME | SEQ ID NO | SEQUENCE |
|---|---|---|
| 2-75 | | LPQRGNWDQGTQVTVSSQVQLQESGGGLVQPGGSLRLSCAASGFNFNWYPMS WVRQAPGKGLEWVSTISTYGEPRYADSVKGRFTISRDNANNTLYLQMNSLRP EDTAVYYCARGAGTSSYLPQRGNWDQGTQVTVSS |
| AM-2-75/22-4L-16 | 12 | QVQLQESGGGLVQPGGSLRLSCAASGFNFNWYPMSWVRQAPGKGLEWVSTIS TYGEPRYADSVKGRFTISRDNANNTLYLQMNSLRPEDTAVYYCARGAGTSSY LPQRGNWDQGTQVTVSSEPKTPKPQPAAAQVQLVESGGGLVQAGGSLRLSCA ASGRTFSSYAMGWFRQAPGKEREFVAAISWSGGSTYYADSVKGRFTISRDNA KNTVYLQMNSLKPEDTAVYYCVADTGGISWIRTQGYNYWGQGTQVTVSS |

Anti-vWF VHH + anti-mouse serum albumin VHH

| NAME | SEQ ID NO | SEQUENCE |
|---|---|---|
| MSA21/AM-2-75 | 13 | QVQLQESGGGLVQPGGSLRLSCEASGFTFSRFGMTWVRQAPGKGVEWVSGIS SLGDSTLYADSVKGRFTSRDNAKNTLYLQMNSLKPEDTAVYYCTIGGSLNPG GQGTQVTVSSEPKTPKPQPAAAQVQLQESGGGLVQPGGSLRLSCAASGFNFN WYPMSWVRQAPGKGLEWVSTISTYGEPRYADSVKADSPSSETTPTTRCICNE QPETEDTAVYYCARGAGTSSYLPQRGNWDQGTQVTVSS |
| MSA21/AM-4-15-3 | 14 | QVQLQESGGGLVQPGGSLRLSCEASGFTFSRFGMTWVRQAPGKGVEWVSGIS SLGDSTLYADSVKGRFTSRDNAKNTLYLQMNSLKPEDTAVYYCTIGGSLNPG GQGTQVTVSSEPKTPKPQPAAAQVQLDSGGGLVQPGGSLRLACAASGSIFS INSMGWYRQAPGKQRELVAHALADGSASYRDSVKGRFTISRDNAKNTVYLQM NSLKPEDTAVYYCNTVPSSVTKGYWGQGTQVTVSS |
| MSA21/22-4L-16 | 15 | QVQLQESGGGLVQPGGSLRLSCEASGFTFSRFGMTWVRQAPGKGVEWVSGIS SLGDSTLYADSVKGRFTSRDNAKNTLYLQMNSLKPEDTAVYYCTIGGSLNPG GQGTQVTVSSEPKTPKPQPAAAQVQLVESGGGLVQAGGSLRLSCAASGRTFS SYAMGWFRQAPGKEREFVAAISWSGGSTYYADSVKGRFTISRDNAKNTVYLQ MNSLKPEDTAVYYCVADTGGISWIRTQGYNYWGQGTQVTVSS |

Anti mouse serum albumin VHH

| NAME | SEQ ID NO | SEQUENCE |
|---|---|---|
| MSA21 | 16 | QVQLQESGGGLVQPGGSLRLSCEASGFTFSRFGMTWVRQAPGKGVEWVSGIS SLGDSTLYADSVKGRFTISRDNAKNTLYLQMNSLKPEDTAVYYCTIGGSLNP GGQGTQVTVSS |
| MSA24 | 17 | QVQLQESGGGLVQPGNSLRLSCAASGFTFRNFGMSWVRQAPGKEPEWVSSIS GSGSNTIYADSVKDRFTISRDNAKSTLYLQMNSLKPEDTAVYYCTIGGSLSR SSQGTQVTVSS |
| MSA210 | 18 | QVQLQESGGGLVQPGGSLRLTCTASGFTFSSFGMSWVRQAPGKGLEWVSAIS SDSGTKNYADSVKGRFTISRDNAKKMLFLQMNSLRPEDTAVYYCVIGRGSPS SQGTQVTVSS |
| MSA212 | 19 | QVQLQESGGGLVQPGGSLRLTCTASGFTFRSFGMSWVRQAPGKGLEWVSAIS ADGSDKRYADSVKGRFTISRDNGKKMLTLDMNSLKPEDTAVYYCVIGRGSPA SQGTQVTVSS |
| MSAc16 | 49 | AVQLVESGGGLVQAGDSLRLSCVVSGTTFSSAAMGWFRQAPGKEREFVGAIK WSGTSTYYTDSVKGRFTISRDNVKNTVYLQMNNLKPEDTGVYTCAADRDRYR DRMGPMTTTDFRFWGQGTQVTVSS |
| MSAcl12 | 50 | QVKLEESGGGLVQTGGSLRLSCAASGRTFSSFAMGWFRQAPGREREFVASIG SSGITTNYADSVKGRFTISRDNAKNTVYLQMNSLKPEDTGLCYCAVNRYGIP YRSGTQYQNWGQGTQVTVSS |
| MSAcl10 | 51 | EVQLEESGGGLVQPGGSLRLSCAASGLTFNDYAMGWYRQAPGKERDMVATIS IGGRTYYADSVKGRFTISRDNAKNTVYLQMNSLKPEDTAIYYCVAHRQTVVR GPYLLWGQGTQVTVSS |
| MSAcl14 | 52 | QVQLVESGGKLVQAGGSLRLSCAASGRTFSNYAMGWFRQAPGKEREFVAGSG RSNSYNYYSDSVKGRFTISRDNAKNTVYLQMNSLKPEDTAVYYCAASTNLWP RDRNLYAYWGQGTQVTVSS |
| MSAcl16 | 53 | EVQLVESGGGLVQAGDSLRLSCAASGRSLGIYRMGWFRQVPGKEREFVAAIS WSGGTTRYLDSVKGRFTISRDSTKNAVYLQMNSLKPEDTAVYYCAVDSSGRL YWTLSTSYDYWGQGTQVTVSS |
| MSAcl19 | 54 | QVQLVEFGGGLVQAGDSLRLSCAASGRSLGIYKMAWFRQVPGKEREFVAAIS WSGGTTRYIDSVKGRFTLSRDNTKNMVYLQMNSLKPDDTAVYYCAVDSSGRL YWTLSTSYDYWGQGTQVTVSS |

TABLE 30-continued

Amino acid sequence listing of the peptides of the present invention and of human von Willebrand factor (vWF). The sequence of human vWF indicates A1 and A3 domains respectively in bold lettering.

| NAME | SEQ ID NO | SEQUENCE |
|---|---|---|
| MSAc15 | 55 | EVQLVESGGGLVQAGGSLSLSCAASGRTFSPYTMGWFRQAPGKEREFLAGVT WSGSSTFYGDSVKGRFTASRDSAKNTVTLEMNSLNPEDTAVYYCAAAYGGGL YRDPRSYDYWGRGTQVTVSS |
| MScl11 | 56 | AVQLVESGGGLVQAGGSLRLSCAASGFTLDAWPIAWFRQAPGKEREGVSCIR DGTTYYADSVKGRFTISSDNANNTVYLQTNSLKPEDTAVYYCAAPSGPATGS SHTFGIYWNLRDDYDNWGQGTQVTVSS |
| MSAc115 | 57 | EVQLVESGGGLVQAGGSLRLSCAASGFTFDHYTIGWFRQVPGKEREGVSCIS SSDGSTYYADSVKGRFTISSDNAKNTVYLQMNTLEPDDTAVYYCAAGGLLLR VEELQASDYDYWGQGIQVTVSS |
| MSAc18 | 58 | AVQLVDSGGGLVQPGGSLRLSCTASGFTLDYYAIGWFRQAPGKEREGVACIS NSDGSTYYGDSVKGRFTISRDNAKTTVYLQMNSLKPEDTAVYYCATADRHYS ASHHPFADFAFNSWGQGTQVTVSS |
| MSAc17 | 59 | EVQLVESGGGLVQAGGSLRLSCAAYGLTFWRAAMAWFRRAPGKERELVVARN WGDGSTRYADSVKGRFTISRDNAKNTVYLQMNSLKPEDTAVYYCAAVRTYGS ATYDIWGQGTQVTVSS |
| MSAc120 | 60 | EVQLVESGGGLVQDGGSLRLSCIFSGRTFANYAMGWFRQAPGKEREFVAAIN RNGGTTNYADALKGRFTISRDNTKNTAFLQMNSLKPDDTAVYYCAAREWPFS TIPSGWRYWGQGTQVTVSS |
| MSAc14 | 61 | DVQLVESGGGWVQPGGSLRLSCAASGPTASSHAIGWFRQAPGKEREFVVGIN RGGVTRDYADSVKGRFAVSRDNVKNTVYLQMNRLKPEDSAIYICAARPEYSF TAMSKGDMDYWGKGTLVTVSS |

Anti vWF A1 domain VHH + anti vWF A3 domain VHH

| 2A1-4L-79/AM-4-15-3 | 20 | QVQLQDSGGRLVKAGASLRLSCAASGRTFSSLPMAWFRQAPGKEREFVAFIG SDSSTLYTSSVRGRFTISRDNGKNTVYLQMMNLKPEDTAVYYCAARSSAFSS GIYYREGSYAYWGQGTQVTVSSEPKTPKPQPAAAQVQLQDSGGGLVQPGGSL RLACAASGSIFSINSMGWYRQAPGKQRELVAHALADGSASYRDSVKGRFTIS RDNAKNTVYLQMNSLKPEDTAVYYCNTVPSSVTKGYWGQGTQVTVSS |
| 2A1-4L-79/AM-2-75 | 21 | QVQLQDSGGRLVKAGASLRLSCAASGRTFSSLPMAWFRQAPGKEREFVAFIG SDSSTLYTSSVRGRFTISRDNGKNTVYLQMMNLKPEDTAVYYCAARSSAFSS GIYYREGSYAYWGQGTQVTVSSEPKTPKPQPAAAQVQLQESGGGLVQPGGSL RLSCAASGFNFNWYPMSWVRQAPGKGLEWVSTISTYGEPRYADSVKADSPSS ETTPTTRCICNEQPETEDTAVYYCARGAGTSSYLPQRGNWDQGTQVTVSS |
| 2A1-4L-79/22-4L-16 | 22 | QVQLQDSGGRLVKAGASLRLSCAASGRTFSSLPMAWFRQAPGKEREFVAFIG SDSSTLYTSSVRGRFTISRDNGKNTVYLQMMNLKPEDTAVYYCAARSSAFSS GIYYREGSYAYWGQGTQVTVSSEPKTPKPQPAAAQVQLVESGGGLVQAGGSL RLSCAASGRTFSSYAMGWFRQAPGKEREFVAAISWSGGSTYYADSVKGRFTI SRDNAKNTVYLQMNSLKPEDTAVYYCVADTGGISWIRTQGYNYWGQGTQVTV SS |

Anti vWF A1 domain VHH

| A50 | 23 | QVQLQESGGGLVQAGGSLRLSCAASGRTFSSYRMGWFRQAPGKEREFVAAIS RRGDNVYYADSVKGRFAISRDNAESTLYLQMNSLKPEDTAVYYCAAHVTVSA ITLSTSTYDYWGQGTQVTVSS |
| I53 | 24 | QVQLQDSGGGLVQAGGSLRLSCAASGRTKDMAWFRQPPGKEREFVAVIYSSD GSTLVAASVKGRFTISRDNAKNTVYLQMTSLKPADTAVYYCATSRGYSGTYY STSRYDYWTGGTQVTVSS |
| Z29 | 25 | QVQLQESGGGSVQAGDSLTLSCAASGRTFSMHAMGWFRQAPGKEREFVAAIS PSAFTEYADSLKGRFTVSRDNAKKLVWLQMNGLKPEDTAAYYCAARRGAFTA TTAPLYDYWGQGTQVTVSS |
| M53 | 26 | QVQLQDSGGGLVQAGESLRLSCGTSGRTFGRRAMAWFRQAPGKERQFVAWIA RYDGSTLYADSVKGRFTISRDDNKNTMYLHMNNLTPEDTAVYYCAAGPRGLY YESRYEYWGQGTLVTVSS |
| 2A1-4L-79 | 27 | QVQLQDSGGRLVKAGASLRLSCAASGRTFSSLPMAWFRQAPGKEREFVAFIG SDSSTLYTSSVRGRFTISRDNGKNTVYLQMMNLKPEDTAVYYCAARSSAFSS GIYYREGSYAYWGQGTQVTVSS |

TABLE 30-continued

Amino acid sequence listing of the peptides of the present invention and of human von Willebrand factor (vWF). The sequence of human vWF indicates A1 and A3 domains respectively in bold lettering.

| NAME | SEQ ID NO | SEQUENCE |
|---|---|---|
| 2A1-4L-129 | 28 | QVQLQESGGGLVQAGASLRLSCAASGRSFSSYPMAWFRQAPGKEREFVVFIGSDHSTLYSTSVRGRFTISRDNAKNTVYLQMMNLKPEDTAVYYCAARNSAWSSGIYYRETSYDYWGQGTQVTVSS |
| 2A1-4L-34 | 29 | QVQLQDSGGGSVQAGASLRLSCAASGGTFSSYAMAWFRQAPGKEREFVGFIGSDGSTLYSSSVRGRFTISRDNAKNTVALQMMNLKPEDTAVYYCAARARYSGIYYRETDYPYWGQGTQVTVSS |
| 2A1-4L-78 | 30 | QVQLQESGGGLVQAGASLRLSCTASGRSFGGFPMGWFRQAPGKEREFVSGLTRSLFTVYADSVKGRFTVSTDNTKNTVYLQMNSLKPEDTAVYYCAARPDLYAYSRDPNEYDYWGQGTQVTVSS |
| 2LA1-15 | 31 | QVQLQDSGGGLVQSGGSLRLACAASGRIVSTYAMGWFRQSPGKEREFVATVKGRFTISRDNAKNTLYLQMNSLKPEDTAVYYCAKTKRTGIFTTARMVDYWGQGTQVTVSS |

Anti vWF A1 domain VHH: bispecific and bivalent VHH

| 2A1-4L-79/2A1-4L-79 | 32 | QVQLQDSGGRLVKAGASLRLSCAASGRTFSSLPMAWFRQAPGKEREFVAFIGSDSSTLYTSSVRGRFTISRDNGKNTVYLQMMNLKPEDTAVYYCAARSSAFSSGIYYREGSYAYWGQGTQVTVSSEPKTPKPQPAAAQVQLQDSGGRLVKAGASLRLSCAASGRTFSSLPMAWFRQAPGKEREFVAFIGSDSSTLYTSSVRGRFTISRDNGKNTVYLQMMNLKPEDTAVYYCAARSSAFSSGIYYREGSYAYWGQGTQVTVSS |
| 2LA1-15/2LA1-15 | 33 | QVQLQDSGGGLVQSGGSLRLACAASGRIVSTYAMGWFRQSPGKEREFVATVKGRFTISRDNAKNTLYLQMNSLKPEDTAVYYCAKTKRTGIFTTARMVDYWGQGTQVTVSSEPKTPKPQPAAAQVQLQDSGGGLVQSGGSLRLACAASGRIVSTYAMGWFRQSPGKEREFVATVKGRFTISRDNAKNTLYLQMNSLKPEDTAVYYCAKTKRTGIFTTARMVDYWGQGTQVTVSS |
| A50/A50 | 34 | QVQLQESGGGLVQAGGSLRLSCAASGRTFSSYRMGWFRQAPGKEREFVAAISRRGDNVYYADSVKGRFAISRDNAESTLYLQMNSLKPEDTAVYYCAAHVTVSAITLSTSTYDYWGQGTQVTVSSEPKTPKPQPAAAQVQLQESGGGLVQAGGSLRLSCAASGRTFSSYRMGWFRQAPGKEREFVAAISRRGDNVYYADSVKGRFAISRDNAESTLYLQMNSLKPEDTAVYYCAAHVTVSAITLSTSTYDYWGQGTQVTVSS |

Anti collagen VHH

| 3P1-31 | 35 | QVQLQESGGGLVQAGGSLRLSCAASGRTFRRYAMGWYRQAPGKQRELVAAITSGGRTSVADTVKGRFTISSDNAKNTVYLQMNSLKPEDAAVYYCTLYNSTTNYYNQSPSSWGQGTQVTVSS |
| 3L-41 | 36 | QVQLQDSGGGLVQAGGSLRLSCAASGRTFRRYAMGWYRQAPGKQRVLVAAITSNGRPSVADSVKGRFTISSDTAKNTVYLQMNSLKPEDTALYYCTLYNTSADYYNQSPSSWGQGTQVTVLS |
| 3P2-31 | 37 | QVQLQESGGGLVQAGDSLRLSCAASGRTFTMGWFRQAPGKERQFVAALTWTGGSPVYADSVKGRFTTWRVLDNNTVYLHMNSLKPEDTAVYHCAAARTYYGNISEYYDYWGQGTQVTVSS |

Anti-vWF VHH: humanized

| C37-3 | 38 | QVQLQESGGGLVQPGGSLRLSCAASGFNFNWYPMSWVRQAPGKGLEWVSTISTYGEPRYADSVKGRFTISRDNSKNTLYLQMNSLRAEDTAVYYCARGAGTSSYLPQRGNWDQGTQVTISS |
| C37-4 | 39 | QVQLQESGGGLVQPGGSLRLSCAASGFNFNWYPMSWVRQAPGKGLEWVSTISTYGEPRYADSVKGRFTISRDNSKNTLYLQMNSLRAEDTAVYYCAKGAGTSSYLPQRGNWDQGTQVTISS |
| C37-8 | 40 | EVQLLESGGGLVQPGGSLRLSCAASGFTFSWYPMSWVRQAPGKGLEWVSTISTYGEPRYADSVKGRFTISRDNSKNTLYLQMNSLRAEDTAVYYCAKGAGTSSYLPQRGNWDQGTQVTISS |

TABLE 30-continued

Amino acid sequence listing of the peptides of the present invention and of human von Willebrand factor (vWF). The sequence of human vWF indicates A1 and A3 domains respectively in bold lettering.

| NAME | SEQ ID NO | SEQUENCE |
|---|---|---|
| C37-10 | 41 | EVQLLESGGGLVQPGGSLRLSCAASGFTFSWYPMSWVRQAPGKGLEWVSTIS TYGEPRYADSVKGRFTISRDNSKNTLYLQMNSLRAEDTAVYYCAKGAGTSSY LPQRGNWDQGTLVTVSS |

Humanised anti- vWF VHH + anti-mouse serum albumin VHH

| NAME | SEQ ID NO | SEQUENCE |
|---|---|---|
| MSA21/ C37-hum | 42 | QVQLQESGGGLVQPGGSLRLSCEASGFTFSRFGMTWVRQAPGKGVEWSGIS SLGDSTLYADSVKGRFTISRDNAKNTLYLQMNSLKPEDTAVYYCTIGGSLNP GGQGTQVTVSSEPKTPKPQPAAAQVQLQESGGGLVQPGGSLRLSCAASGFTF SWYPMSWVRQAPGKGLEWVSTISTYGEPRYADSVKGRFTISRDNSKNTLYLQ MNSLRAEDTAVYYCAKGAGTSSYLPQRGNWDQGTQVTISS |
| MSA24/ C37-hum | 43 | QVQLQESGGGLVQPGNSLRLSCAASGFTFRNFGMSWVRQAPGKEPEWVSSIS GSGSNTIYADSVKDRFTISRDNAKSTLYLQMNSLKPEDTAVYYCTIGGSLSR SSQGTQVTVSSEPKTPKPQPAAAQVQLQESGGGLVQPGGSLRLSCAASGFTF SWYPMSWVRQAPGKGLEWVSTISTYGEPRYADSVKGRFTISRDNSKNTLYLQ MNSLRAEDTAVYYCAKGAGTSSYLPQRGNWDQGTQVTISS |
| MSA210/ C37-hum | 44 | QVQLQESGGGLVQPGGSLRLTCTASGFTFSSFGMSWVRQAPGKGLEWVSAIS SDSGTKNYADSVKGRFTISRDNAKKMLFLQMNSLRPEDTAVYYCVIGRGSPS SQGTQVTVSSEPKTPKPQPAAAQVQLQESGGGLVQPGGSLRLSCAASGFTFS WYPMSWVRQAPGKGLEWVSTISTYGEPRYADSVKGRFTISRDNSKNTLYLQM NSLRAEDTAVYYCAKGAGTSSYLPQRGNWDQGTQVTISS |
| MSA212/ C37-hum | 45 | QVQLQESGGGLVQPGGSLRLTCTASGFTFRSFGMSWVRQAPGKGLEWVSAIS ADGSDKRYADSVKGRFTISRDNGKKMLTLDMNSLKPEDTAVYYCVIGRGSPA SQGTQVTVSSEPKTPKPQPAAAQVQLQESGGGLVQPGGSLRLSCAASGFTFS WYPMSWVRQAPGKGLEWVSTISTYGEPRYADSVKGRFTISRDNSKNTLYLQM NSLRAEDTAVYYCAKGAGTSSYLPQRGNWDQGTQVTISS |

Anti collagen VHH: bispecific

| NAME | SEQ ID NO | SEQUENCE |
|---|---|---|
| 3P1-31/3P2-31 | 46 | QVQLQESGGGLVQAGGSLRLSCAASGRTFRRYAMGWYRQAPGKQRELVAAIT SGGRTSVADTVKGRFTISSDNAKNTVYLQMNSLKPEDAAVYYCTLYNSTTNY YNQSPSSWGQGTQVTVSS<u>EPKTPKPQPAAA</u>QVQLQESGGGLVQAGDSLRLSC AASGRTFTMGWFRQAPGKERQFVAALTWTGGSPVYADSVKGRFTTWRVLDNN TVYLHMNSLKPEDTAVYHCAAARTYYGNISEYYDYWGQGTQVTVSS |
| 3L-41/3P2-31 | 47 | QVQLQDSGGGLVQAGGSLRLSCAASGRTFRRYAMGWYRQAPGKQRVLVAAIT SNGRPSVADSVKGRFTISSDTAKNTVYLQMNSLKPEDTALYYCTLYNTSADY YNQSPSSWGQGTQVTVLS<u>EPKTPKPQPAAA</u>QVQLQESGGGLVQAGDSLRLSC AASGRTFTMGWFRQAPGKERQFVAALTWTGGSPVYADSVKGRFTTWRVLDNN TVYLHMNSLKPEDTAVYHCAAARTYYGNISEYYDYWGQGTQVTVSS |

Conformation-specific Anti-vWF VHH

| NAME | SEQ ID NO | SEQUENCE |
|---|---|---|
| A11 | 62 | EVQLVESGGRLVKAGASLRLSCAASGRTFSSLPMAWFRQAPGKEREFVAFIG SDSSTLYTSSVRGRFTISRDNGKNTVYLQMMNLKPEDTAVYYCAARSSAFSS GIYYREGSYAYWGQGTQVTVSS |
| A12 | 63 | QVQLVESGGGLVQAGGSLRLSCTASGRTFSTYALGWFRQVPGKGREFIAVIY WRDGSSLYSDSVKGRFTISKDNAKNTVYLQMNSLKPEDTAVYYCANRHDSRG TYYSSRGYDYWGQGTQVTVSS |
| A13 | 64 | QVQLVESGGGLVQAGGSLRLSCAASGRTKDMAWFRQPPGKEREFVAVIYSSD GSTLVAASVKGRFTISRDNAKNTVYLQMTSLKPADTAVYYCATSRGYSGTYY STSRYDYWGQGTQVTVSS |
| A15 | 65 | QVQLVESGGGLVQAGGSLRLSCAASGRTKDMAWFRQPPGKEREFVAVIYSSD GSTLVAASVTGRFTISRDNAKNMVYLQMTSLKPADTAVYYCASSRGYSGTYY STSRYDYWGQGTQVTVSS |

Human vWF

| NAME | SEQ ID NO | SEQUENCE |
|---|---|---|
| Human vWF | 48 | MIPARFAGVLLALALILPGTLCAEGTRGRSSTARCSLFGSDFVNTFDGSMYS FAGYCSYLLAGGCQKRSFSIIGDFQNGKRVSLSVYLGEFFDIHLFVNGTVTQ GDQRVSMPYASKGLYLETEAGYYKLSGEAYGFVARIDGSGNFQVLLSDRYFN |

TABLE 30-continued

Amino acid sequence listing of the peptides of the present invention and of human von Willebrand factor (vWF). The sequence of human vWF indicates A1 and A3 domains respectively in bold lettering.

| NAME | SEQ ID NO | SEQUENCE |
|---|---|---|
| | | KTCGLCGNFNIFAEDDFMTQEGTLTSDPYDFANSWALSSGEQWCERASPPSS<br>SCNISSGEMQKGLWEQCQLLKSTSVFARCHPLVDPEPFVALCEKTLCECAGG<br>LECACPALLEYARTCAQEGMVLYGWTDHSACSPVCPAGMEYRQCVSPCARTC<br>QSLHINEMCQERCVDGCSCPEGQLLDEGLCVESTECPCVHSGKRYPPGTSLS<br>RDCNTCICRNSQWICSNEECPGECLVTGQSHFKSFDNRYFTFSGICQYLLAR<br>DCQDHSFSIVIETVQCADDRDAVCTRSVTVRLPGLHNSLVKLKHGAGVAMDG<br>QDIQLPLLKGDLRIQHTVTASVRLSYGEDLQMDWDGRGRLLVKLSPVYAGKT<br>CGLCGNYNGNQGDDFLTPSGLAEPRVEDFGNAWKLHGDCQDLQKQHSDPCAL<br>NPRMTRFSEEACAVLTSPTFEACHRAVSPLPYLRNCRYDVCSCSDGRECLCG<br>ALASYAAACAGRGVRVAWREPGRCELNCPKGQVYLQCGTPCNLTCRSLSYPD<br>EECNEACLEGCFCPPGLYMDERGDCVPKAQCPCYYDGEIFQPEDIFSDHHTM<br>CYCEDGFMHCTMSGVPGSLLPDAVLSSPLSHRSKRSLSCRPPMVKLVCPADN<br>LRAEGLECTKTCQNYDLECMSMGCVSGCLCPPGMVRHENRCVALERCPCFHQ<br>GKEYAPGETVKIGCNTCVCRDRKWNCTDHVCDATCSTIGMAHYLTFDGLKYL<br>FPGECQYVLVQDYCGSNPGTFRILVGNKGCSHPSVKCKKRVTILVEGGEIEL<br>FDGEVNVKRPMKDETHFEVVESGRYIILLLGKALSVVWDRHLSISVVLKQTY<br>QEKVCGLCGNFDGIQNNDLTSSNLQVEEDPVDFGNSWKVSSQCADTRKVPLD<br>SSPATCHNNIMKQTMVDSSCRILTSDVFQDCNKLVDPEPYLDVCIYDTCSCE<br>SIGDCACFCDTIAAYAHVCAQHGKVVTWRTATLCPQSCEERNLRENGYECEW<br>RYNSCAPACQVTCQHPEPLACPVQCVEGCHAHCPPGKILDELLQTCVDPEDC<br>PVCEVAGRRFASGKKVTLNPSDPEHCQICHCDVVNLTCEACQEPGGLVVPPT<br>DAPVSPTTLYVEDISEPPLHDFYCSRLLDLVFLLDGSSRLSEAEFEVLKAFV<br>VDMMERLRISQKWVRVAVVEYHDGSHAYIGLKDRKRPSELRRIASQVKYAGS<br>QVASTSEVLKYTLFQIFSKIDRPEASRIALLLMASQEPQRMSRNFVRYVQGL<br>KKKKVIVIPVGIGPHANLKQIRLIEKQAPENKAFVLSSVDELEQQRDEIVSY<br>LCDLAPEAPPPTLPPHMAQVTVGPGLRNSMVLDVAFVLEGSDKIGEADPNRS<br>KEFMEEVIQRMDVGQDSIHVTVLQYSYMVTVEYPFSEAQSKGDILQRVREIR<br>YQGGNRTNTGLALRYLSDHSFLVSQGDREQAPNLVYMVTGNPASDEIKRLPG<br>DIQVVPIGVGPNANVQELERIGWPNAPILIQDFETLPREAPDLVLQRCCSGE<br>GLQIPTLSPAPDCSQPLDVILLLDGSSSFPASYFDEMKSFAKAFISKANIGP<br>RLTQVSVLQYGSITTIDVPWNVVPEKAHLLSLVDVMQREGGPSQIGDALGFA<br>VRYLTSEMHGARPGASKAVVILVTDVSVDSVDAAADAARSNRVTVFPIGIGD<br>RYDAAQLRILAGPAGDSNVVKLQRIEDLPTMVTLGNSFLHKLCSGFVRICMD<br>EDGNEKRPGDVWTLPDQCHTVTCQPDGQTLLKSHRVNCDRGLRPSCPNSQSP<br>VKVEETCGCRWTCPCVCTGSSTRHIVTEDGQNFKLTGSCSYVLFQNKEQDLE<br>VILHNGACSPGARQGCMKSIEVKHSALSVELHSDMEVTVNGRLVSVPYVGGN<br>MEVNVYGAIMHEVRENHLGHIFTFTPQNNEFQLQLSPKTFASKTYGLCGICD<br>ENGANDFMLRDGTVTTDWKTLVQEWTVQRPGQTCQPILEEQCLVPDSSHCQV<br>LLLPLFAECHKVLAPATFYAICQQDSCHQEQVCEVIASYAHLCRTNGVCVDW<br>RTPDFCAMSCPPSLVYNHCEHGCPRHCDGNVSSCGDHPSEGCFCPPDKVMLE<br>GSCVPEEACTQCIGEDGVQHQFLEAWVPDHQPCQICTCLSGRKVNCTTQPCP<br>TAKAPTCGLCEVARLRQNADQCCPEYECVCDPVSCDLPPVPHCERGLQPTLT<br>NPGECRPNFTCACRKEECKRVSPPSCPPHRLPTLRKTQCCDEYECACNCVNS<br>TVSCPLGYLASTATNDCGCTTTTCLPDKVCVHRSTIYPVGQFWEEGCDVCTC<br>TDMEDAVMGLRVAQCSQKPCEDSCRSGFTYVLHEGECCGRCLPSACEVVTGS<br>PRGDSQSSWKSVGSQWASPENPCLINECVRVKEEVFIQQRNVSCPQLEVPVC<br>PSGFQLSCKTSACCPSCRCERMEACMLNGTVIGPGKTVMIDVCTTCRCMVQV<br>GVISGFKLECRKTTCNPCPLGYKEENNTGECCGRCLPTACTIQLRGGQIMTL<br>KRDETLQDGCDTHFCKVNERGEYFWEKRVTGCPPFDEHKCLAEGGKIMKIPG<br>TCCDTCEEPECNDITARLQYVKVGSCKSEVEVDIHYCQGKCASKAMYSIDIN<br>DVQDQCSCCSPTRTEPMQVALHCTNGSVVYHEVLNAMECKCSPRKCSK |

TABLE 31

Results after two panning rounds on rA1 domain of vWF as described in Example 66

| | First library | Second library | Third library |
|---|---|---|---|
| Pfu rA1 | $1 \times 10^8$ | $2 \times 10^7$ | $4 \times 10^9$ |
| Pfu casein | $2 \times 10^4$ | $2 \times 10^4$ | $2 \times 10^4$ |
| Enrichment | 5.000 | 1.000 | 200.000 |

TABLE 32

ELISA analyses of selected clones for binding to rA1 and vWF as described in example 67

| | First library | Second library | Third library |
|---|---|---|---|
| ELISA rA1 | 54/64 | 51/64 | 49/64 |
| ELISA vWF | 36/64 | 35/64 | 33/64 |

The invention claimed is:

1. A nucleic acid encoding a polypeptide construct comprising at least one single domain antibody that specifically binds von Willebrand Factor (vWF), wherein the at least one single domain antibody has complementary determining regions (CDRs) and framework regions (FRs), and wherein the at least one single domain antibody comprises:

a sequence represented by any one of SEQ ID NOs: 1 to 7, 23 to 31, and 62 to 65; or a homologous sequence of any one of SEQ ID NOs: 1 to 7, 23 to 31, and 62 to 65, wherein the FRs have a sequence identity of more than 85% with the FRs of the parent sequence; or a homologous sequence of any one of SEQ ID NOs: 1 to 7, 23 to 31, and 62 to 65, wherein the FRs have up to 10 amino acid substitutions compared to the FRs of the parent sequence; and wherein the polypeptide construct is able to inhibit at least 50% of platelet aggregation at high shear (1600 s$^{-1}$) at a concentration of between 0.08 and 0.3 µg/ml.

2. A method of producing a polypeptide construct comprising:

(a) culturing host cells comprising a nucleic acid according to claim 1 under conditions allowing the expression of the polypeptide construct; and (b) recovering the produced polypeptide construct from the culture.

3. The nucleic acid according to claim 1, wherein the at least one single domain antibody comprises a sequence represented by any one of SEQ ID NOs: 1 to 7, 23 to 31, and 62 to 65.

4. A method of producing a polypeptide construct, comprising:

(a) culturing host cells comprising a nucleic acid according to claim 3 under conditions allowing the expression of the polypeptide construct; and (b) recovering the produced polypeptide construct from the culture.

* * * * *

SEQUENCE LISTING

<160> NUMBER OF SEQ ID NOS: 85

<210> SEQ ID NO 1
<211> LENGTH: 121
<212> TYPE: PRT
<213> ORGANISM: Lama glama

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asn Phe Asn Trp Tyr
            20                  25                  30

Pro Met Ser Trp Val Arg Gln Ala Pro Gly Lys Gly Leu Glu Trp Val
        35                  40                  45

Ser Thr Ile Ser Thr Tyr Gly Glu Pro Arg Tyr Ala Asp Ser Val Lys
    50                  55                  60

Gly Arg Phe Thr Ile Ser Arg Asp Asn Ala Asn Asn Thr Leu Tyr Leu
65                  70                  75                  80

Gln Met Asn Ser Leu Arg Pro Glu Asp Thr Ala Val Tyr Tyr Cys Ala
                85                  90                  95

Arg Gly Ala Gly Thr Ser Ser Tyr Leu Pro Gln Arg Gly Asn Trp Asp
            100                 105                 110

Gln Gly Thr Gln Val Thr Ile Ser Ser
        115                 120

<210> SEQ ID NO 2
<211> LENGTH: 121
<212> TYPE: PRT
<213> ORGANISM: Lama glama

<400> SEQUENCE: 2

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Pro Met Ser Trp Val Arg Gln Ala Pro Gly Lys Gly Leu Glu Trp Val
        35                  40                  45

Ser Thr Ile Ser Thr Tyr Gly Glu Pro Arg Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Ala Gly Thr Ser Ser Tyr Leu Pro Gln Arg Gly Asn Trp Asp
            100                 105                 110

Gln Gly Thr Gln Val Thr Ile Ser Ser
        115                 120

<210> SEQ ID NO 3
<211> LENGTH: 121
<212> TYPE: PRT
<213> ORGANISM: Lama glama

<400> SEQUENCE: 3

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asn Phe Asn Trp Tyr
            20                  25                  30

-continued

```
Pro Met Ser Trp Val Arg Gln Ala Pro Gly Lys Gly Leu Glu Trp Val
        35                  40                  45

Ser Thr Ile Ser Thr Tyr Gly Glu Pro Arg Tyr Ala Asp Ser Val Lys
 50                  55                  60

Gly Arg Phe Thr Ile Ser Arg Asp Asn Ala Asn Asn Thr Leu Tyr Leu
 65                  70                  75                  80

Gln Met Asn Ser Leu Arg Pro Glu Asp Thr Ala Val Tyr Tyr Cys Ala
                 85                  90                  95

Arg Gly Ala Gly Thr Ser Ser Tyr Leu Pro Gln Arg Gly Asn Trp Asp
            100                 105                 110

Gln Gly Thr Gln Val Thr Val Ser Ser
        115                 120
```

<210> SEQ ID NO 4
<211> LENGTH: 126
<212> TYPE: PRT
<213> ORGANISM: Lama glama

<400> SEQUENCE: 4

```
Gln Val Gln Leu Gln Asp Ser Gly Gly Gly Leu Val Gln Ala Gly Gly
1                5                  10                  15

Ser Leu Arg Leu Ser Cys Ala Ala Ser Val Arg Ile Phe Thr Ser Tyr
             20                  25                  30

Ala Met Gly Trp Phe Arg Gln Ala Pro Gly Lys Glu Arg Glu Phe Val
        35                  40                  45

Ala Ala Ile Asn Arg Ser Gly Lys Ser Thr Tyr Tyr Ser Asp Ser Val
 50                  55                  60

Glu Gly Arg Phe Thr Ile Ser Arg Asp Asn Ala Lys Asn Thr Val Ser
 65                  70                  75                  80

Leu Gln Met Asp Ser Leu Lys Leu Glu Asp Thr Ala Val Tyr Tyr Cys
                 85                  90                  95

Ala Ala Asp Tyr Ser Gly Ser Tyr Thr Ser Leu Trp Ser Arg Pro Glu
            100                 105                 110

Arg Leu Asp Trp Gly Gln Gly Thr Gln Val Thr Val Phe Ser
        115                 120                 125
```

<210> SEQ ID NO 5
<211> LENGTH: 124
<212> TYPE: PRT
<213> ORGANISM: Lama glama

<400> SEQUENCE: 5

```
Gln Val Gln Leu Val Glu Ser Gly Gly Gly Leu Val Gln Ala Gly Gly
1                5                  10                  15

Ser Leu Arg Leu Ser Cys Ala Ala Ser Gly Arg Thr Phe Ser Ser Tyr
             20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Val Ala Asp Thr Gly Gly Ile Ser Trp Ile Arg Thr Gln Gly Tyr Asn
            100                 105                 110
```

Tyr Trp Gly Gln Gly Thr Gln Val Thr Val Ser Ser
            115                 120

<210> SEQ ID NO 6
<211> LENGTH: 117
<212> TYPE: PRT
<213> ORGANISM: Lama glama

<400> SEQUENCE: 6

Gln Val Gln Leu Gln Glu Ser Gly Gly Gly Leu Val Gln Pro Gly Glu
1               5                   10                  15

Ser Leu Arg Leu Ser Cys Ala Ala Ser Gly Ser Ile Phe Ser Ile Asn
            20                  25                  30

Thr Met Gly Trp Tyr Gly Gln Ala Pro Gly Lys Gln Arg Glu Leu Val
        35                  40                  45

Ala Ser Ile Thr Phe Gly Gly Val Thr Asn Tyr Ala Asp Ser Val Lys
    50                  55                  60

Gly Arg Phe Thr Ile Ser Arg Asp Asn Thr Asn Asp Thr Val Tyr Leu
65                  70                  75                  80

Gln Met Asn Ser Leu Lys Pro Glu Asp Thr Ala Val Tyr Ile Cys Asn
                85                  90                  95

Ala Val Thr Trp Gly Gly Leu Thr Asn Tyr Trp Gly Gln Gly Thr Gln
            100                 105                 110

Val Thr Val Ser Ser
            115

<210> SEQ ID NO 7
<211> LENGTH: 117
<212> TYPE: PRT
<213> ORGANISM: Lama glama

<400> SEQUENCE: 7

Gln Val Gln Leu Gln Asp Ser Gly Gly Gly Leu Val Gln Pro Gly Gly
1               5                   10                  15

Ser Leu Arg Leu Ala Cys Ala Ala Ser Gly Ser Ile Phe Ser Ile Asn
            20                  25                  30

Ser Met Gly Trp Tyr Arg Gln Ala Pro Gly Lys Gln Arg Glu Leu Val
        35                  40                  45

Ala His Ala Leu Ala Asp Gly Ser Ala Ser Tyr Arg Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Thr Val Pro Ser Ser Val Thr Lys Gly Tyr Trp Gly Gln Gly Thr Gln
            100                 105                 110

Val Thr Val Ser Ser
            115

<210> SEQ ID NO 8
<211> LENGTH: 246
<212> TYPE: PRT
<213> ORGANISM: Lama glama

<400> SEQUENCE: 8

Gln Val Gln Leu Gln Asp Ser Gly Gly Gly Leu Val Gln Pro Gly Gly
1               5                   10                  15

```
Ser Leu Arg Leu Ala Cys Ala Ala Ser Gly Ser Ile Phe Ser Ile Asn
            20                  25                  30

Ser Met Gly Trp Tyr Arg Gln Ala Pro Gly Lys Gln Arg Glu Leu Val
        35                  40                  45

Ala His Ala Leu Ala Asp Gly Ser Ala Ser Tyr Arg Asp Ser Val Lys
    50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                85                  90                  95

Thr Val Pro Ser Ser Val Thr Lys Gly Tyr Trp Gly Gln Gly Thr Gln
            100                 105                 110

Val Thr Val Ser Ser Glu Pro Lys Thr Pro Lys Pro Gln Pro Ala Ala
        115                 120                 125

Ala Gln Val Gln Leu Gln Asp Ser Gly Gly Gly Leu Val Gln Pro Gly
    130                 135                 140

Gly Ser Leu Arg Leu Ala Cys Ala Ala Ser Gly Ser Ile Phe Ser Ile
145                 150                 155                 160

Asn Ser Met Gly Trp Tyr Arg Gln Ala Pro Gly Lys Gln Arg Glu Leu
                165                 170                 175

Val Ala His Ala Leu Ala Asp Gly Ser Ala Ser Tyr Arg Asp Ser Val
            180                 185                 190

Lys Gly Arg Phe Thr Ile Ser Arg Asp Asn Ala Lys Asn Thr Val Tyr
        195                 200                 205

Leu Gln Met Asn Ser Leu Lys Pro Glu Asp Thr Ala Val Tyr Tyr Cys
    210                 215                 220

Asn Thr Val Pro Ser Ser Val Thr Lys Gly Tyr Trp Gly Gln Gly Thr
225                 230                 235                 240

Gln Val Thr Val Ser Ser
                245

<210> SEQ ID NO 9
<211> LENGTH: 249
<212> TYPE: PRT
<213> ORGANISM: Lama glama

<400> SEQUENCE: 9

Gln Val Gln Leu Gln Asp Ser Gly Gly Gly Leu Val Gln Pro Gly Gly
  1               5                  10                  15

Ser Leu Arg Leu Ala Cys Ala Ala Ser Gly Ser Ile Phe Ser Ile Asn
            20                  25                  30

Ser Met Gly Trp Tyr Arg Gln Ala Pro Gly Lys Gln Arg Glu Leu Val
        35                  40                  45

Ala His Ala Leu Ala Asp Gly Ser Ala Ser Tyr Arg Asp Ser Val Lys
    50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                85                  90                  95

Thr Val Pro Ser Ser Val Thr Lys Gly Tyr Trp Gly Gln Gly Thr Gln
            100                 105                 110

Val Thr Val Ser Ser Glu Pro Lys Thr Pro Lys Pro Gln Pro Ala Ala
        115                 120                 125

Ala Gln Val Gln Leu Gln Glu Ser Gly Gly Gly Leu Val Gln Pro Gly
    130                 135                 140
```

```
Gly Ser Leu Arg Leu Ser Cys Ala Ala Ser Gly Phe Asn Phe Asn Trp
145                 150                 155                 160

Tyr Pro Met Ser Trp Val Arg Gln Ala Pro Gly Lys Gly Leu Glu Trp
                165                 170                 175

Val Ser Thr Ile Ser Thr Tyr Gly Glu Pro Arg Tyr Ala Asp Ser Val
            180                 185                 190

Lys Ala Asp Ser Pro Ser Ser Glu Thr Thr Pro Thr Thr Arg Cys Ile
        195                 200                 205

Cys Asn Glu Gln Pro Glu Thr Glu Asp Thr Ala Val Tyr Tyr Cys Ala
    210                 215                 220

Arg Gly Ala Gly Thr Ser Ser Tyr Leu Pro Gln Arg Gly Asn Trp Asp
225                 230                 235                 240

Gln Gly Thr Gln Val Thr Val Ser Ser
                245
```

<210> SEQ ID NO 10
<211> LENGTH: 250
<212> TYPE: PRT
<213> ORGANISM: Lama glama

<400> SEQUENCE: 10

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asn Phe Asn Trp Tyr
            20                  25                  30

Pro Met Ser Trp Val Arg Gln Ala Pro Gly Lys Gly Leu Glu Trp Val
        35                  40                  45

Ser Thr Ile Ser Thr Tyr Gly Glu Pro Arg Tyr Ala Asp Ser Val Lys
    50                  55                  60

Gly Arg Phe Thr Ile Ser Arg Asp Asn Ala Asn Asn Thr Leu Tyr Leu
65                  70                  75                  80

Gln Met Asn Ser Leu Arg Pro Glu Asp Thr Ala Val Tyr Tyr Cys Ala
                85                  90                  95

Arg Gly Ala Gly Thr Ser Ser Tyr Leu Pro Gln Arg Gly Asn Trp Asp
            100                 105                 110

Gln Gly Thr Gln Val Thr Val Ser Ser Glu Pro Lys Thr Pro Lys Pro
        115                 120                 125

Gln Pro Ala Ala Ala Gln Val Gln Leu Gln Asp Ser Gly Gly Gly Leu
    130                 135                 140

Val Gln Pro Gly Gly Ser Leu Arg Leu Ala Cys Ala Ala Ser Gly Ser
145                 150                 155                 160

Ile Phe Ser Ile Asn Ser Met Gly Trp Tyr Arg Gln Ala Pro Gly Lys
                165                 170                 175

Gln Arg Glu Leu Val Ala His Ala Leu Ala Asp Gly Ser Ala Ser Tyr
            180                 185                 190

Arg Asp Ser Val Lys Gly Arg Phe Thr Ile Ser Arg Asp Asn Ala Lys
        195                 200                 205

Asn Thr Val Tyr Leu Gln Met Asn Ser Leu Lys Pro Glu Asp Thr Ala
    210                 215                 220

Val Tyr Tyr Cys Asn Thr Val Pro Ser Ser Val Thr Lys Gly Tyr Trp
225                 230                 235                 240

Gly Gln Gly Thr Gln Val Thr Val Ser Ser
                245                 250
```

```
<210> SEQ ID NO 11
<211> LENGTH: 242
<212> TYPE: PRT
<213> ORGANISM: Lama glama

<400> SEQUENCE: 11
```

| | | | | | | | | | | | | | | | |
|---|---|---|---|---|---|---|---|---|---|---|---|---|---|---|---|
| Gln | Val | Gln | Leu | Gln | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Asn | Phe | Asn | Trp | Tyr |
| | | | 20 | | | | | 25 | | | | | 30 | | |
| Pro | Met | Ser | Trp | Val | Arg | Gln | Ala | Pro | Gly | Lys | Gly | Leu | Glu | Trp | Val |
| | | | 35 | | | | | 40 | | | | | 45 | | |
| Ser | Thr | Ile | Ser | Thr | Tyr | Gly | Glu | Pro | Arg | Tyr | Ala | Asp | Ser | Val | Lys |
| | 50 | | | | | 55 | | | | | 60 | | | | |
| Gly | Arg | Phe | Thr | Ile | Ser | Arg | Asp | Asn | Ala | Asn | Asn | Thr | Leu | Tyr | Leu |
| 65 | | | | | 70 | | | | | 75 | | | | | 80 |
| Gln | Met | Asn | Ser | Leu | Arg | Pro | Glu | Asp | Thr | Ala | Val | Tyr | Tyr | Cys | Ala |
| | | | | 85 | | | | | 90 | | | | | 95 | |
| Arg | Gly | Ala | Gly | Thr | Ser | Ser | Tyr | Leu | Pro | Gln | Arg | Gly | Asn | Trp | Asp |
| | | | 100 | | | | | 105 | | | | | 110 | | |
| Gln | Gly | Thr | Gln | Val | Thr | Val | Ser | Ser | Gln | Val | Gln | Leu | Gln | Glu | Ser |
| | | | 115 | | | | | 120 | | | | | 125 | | |
| Gly | Gly | Gly | Leu | Val | Gln | Pro | Gly | Gly | Ser | Leu | Arg | Leu | Ser | Cys | Ala |
| | | 130 | | | | | 135 | | | | | 140 | | | |
| Ala | Ser | Gly | Phe | Asn | Phe | Asn | Trp | Tyr | Pro | Met | Ser | Trp | Val | Arg | Gln |
| 145 | | | | | 150 | | | | | 155 | | | | | 160 |
| Ala | Pro | Gly | Lys | Gly | Leu | Glu | Trp | Val | Ser | Thr | Ile | Ser | Thr | Tyr | Gly |
| | | | | 165 | | | | | 170 | | | | | 175 | |
| Glu | Pro | Arg | Tyr | Ala | Asp | Ser | Val | Lys | Gly | Arg | Phe | Thr | Ile | Ser | Arg |
| | | | 180 | | | | | 185 | | | | | 190 | | |
| Asp | Asn | Ala | Asn | Asn | Thr | Leu | Tyr | Leu | Gln | Met | Asn | Ser | Leu | Arg | Pro |
| | | 195 | | | | | 200 | | | | | 205 | | | |
| Glu | Asp | Thr | Ala | Val | Tyr | Tyr | Cys | Ala | Arg | Gly | Ala | Gly | Thr | Ser | Ser |
| | 210 | | | | | 215 | | | | | 220 | | | | |
| Tyr | Leu | Pro | Gln | Arg | Gly | Asn | Trp | Asp | Gln | Gly | Thr | Gln | Val | Thr | Val |
| 225 | | | | | 230 | | | | | 235 | | | | | 240 |
| Ser | Ser | | | | | | | | | | | | | | |

```
<210> SEQ ID NO 12
<211> LENGTH: 257
<212> TYPE: PRT
<213> ORGANISM: Lama glama

<400> SEQUENCE: 12
```

| | | | | | | | | | | | | | | | |
|---|---|---|---|---|---|---|---|---|---|---|---|---|---|---|---|
| Gln | Val | Gln | Leu | Gln | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Asn | Phe | Asn | Trp | Tyr |
| | | | 20 | | | | | 25 | | | | | 30 | | |
| Pro | Met | Ser | Trp | Val | Arg | Gln | Ala | Pro | Gly | Lys | Gly | Leu | Glu | Trp | Val |
| | | | 35 | | | | | 40 | | | | | 45 | | |
| Ser | Thr | Ile | Ser | Thr | Tyr | Gly | Glu | Pro | Arg | Tyr | Ala | Asp | Ser | Val | Lys |
| | 50 | | | | | 55 | | | | | 60 | | | | |
| Gly | Arg | Phe | Thr | Ile | Ser | Arg | Asp | Asn | Ala | Asn | Asn | Thr | Leu | Tyr | Leu |
| 65 | | | | | 70 | | | | | 75 | | | | | 80 |
| Gln | Met | Asn | Ser | Leu | Arg | Pro | Glu | Asp | Thr | Ala | Val | Tyr | Tyr | Cys | Ala |
| | | | | 85 | | | | | 90 | | | | | 95 | |

```
Arg Gly Ala Gly Thr Ser Ser Tyr Leu Pro Gln Arg Gly Asn Trp Asp
            100                 105                 110
Gln Gly Thr Gln Val Thr Val Ser Ser Glu Pro Lys Thr Pro Lys Pro
            115                 120                 125
Gln Pro Ala Ala Ala Gln Val Gln Leu Val Glu Ser Gly Gly Gly Leu
        130                 135                 140
Val Gln Ala Gly Gly Ser Leu Arg Leu Ser Cys Ala Ala Ser Gly Arg
145                 150                 155                 160
Thr Phe Ser Ser Tyr Ala Met Gly Trp Phe Arg Gln Ala Pro Gly Lys
                165                 170                 175
Glu Arg Glu Phe Val Ala Ala Ile Ser Trp Ser Gly Ser Thr Tyr Tyr
            180                 185                 190
Tyr Ala Asp Ser Val Lys Gly Arg Phe Thr Ile Ser Arg Asp Asn Ala
        195                 200                 205
Lys Asn Thr Val Tyr Leu Gln Met Asn Ser Leu Lys Pro Glu Asp Thr
    210                 215                 220
Ala Val Tyr Tyr Cys Val Ala Asp Thr Gly Gly Ile Ser Trp Ile Arg
225                 230                 235                 240
Thr Gln Gly Tyr Asn Tyr Trp Gly Gln Gly Thr Gln Val Thr Val Ser
                245                 250                 255
Ser

<210> SEQ ID NO 13
<211> LENGTH: 246
<212> TYPE: PRT
<213> ORGANISM: Lama glama

<400> SEQUENCE: 13

Gln Val Gln Leu Gln Glu Ser Gly Gly Gly Leu Val Gln Pro Gly Gly
1               5                   10                  15
Ser Leu Arg Leu Ser Cys Glu Ala Ser Gly Phe Thr Phe Ser Arg Phe
            20                  25                  30
Gly Met Thr Trp Val Arg Gln Ala Pro Gly Lys Gly Val Glu Trp Val
        35                  40                  45
Ser Gly Ile Ser Ser Leu Gly Asp Ser Thr Leu Tyr Ala Asp Ser Val
    50                  55                  60
Lys Gly Arg Phe Thr Ser Arg Asp Asn Ala Lys Asn Thr Leu Tyr Leu
65                  70                  75                  80
Gln Met Asn Ser Leu Lys Pro Glu Asp Thr Ala Val Tyr Tyr Cys Thr
                85                  90                  95
Ile Gly Gly Ser Leu Asn Pro Gly Gly Gln Gly Thr Gln Val Thr Val
            100                 105                 110
Ser Ser Glu Pro Lys Thr Pro Lys Pro Gln Pro Ala Ala Ala Gln Val
        115                 120                 125
Gln Leu Gln Glu Ser Gly Gly Gly Leu Val Gln Pro Gly Gly Ser Leu
    130                 135                 140
Arg Leu Ser Cys Ala Ala Ser Gly Phe Asn Phe Asn Trp Tyr Pro Met
145                 150                 155                 160
Ser Trp Val Arg Gln Ala Pro Gly Lys Gly Leu Glu Trp Val Ser Thr
                165                 170                 175
Ile Ser Thr Tyr Gly Glu Pro Arg Tyr Ala Asp Ser Val Lys Ala Asp
            180                 185                 190
Ser Pro Ser Ser Glu Thr Thr Pro Thr Thr Arg Cys Ile Cys Asn Glu
        195                 200                 205
```

Gln Pro Glu Thr Glu Asp Thr Ala Val Tyr Tyr Cys Ala Arg Gly Ala
            210                 215                 220

Gly Thr Ser Ser Tyr Leu Pro Gln Arg Gly Asn Trp Asp Gln Gly Thr
225                 230                 235                 240

Gln Val Thr Val Ser Ser
            245

<210> SEQ ID NO 14
<211> LENGTH: 243
<212> TYPE: PRT
<213> ORGANISM: Lama glama

<400> SEQUENCE: 14

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
        35                  40                  45

Ser Gly Ile Ser Ser Leu Gly Asp Ser Thr Leu Tyr Ala Asp Ser Val
    50                  55                  60

Lys Gly Arg Phe Thr Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Thr
                85                  90                  95

Ile Gly Gly Ser Leu Asn Pro Gly Gly Gln Gly Thr Gln Val Thr Val
            100                 105                 110

Ser Ser Glu Pro Lys Thr Pro Lys Pro Gln Pro Ala Ala Ala Gln Val
        115                 120                 125

Gln Leu Gln Asp Ser Gly Gly Gly Leu Val Gln Pro Gly Gly Ser Leu
    130                 135                 140

Arg Leu Ala Cys Ala Ala Ser Gly Ser Ile Phe Ser Ile Asn Ser Met
145                 150                 155                 160

Gly Trp Tyr Arg Gln Ala Pro Gly Lys Gln Arg Glu Leu Val Ala His
                165                 170                 175

Ala Leu Ala Asp Gly Ser Ala Ser Tyr Arg Asp Ser Val Lys Gly Arg
            180                 185                 190

Phe Thr Ile Ser Arg Asp Asn Ala Lys Asn Thr Val Tyr Leu Gln Met
        195                 200                 205

Asn Ser Leu Lys Pro Glu Asp Thr Ala Val Tyr Tyr Cys Asn Thr Val
    210                 215                 220

Pro Ser Ser Val Thr Lys Gly Tyr Trp Gly Gln Gly Thr Gln Val Thr
225                 230                 235                 240

Val Ser Ser

<210> SEQ ID NO 15
<211> LENGTH: 250
<212> TYPE: PRT
<213> ORGANISM: Lama glama

<400> SEQUENCE: 15

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
            35                  40                  45

Ser Gly Ile Ser Ser Leu Gly Asp Ser Thr Leu Tyr Ala Asp Ser Val
    50                  55                  60

Lys Gly Arg Phe Thr Ser Arg Asp Asn Ala Lys Asn Thr Leu Tyr Leu
 65                  70                  75                  80

Gln Met Asn Ser Leu Lys Pro Glu Asp Thr Ala Val Tyr Tyr Cys Thr
                85                  90                  95

Ile Gly Gly Ser Leu Asn Pro Gly Gly Gln Gly Thr Gln Val Thr Val
            100                 105                 110

Ser Ser Glu Pro Lys Thr Pro Lys Pro Gln Pro Ala Ala Ala Gln Val
        115                 120                 125

Gln Leu Val Glu Ser Gly Gly Gly Leu Val Gln Ala Gly Gly Ser Leu
130                 135                 140

Arg Leu Ser Cys Ala Ala Ser Gly Arg Thr Phe Ser Ser Tyr Ala Met
145                 150                 155                 160

Gly Trp Phe Arg Gln Ala Pro Gly Lys Glu Arg Glu Phe Val Ala Ala
                165                 170                 175

Ile Ser Trp Ser Gly Gly Ser Thr Tyr Tyr Ala Asp Ser Val Lys Gly
            180                 185                 190

Arg Phe Thr Ile Ser Arg Asp Asn Ala Lys Asn Thr Val Tyr Leu Gln
        195                 200                 205

Met Asn Ser Leu Lys Pro Glu Asp Thr Ala Val Tyr Tyr Cys Val Ala
    210                 215                 220

Asp Thr Gly Gly Ile Ser Trp Ile Arg Thr Gln Gly Tyr Asn Tyr Trp
225                 230                 235                 240

Gly Gln Gly Thr Gln Val Thr Val Ser Ser
                245                 250

<210> SEQ ID NO 16
<211> LENGTH: 115
<212> TYPE: PRT
<213> ORGANISM: Lama glama

<400> SEQUENCE: 16

Gln Val Gln Leu Gln Glu Ser Gly Gly Gly Leu Val Gln Pro Gly Gly
 1               5                  10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
        35                  40                  45

Ser Gly Ile Ser Ser Leu Gly Asp Ser Thr Leu Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                85                  90                  95

Thr Ile Gly Gly Ser Leu Asn Pro Gly Gly Gln Gly Thr Gln Val Thr
            100                 105                 110

Val Ser Ser
        115

<210> SEQ ID NO 17
<211> LENGTH: 115
<212> TYPE: PRT
<213> ORGANISM: Lama glama

<400> SEQUENCE: 17

Gln Val Gln Leu Gln Glu Ser Gly Gly Gly Leu Val Gln Pro Gly Asn
1               5                   10                  15

Ser Leu Arg Leu Ser Cys Ala Ala Ser Gly Phe Thr Phe Arg Asn Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asn Thr Ile Tyr Ala Asp Ser Val
    50                  55                  60

Lys Asp Arg Phe Thr Ile Ser Arg Asp Asn Ala Lys Ser Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 18
<211> LENGTH: 114
<212> TYPE: PRT
<213> ORGANISM: Lama glama

<400> SEQUENCE: 18

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ala Ile Ser Ser Asp Ser Gly Thr Lys Asn Tyr Ala Asp Ser Val
    50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
                85                  90                  95

Val Ile Gly Arg Gly Ser Pro Ser Ser Gln Gly Thr Gln Val Thr Val
            100                 105                 110

Ser Ser

<210> SEQ ID NO 19
<211> LENGTH: 114
<212> TYPE: PRT
<213> ORGANISM: Lama glama

<400> SEQUENCE: 19

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ala Ile Ser Ala Asp Gly Ser Asp Lys Arg Tyr Ala Asp Ser Val
    50                  55                  60

Lys Gly Arg Phe Thr Ile Ser Arg Asp Asn Gly Lys Lys Met Leu Thr

```
65                  70                  75                  80
Leu Asp Met Asn Ser Leu Lys Pro Glu Asp Thr Ala Val Tyr Tyr Cys
                85                  90                  95

Val Ile Gly Arg Gly Ser Pro Ala Ser Gln Gly Thr Gln Val Thr Val
            100                 105                 110

Ser Ser

<210> SEQ ID NO 20
<211> LENGTH: 255
<212> TYPE: PRT
<213> ORGANISM: Lama glama

<400> SEQUENCE: 20

Gln Val Gln Leu Gln Asp Ser Gly Gly Arg Leu Val Lys Ala Gly Ala
1               5                   10                  15

Ser Leu Arg Leu Ser Cys Ala Ala Ser Gly Arg Thr Phe Ser Ser Leu
            20                  25                  30

Pro Met Ala Trp Phe Arg Gln Ala Pro Gly Lys Glu Arg Glu Phe Val
        35                  40                  45

Ala Phe Ile Gly Ser Asp Ser Ser Thr Leu Tyr Thr Ser Ser Val Arg
    50                  55                  60

Gly Arg Phe Thr Ile Ser Arg Asp Asn Gly Lys Asn Thr Val Tyr Leu
65                  70                  75                  80

Gln Met Met Asn Leu Lys Pro Glu Asp Thr Ala Val Tyr Tyr Cys Ala
                85                  90                  95

Ala Arg Ser Ser Ala Phe Ser Ser Gly Ile Tyr Tyr Arg Glu Gly Ser
            100                 105                 110

Tyr Ala Tyr Trp Gly Gln Gly Thr Gln Val Thr Val Ser Ser Glu Pro
        115                 120                 125

Lys Thr Pro Lys Pro Gln Pro Ala Ala Ala Gln Val Gln Leu Gln Asp
    130                 135                 140

Ser Gly Gly Gly Leu Val Gln Pro Gly Gly Ser Leu Arg Leu Ala Cys
145                 150                 155                 160

Ala Ala Ser Gly Ser Ile Phe Ser Ile Asn Ser Met Gly Trp Tyr Arg
                165                 170                 175

Gln Ala Pro Gly Lys Gln Arg Glu Leu Val Ala His Ala Leu Ala Asp
            180                 185                 190

Gly Ser Ala Ser Tyr Arg Asp Ser Val Lys Gly Arg Phe Thr Ile Ser
        195                 200                 205

Arg Asp Asn Ala Lys Asn Thr Val Tyr Leu Gln Met Asn Ser Leu Lys
    210                 215                 220

Pro Glu Asp Thr Ala Val Tyr Tyr Cys Asn Thr Val Pro Ser Ser Val
225                 230                 235                 240

Thr Lys Gly Tyr Trp Gly Gln Gly Thr Gln Val Thr Val Ser Ser
                245                 250                 255

<210> SEQ ID NO 21
<211> LENGTH: 258
<212> TYPE: PRT
<213> ORGANISM: Lama glama

<400> SEQUENCE: 21

Gln Val Gln Leu Gln Asp Ser Gly Gly Arg Leu Val Lys Ala Gly Ala
1               5                   10                  15

Ser Leu Arg Leu Ser Cys Ala Ala Ser Gly Arg Thr Phe Ser Ser Leu
            20                  25                  30
```

Pro Met Ala Trp Phe Arg Gln Ala Pro Gly Lys Glu Arg Glu Phe Val
            35                  40                  45

Ala Phe Ile Gly Ser Asp Ser Ser Thr Leu Tyr Thr Ser Ser Val Arg
    50                  55                  60

Gly Arg Phe Thr Ile Ser Arg Asp Asn Gly Lys Asn Thr Val Tyr Leu
65                  70                  75                  80

Gln Met Met Asn Leu Lys Pro Glu Asp Thr Ala Val Tyr Tyr Cys Ala
                85                  90                  95

Ala Arg Ser Ser Ala Phe Ser Ser Gly Ile Tyr Tyr Arg Glu Gly Ser
            100                 105                 110

Tyr Ala Tyr Trp Gly Gln Gly Thr Gln Val Thr Val Ser Ser Glu Pro
        115                 120                 125

Lys Thr Pro Lys Pro Gln Pro Ala Ala Ala Gln Val Gln Leu Gln Glu
    130                 135                 140

Ser Gly Gly Gly Leu Val Gln Pro Gly Gly Ser Leu Arg Leu Ser Cys
145                 150                 155                 160

Ala Ala Ser Gly Phe Asn Phe Asn Trp Tyr Pro Met Ser Trp Val Arg
                165                 170                 175

Gln Ala Pro Gly Lys Gly Leu Glu Trp Val Ser Thr Ile Ser Thr Tyr
            180                 185                 190

Gly Glu Pro Arg Tyr Ala Asp Ser Val Lys Ala Asp Ser Pro Ser Ser
        195                 200                 205

Glu Thr Thr Pro Thr Thr Arg Cys Ile Cys Asn Glu Gln Pro Glu Thr
    210                 215                 220

Glu Asp Thr Ala Val Tyr Tyr Cys Ala Arg Gly Ala Gly Thr Ser Ser
225                 230                 235                 240

Tyr Leu Pro Gln Arg Gly Asn Trp Asp Gln Gly Thr Gln Val Thr Val
                245                 250                 255

Ser Ser

<210> SEQ ID NO 22
<211> LENGTH: 262
<212> TYPE: PRT
<213> ORGANISM: Lama glama

<400> SEQUENCE: 22

Gln Val Gln Leu Gln Asp Ser Gly Gly Arg Leu Val Lys Ala Gly Ala
1               5                   10                  15

Ser Leu Arg Leu Ser Cys Ala Ala Ser Gly Arg Thr Phe Ser Ser Leu
            20                  25                  30

Pro Met Ala Trp Phe Arg Gln Ala Pro Gly Lys Glu Arg Glu Phe Val
        35                  40                  45

Ala Phe Ile Gly Ser Asp Ser Ser Thr Leu Tyr Thr Ser Ser Val Arg
    50                  55                  60

Gly Arg Phe Thr Ile Ser Arg Asp Asn Gly Lys Asn Thr Val Tyr Leu
65                  70                  75                  80

Gln Met Met Asn Leu Lys Pro Glu Asp Thr Ala Val Tyr Tyr Cys Ala
                85                  90                  95

Ala Arg Ser Ser Ala Phe Ser Ser Gly Ile Tyr Tyr Arg Glu Gly Ser
            100                 105                 110

Tyr Ala Tyr Trp Gly Gln Gly Thr Gln Val Thr Val Ser Ser Glu Pro
        115                 120                 125

Lys Thr Pro Lys Pro Gln Pro Ala Ala Ala Gln Val Gln Leu Val Glu
    130                 135                 140

Ser Gly Gly Gly Leu Val Gln Ala Gly Gly Ser Leu Arg Leu Ser Cys
145                 150                 155                 160

Ala Ala Ser Gly Arg Thr Phe Ser Ser Tyr Ala Met Gly Trp Phe Arg
                165                 170                 175

Gln Ala Pro Gly Lys Glu Arg Glu Phe Val Ala Ala Ile Ser Trp Ser
            180                 185                 190

Gly Gly Ser Thr Tyr Tyr Ala Asp Ser Val Lys Gly Arg Phe Thr Ile
        195                 200                 205

Ser Arg Asp Asn Ala Lys Asn Thr Val Tyr Leu Gln Met Asn Ser Leu
    210                 215                 220

Lys Pro Glu Asp Thr Ala Val Tyr Tyr Cys Val Ala Asp Thr Gly Gly
225                 230                 235                 240

Ile Ser Trp Ile Arg Thr Gln Gly Tyr Asn Tyr Trp Gly Gln Gly Thr
                245                 250                 255

Gln Val Thr Val Ser Ser
            260

<210> SEQ ID NO 23
<211> LENGTH: 125
<212> TYPE: PRT
<213> ORGANISM: Lama glama

<400> SEQUENCE: 23

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Arg Met Gly Trp Phe Arg Gln Ala Pro Gly Lys Glu Arg Glu Phe Val
        35                  40                  45

Ala Ala Ile Ser Arg Arg Gly Asp Asn Val Tyr Tyr Ala Asp Ser Val
    50                  55                  60

Lys Gly Arg Phe Ala Ile Ser Arg Asp Asn Ala Glu Ser Thr Leu Tyr
65                  70                  75                  80

Leu Gln Met Asn Ser Leu Lys Pro Glu Asp Thr Ala Val Tyr Tyr Cys
                85                  90                  95

Ala Ala His Val Thr Val Ser Ala Ile Thr Leu Ser Thr Ser Thr Tyr
            100                 105                 110

Asp Tyr Trp Gly Gln Gly Thr Gln Val Thr Val Ser Ser
        115                 120                 125

<210> SEQ ID NO 24
<211> LENGTH: 122
<212> TYPE: PRT
<213> ORGANISM: Lama glama

<400> SEQUENCE: 24

Gln Val Gln Leu Gln Asp Ser Gly Gly Gly Leu Val Gln Ala Gly Gly
1               5                   10                  15

Ser Leu Arg Leu Ser Cys Ala Ala Ser Gly Arg Thr Lys Asp Met Ala
            20                  25                  30

Trp Phe Arg Gln Pro Pro Gly Lys Glu Arg Glu Phe Val Ala Val Ile
        35                  40                  45

Tyr Ser Ser Asp Gly Ser Thr Leu Val Ala Ser Val Lys Gly Arg
    50                  55                  60

Phe Thr Ile Ser Arg Asp Asn Ala Lys Asn Thr Val Tyr Leu Gln Met
65                  70                  75                  80

Thr Ser Leu Lys Pro Ala Asp Thr Ala Val Tyr Tyr Cys Ala Thr Ser
            85                  90                  95

Arg Gly Tyr Ser Gly Thr Tyr Tyr Ser Thr Ser Arg Tyr Asp Tyr Trp
            100                 105                 110

Thr Gly Gly Thr Gln Val Thr Val Ser Ser
            115                 120

<210> SEQ ID NO 25
<211> LENGTH: 123
<212> TYPE: PRT
<213> ORGANISM: Lama glama

<400> SEQUENCE: 25

Gln Val Gln Leu Gln Glu Ser Gly Gly Gly Ser Val Gln Ala Gly Asp
1               5                   10                  15

Ser Leu Thr Leu Ser Cys Ala Ala Ser Gly Arg Thr Phe Ser Met His
            20                  25                  30

Ala Met Gly Trp Phe Arg Gln Ala Pro Gly Lys Glu Arg Glu Phe Val
            35                  40                  45

Ala Ala Ile Ser Pro Ser Ala Phe Thr Glu Tyr Ala Asp Ser Leu Lys
        50                  55                  60

Gly Arg Phe Thr Val Ser Arg Asp Asn Ala Lys Lys Leu Val Trp Leu
65                  70                  75                  80

Gln Met Asn Gly Leu Lys Pro Glu Asp Thr Ala Ala Tyr Tyr Cys Ala
                85                  90                  95

Ala Arg Arg Gly Ala Phe Thr Ala Thr Thr Ala Pro Leu Tyr Asp Tyr
            100                 105                 110

Trp Gly Gln Gly Thr Gln Val Thr Val Ser Ser
            115                 120

<210> SEQ ID NO 26
<211> LENGTH: 122
<212> TYPE: PRT
<213> ORGANISM: Lama glama

<400> SEQUENCE: 26

Gln Val Gln Leu Gln Asp Ser Gly Gly Gly Leu Val Gln Ala Gly Glu
1               5                   10                  15

Ser Leu Arg Leu Ser Cys Gly Ser Gly Arg Thr Phe Gly Arg Arg
            20                  25                  30

Ala Met Ala Trp Phe Arg Gln Ala Pro Gly Lys Glu Arg Gln Phe Val
            35                  40                  45

Ala Trp Ile Ala Arg Tyr Asp Gly Ser Thr Leu Tyr Ala Asp Ser Val
        50                  55                  60

Lys Gly Arg Phe Thr Ile Ser Arg Asp Asp Asn Lys Asn Thr Met Tyr
65                  70                  75                  80

Leu His Met Asn Asn Leu Thr Pro Glu Asp Thr Ala Val Tyr Tyr Cys
                85                  90                  95

Ala Ala Gly Pro Arg Gly Leu Tyr Tyr Glu Ser Arg Tyr Glu Tyr Trp
            100                 105                 110

Gly Gln Gly Thr Leu Val Thr Val Ser Ser
            115                 120

<210> SEQ ID NO 27
<211> LENGTH: 126
<212> TYPE: PRT
<213> ORGANISM: Lama glama

<400> SEQUENCE: 27

Gln Val Gln Leu Gln Asp Ser Gly Gly Arg Leu Val Lys Ala Gly Ala
1               5                   10                  15

Ser Leu Arg Leu Ser Cys Ala Ala Ser Gly Arg Thr Phe Ser Ser Leu
            20                  25                  30

Pro Met Ala Trp Phe Arg Gln Ala Pro Gly Lys Glu Arg Glu Phe Val
        35                  40                  45

Ala Phe Ile Gly Ser Asp Ser Ser Thr Leu Tyr Thr Ser Ser Val Arg
    50                  55                  60

Gly Arg Phe Thr Ile Ser Arg Asp Asn Gly Lys Asn Thr Val Tyr Leu
65                  70                  75                  80

Gln Met Met Asn Leu Lys Pro Glu Asp Thr Ala Val Tyr Tyr Cys Ala
                85                  90                  95

Ala Arg Ser Ser Ala Phe Ser Ser Gly Ile Tyr Tyr Arg Glu Gly Ser
            100                 105                 110

Tyr Ala Tyr Trp Gly Gln Gly Thr Gln Val Thr Val Ser Ser
        115                 120                 125

<210> SEQ ID NO 28
<211> LENGTH: 126
<212> TYPE: PRT
<213> ORGANISM: Lama glama

<400> SEQUENCE: 28

Gln Val Gln Leu Gln Glu Ser Gly Gly Gly Leu Val Gln Ala Gly Ala
1               5                   10                  15

Ser Leu Arg Leu Ser Cys Ala Ala Ser Gly Arg Ser Phe Ser Ser Tyr
            20                  25                  30

Pro Met Ala Trp Phe Arg Gln Ala Pro Gly Lys Glu Arg Glu Phe Val
        35                  40                  45

Val Phe Ile Gly Ser Asp His Ser Thr Leu Tyr Ser Thr Ser Val Arg
    50                  55                  60

Gly Arg Phe Thr Ile Ser Arg Asp Asn Ala Lys Asn Thr Val Tyr Leu
65                  70                  75                  80

Gln Met Met Asn Leu Lys Pro Glu Asp Thr Ala Val Tyr Tyr Cys Ala
                85                  90                  95

Ala Arg Asn Ser Ala Trp Ser Ser Gly Ile Tyr Tyr Arg Glu Thr Ser
            100                 105                 110

Tyr Asp Tyr Trp Gly Gln Gly Thr Gln Val Thr Val Ser Ser
        115                 120                 125

<210> SEQ ID NO 29
<211> LENGTH: 124
<212> TYPE: PRT
<213> ORGANISM: Lama glama

<400> SEQUENCE: 29

Gln Val Gln Leu Gln Asp Ser Gly Gly Ser Val Gln Ala Gly Ala
1               5                   10                  15

Ser Leu Arg Leu Ser Cys Ala Ala Ser Gly Gly Thr Phe Ser Ser Tyr
            20                  25                  30

Ala Met Ala Trp Phe Arg Gln Ala Pro Gly Lys Glu Arg Glu Phe Val
        35                  40                  45

Gly Phe Ile Gly Ser Asp Gly Ser Thr Leu Tyr Ser Ser Ser Val Arg
    50                  55                  60

Gly Arg Phe Thr Ile Ser Arg Asp Asn Ala Lys Asn Thr Val Ala Leu
65                  70                  75                  80

Gln Met Met Asn Leu Lys Pro Glu Asp Thr Ala Val Tyr Tyr Cys Ala
                85                  90                  95

Ala Arg Ala Arg Tyr Ser Gly Ile Tyr Tyr Arg Glu Thr Asp Tyr Pro
            100                 105                 110

Tyr Trp Gly Gln Gly Thr Gln Val Thr Val Ser Ser
            115                 120

<210> SEQ ID NO 30
<211> LENGTH: 124
<212> TYPE: PRT
<213> ORGANISM: Lama glama

<400> SEQUENCE: 30

Gln Val Gln Leu Gln Glu Ser Gly Gly Gly Leu Val Gln Ala Gly Ala
1               5                   10                  15

Ser Leu Arg Leu Ser Cys Thr Ala Ser Gly Arg Ser Phe Gly Gly Phe
            20                  25                  30

Pro Met Gly Trp Phe Arg Gln Ala Pro Gly Lys Glu Arg Glu Phe Val
        35                  40                  45

Ser Gly Leu Thr Arg Ser Leu Phe Thr Val Tyr Ala Asp Ser Val Lys
    50                  55                  60

Gly Arg Phe Thr Val Ser Thr Asp Asn Thr Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Pro Asp Leu Tyr Ala Tyr Ser Arg Asp Pro Asn Glu Tyr Asp
            100                 105                 110

Tyr Trp Gly Gln Gly Thr Gln Val Thr Val Ser Ser
            115                 120

<210> SEQ ID NO 31
<211> LENGTH: 111
<212> TYPE: PRT
<213> ORGANISM: Lama glama

<400> SEQUENCE: 31

Gln Val Gln Leu Gln Asp Ser Gly Gly Gly Leu Val Gln Ser Gly Gly
1               5                   10                  15

Ser Leu Arg Leu Ala Cys Ala Ala Ser Gly Arg Ile Val Ser Thr Tyr
            20                  25                  30

Ala Met Gly Trp Phe Arg Gln Ser Pro Gly Lys Glu Arg Glu Phe Val
        35                  40                  45

Ala Thr Val Lys Gly Arg Phe Thr Ile Ser Arg Asp Asn Ala Lys Asn
    50                  55                  60

Thr Leu Tyr Leu Gln Met Asn Ser Leu Lys Pro Glu Asp Thr Ala Val
65                  70                  75                  80

Tyr Tyr Cys Ala Lys Thr Lys Arg Thr Gly Ile Phe Thr Thr Ala Arg
                85                  90                  95

Met Val Asp Tyr Trp Gly Gln Gly Thr Gln Val Thr Val Ser Ser
            100                 105                 110

<210> SEQ ID NO 32
<211> LENGTH: 264
<212> TYPE: PRT
<213> ORGANISM: Lama glama

<400> SEQUENCE: 32

```
Gln Val Gln Leu Gln Asp Ser Gly Gly Arg Leu Val Lys Ala Gly Ala
1               5                   10                  15

Ser Leu Arg Leu Ser Cys Ala Ala Ser Gly Arg Thr Phe Ser Ser Leu
            20                  25                  30

Pro Met Ala Trp Phe Arg Gln Ala Pro Gly Lys Glu Arg Glu Phe Val
        35                  40                  45

Ala Phe Ile Gly Ser Asp Ser Thr Leu Tyr Thr Ser Ser Val Arg
    50                  55                  60

Gly Arg Phe Thr Ile Ser Arg Asp Asn Gly Lys Asn Thr Val Tyr Leu
65                  70                  75                  80

Gln Met Met Asn Leu Lys Pro Glu Asp Thr Ala Val Tyr Tyr Cys Ala
                85                  90                  95

Ala Arg Ser Ser Ala Phe Ser Ser Gly Ile Tyr Tyr Arg Glu Gly Ser
            100                 105                 110

Tyr Ala Tyr Trp Gly Gln Gly Thr Gln Val Thr Val Ser Ser Glu Pro
        115                 120                 125

Lys Thr Pro Lys Pro Gln Pro Ala Ala Ala Gln Val Gln Leu Gln Asp
130                 135                 140

Ser Gly Gly Arg Leu Val Lys Ala Gly Ala Ser Leu Arg Leu Ser Cys
145                 150                 155                 160

Ala Ala Ser Gly Arg Thr Phe Ser Ser Leu Pro Met Ala Trp Phe Arg
                165                 170                 175

Gln Ala Pro Gly Lys Glu Arg Glu Phe Val Ala Phe Ile Gly Ser Asp
            180                 185                 190

Ser Ser Thr Leu Tyr Thr Ser Ser Val Arg Gly Arg Phe Thr Ile Ser
        195                 200                 205

Arg Asp Asn Gly Lys Asn Thr Val Tyr Leu Gln Met Met Asn Leu Lys
    210                 215                 220

Pro Glu Asp Thr Ala Val Tyr Tyr Cys Ala Ala Arg Ser Ser Ala Phe
225                 230                 235                 240

Ser Ser Gly Ile Tyr Tyr Arg Glu Gly Ser Tyr Ala Tyr Trp Gly Gln
                245                 250                 255

Gly Thr Gln Val Thr Val Ser Ser
            260
```

<210> SEQ ID NO 33
<211> LENGTH: 234
<212> TYPE: PRT
<213> ORGANISM: Lama glama

<400> SEQUENCE: 33

```
Gln Val Gln Leu Gln Asp Ser Gly Gly Gly Leu Val Gln Ser Gly Gly
1               5                   10                  15

Ser Leu Arg Leu Ala Cys Ala Ala Ser Gly Arg Ile Val Ser Thr Tyr
            20                  25                  30

Ala Met Gly Trp Phe Arg Gln Ser Pro Gly Lys Glu Arg Glu Phe Val
        35                  40                  45

Ala Thr Val Lys Gly Arg Phe Thr Ile Ser Arg Asp Asn Ala Lys Asn
    50                  55                  60

Thr Leu Tyr Leu Gln Met Asn Ser Leu Lys Pro Glu Asp Thr Ala Val
65                  70                  75                  80

Tyr Tyr Cys Ala Lys Thr Lys Arg Thr Gly Ile Phe Thr Thr Ala Arg
                85                  90                  95
```

Met Val Asp Tyr Trp Gly Gln Gly Thr Gln Val Thr Val Ser Ser Glu
            100                 105                 110

Pro Lys Thr Pro Lys Pro Gln Pro Ala Ala Gln Val Gln Leu Gln
            115                 120                 125

Asp Ser Gly Gly Gly Leu Val Gln Ser Gly Gly Ser Leu Arg Leu Ala
        130                 135                 140

Cys Ala Ala Ser Gly Arg Ile Val Ser Thr Tyr Ala Met Gly Trp Phe
145                 150                 155                 160

Arg Gln Ser Pro Gly Lys Glu Arg Glu Phe Val Ala Thr Val Lys Gly
                165                 170                 175

Arg Phe Thr Ile Ser Arg Asp Asn Ala Lys Asn Thr Leu Tyr Leu Gln
            180                 185                 190

Met Asn Ser Leu Lys Pro Glu Asp Thr Ala Val Tyr Tyr Cys Ala Lys
        195                 200                 205

Thr Lys Arg Thr Gly Ile Phe Thr Thr Ala Arg Met Val Asp Tyr Trp
210                 215                 220

Gly Gln Gly Thr Gln Val Thr Val Ser Ser
225                 230

<210> SEQ ID NO 34
<211> LENGTH: 262
<212> TYPE: PRT
<213> ORGANISM: Lama glama

<400> SEQUENCE: 34

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Arg Met Gly Trp Phe Arg Gln Ala Pro Gly Lys Glu Arg Glu Phe Val
        35                  40                  45

Ala Ala Ile Ser Arg Arg Gly Asp Asn Val Tyr Tyr Ala Asp Ser Val
    50                  55                  60

Lys Gly Arg Phe Ala Ile Ser Arg Asp Asn Ala Glu Ser Thr Leu Tyr
65                  70                  75                  80

Leu Gln Met Asn Ser Leu Lys Pro Glu Asp Thr Ala Val Tyr Tyr Cys
                85                  90                  95

Ala Ala His Val Thr Val Ser Ala Ile Thr Leu Ser Thr Ser Thr Tyr
            100                 105                 110

Asp Tyr Trp Gly Gln Gly Thr Gln Val Thr Val Ser Ser Glu Pro Lys
        115                 120                 125

Thr Pro Lys Pro Gln Pro Ala Ala Ala Gln Val Gln Leu Gln Glu Ser
    130                 135                 140

Gly Gly Gly Leu Val Gln Ala Gly Gly Ser Leu Arg Leu Ser Cys Ala
145                 150                 155                 160

Ala Ser Gly Arg Thr Phe Ser Ser Tyr Arg Met Gly Trp Phe Arg Gln
                165                 170                 175

Ala Pro Gly Lys Glu Arg Glu Phe Val Ala Ala Ile Ser Arg Arg Gly
            180                 185                 190

Asp Asn Val Tyr Tyr Ala Asp Ser Val Lys Gly Arg Phe Ala Ile Ser
        195                 200                 205

Arg Asp Asn Ala Glu Ser Thr Leu Tyr Leu Gln Met Asn Ser Leu Lys
    210                 215                 220

Pro Glu Asp Thr Ala Val Tyr Tyr Cys Ala Ala His Val Thr Val Ser
225                 230                 235                 240

Ala Ile Thr Leu Ser Thr Ser Thr Tyr Asp Tyr Trp Gly Gln Gly Thr
            245                 250                 255

Gln Val Thr Val Ser Ser
        260

<210> SEQ ID NO 35
<211> LENGTH: 122
<212> TYPE: PRT
<213> ORGANISM: Lama glama

<400> SEQUENCE: 35

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Arg Arg Tyr
            20                  25                  30

Ala Met Gly Trp Tyr Arg Gln Ala Pro Gly Lys Gln Arg Glu Leu Val
        35                  40                  45

Ala Ala Ile Thr Ser Gly Gly Arg Thr Ser Val Ala Asp Thr Val Lys
    50                  55                  60

Gly Arg Phe Thr Ile Ser Ser Asp Asn Ala Lys Asn Thr Val Tyr Leu
65                  70                  75                  80

Gln Met Asn Ser Leu Lys Pro Glu Asp Ala Ala Val Tyr Tyr Cys Thr
                85                  90                  95

Leu Tyr Asn Ser Thr Thr Asn Tyr Tyr Asn Gln Ser Pro Ser Ser Trp
            100                 105                 110

Gly Gln Gly Thr Gln Val Thr Val Ser Ser
        115                 120

<210> SEQ ID NO 36
<211> LENGTH: 122
<212> TYPE: PRT
<213> ORGANISM: Lama glama

<400> SEQUENCE: 36

Gln Val Gln Leu Gln Asp Ser Gly Gly Gly Leu Val Gln Ala Gly Gly
1               5                   10                  15

Ser Leu Arg Leu Ser Cys Ala Ala Ser Gly Arg Thr Phe Arg Arg Tyr
            20                  25                  30

Ala Met Gly Trp Tyr Arg Gln Ala Pro Gly Lys Gln Arg Val Leu Val
        35                  40                  45

Ala Ala Ile Thr Ser Asn Gly Arg Pro Ser Val Ala Asp Ser Val Lys
    50                  55                  60

Gly Arg Phe Thr Ile Ser Ser Asp Thr Ala Lys Asn Thr Val Tyr Leu
65                  70                  75                  80

Gln Met Asn Ser Leu Lys Pro Glu Asp Thr Ala Leu Tyr Tyr Cys Thr
                85                  90                  95

Leu Tyr Asn Thr Ser Ala Asp Tyr Tyr Asn Gln Ser Pro Ser Ser Trp
            100                 105                 110

Gly Gln Gly Thr Gln Val Thr Val Leu Ser
        115                 120

<210> SEQ ID NO 37
<211> LENGTH: 120
<212> TYPE: PRT
<213> ORGANISM: Lama glama

<400> SEQUENCE: 37

-continued

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Gln Phe Val Ala Ala Leu
            35                  40                  45

Thr Trp Thr Gly Gly Ser Pro Val Tyr Ala Asp Ser Val Lys Gly Arg
        50                  55                  60

Phe Thr Thr Trp Arg Val Leu Asp Asn Asn Thr Val Tyr Leu His Met
65                  70                  75                  80

Asn Ser Leu Lys Pro Glu Asp Thr Ala Val Tyr His Cys Ala Ala Ala
                85                  90                  95

Arg Thr Tyr Tyr Gly Asn Ile Ser Glu Tyr Tyr Asp Tyr Trp Gly Gln
            100                 105                 110

Gly Thr Gln Val Thr Val Ser Ser
            115                 120

<210> SEQ ID NO 38
<211> LENGTH: 121
<212> TYPE: PRT
<213> ORGANISM: Lama glama

<400> SEQUENCE: 38

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asn Phe Asn Trp Tyr
            20                  25                  30

Pro Met Ser Trp Val Arg Gln Ala Pro Gly Lys Gly Leu Glu Trp Val
            35                  40                  45

Ser Thr Ile Ser Thr Tyr Gly Glu Pro Arg Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ala Gly Thr Ser Ser Tyr Leu Pro Gln Arg Gly Asn Trp Asp
            100                 105                 110

Gln Gly Thr Gln Val Thr Ile Ser Ser
            115                 120

<210> SEQ ID NO 39
<211> LENGTH: 121
<212> TYPE: PRT
<213> ORGANISM: Lama glama

<400> SEQUENCE: 39

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asn Phe Asn Trp Tyr
            20                  25                  30

Pro Met Ser Trp Val Arg Gln Ala Pro Gly Lys Gly Leu Glu Trp Val
            35                  40                  45

Ser Thr Ile Ser Thr Tyr Gly Glu Pro Arg Tyr Ala Asp Ser Val Lys
        50                  55                  60

Gly Arg Phe Thr Ile Ser Arg Asp Asn Ser Lys Asn Thr Leu Tyr Leu
65                  70                  75                  80

```
Gln Met Asn Ser Leu Arg Ala Glu Asp Thr Ala Val Tyr Tyr Cys Ala
                85                  90                  95

Lys Gly Ala Gly Thr Ser Ser Tyr Leu Pro Gln Arg Gly Asn Trp Asp
            100                 105                 110

Gln Gly Thr Gln Val Thr Ile Ser Ser
        115                 120

<210> SEQ ID NO 40
<211> LENGTH: 121
<212> TYPE: PRT
<213> ORGANISM: Lama glama

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Pro Met Ser Trp Val Arg Gln Ala Pro Gly Lys Gly Leu Glu Trp Val
            35                  40                  45

Ser Thr Ile Ser Thr Tyr Gly Glu Pro Arg Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Ala Gly Thr Ser Ser Tyr Leu Pro Gln Arg Gly Asn Trp Asp
            100                 105                 110

Gln Gly Thr Gln Val Thr Ile Ser Ser
        115                 120

<210> SEQ ID NO 41
<211> LENGTH: 121
<212> TYPE: PRT
<213> ORGANISM: Lama glama

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Pro Met Ser Trp Val Arg Gln Ala Pro Gly Lys Gly Leu Glu Trp Val
            35                  40                  45

Ser Thr Ile Ser Thr Tyr Gly Glu Pro Arg Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Ala Gly Thr Ser Ser Tyr Leu Pro Gln Arg Gly Asn Trp Asp
            100                 105                 110

Gln Gly Thr Leu Val Thr Val Ser Ser
        115                 120

<210> SEQ ID NO 42
<211> LENGTH: 248
<212> TYPE: PRT
<213> ORGANISM: Lama glama
```

<400> SEQUENCE: 42

```
Gln Val Gln Leu Gln Glu Ser Gly Gly Gly Leu Val Gln Pro Gly Gly
1               5                   10                  15
Ser Leu Arg Leu Ser Cys Glu Ala Ser Gly Phe Thr Phe Ser Arg Phe
            20                  25                  30
Gly Met Thr Trp Val Arg Gln Ala Pro Gly Lys Gly Val Glu Trp Val
        35                  40                  45
Ser Gly Ile Ser Ser Leu Gly Asp Ser Thr Leu Tyr Ala Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Pro Glu Asp Thr Ala Val Tyr Tyr Cys
                85                  90                  95
Thr Ile Gly Gly Ser Leu Asn Pro Gly Gly Gln Gly Thr Gln Val Thr
            100                 105                 110
Val Ser Ser Glu Pro Lys Thr Pro Lys Pro Gln Pro Ala Ala Ala Gln
        115                 120                 125
Val Gln Leu Gln Glu Ser Gly Gly Gly Leu Val Gln Pro Gly Gly Ser
    130                 135                 140
Leu Arg Leu Ser Cys Ala Ala Ser Gly Phe Thr Phe Ser Trp Tyr Pro
145                 150                 155                 160
Met Ser Trp Val Arg Gln Ala Pro Gly Lys Gly Leu Glu Trp Val Ser
                165                 170                 175
Thr Ile Ser Thr Tyr Gly Glu Pro Arg Tyr Ala Asp Ser Val Lys Gly
            180                 185                 190
Arg Phe Thr Ile Ser Arg Asp Asn Ser Lys Asn Thr Leu Tyr Leu Gln
        195                 200                 205
Met Asn Ser Leu Arg Ala Glu Asp Thr Ala Val Tyr Tyr Cys Ala Lys
    210                 215                 220
Gly Ala Gly Thr Ser Ser Tyr Leu Pro Gln Arg Gly Asn Trp Asp Gln
225                 230                 235                 240
Gly Thr Gln Val Thr Ile Ser Ser
                245
```

<210> SEQ ID NO 43
<211> LENGTH: 248
<212> TYPE: PRT
<213> ORGANISM: Lama glama

<400> SEQUENCE: 43

```
Gln Val Gln Leu Gln Glu Ser Gly Gly Gly Leu Val Gln Pro Gly Asn
1               5                   10                  15
Ser Leu Arg Leu Ser Cys Ala Ala Ser Gly Phe Thr Phe Arg Asn Phe
            20                  25                  30
Gly Met Ser Trp Val Arg Gln Ala Pro Gly Lys Glu Pro Glu Trp Val
        35                  40                  45
Ser Ser Ile Ser Gly Ser Gly Ser Asn Thr Ile Tyr Ala Asp Ser Val
    50                  55                  60
Lys Asp Arg Phe Thr Ile Ser Arg Asp Asn Ala Lys Ser Thr Leu Tyr
65                  70                  75                  80
Leu Gln Met Asn Ser Leu Lys Pro Glu Asp Thr Ala Val Tyr Tyr Cys
                85                  90                  95
Thr Ile Gly Gly Ser Leu Ser Arg Ser Ser Gln Gly Thr Gln Val Thr
            100                 105                 110
```

Val Ser Ser Glu Pro Lys Thr Pro Lys Pro Gln Pro Ala Ala Ala Gln
            115                 120                 125

Val Gln Leu Gln Glu Ser Gly Gly Gly Leu Val Gln Pro Gly Gly Ser
130                 135                 140

Leu Arg Leu Ser Cys Ala Ala Ser Gly Phe Thr Phe Ser Trp Tyr Pro
145                 150                 155                 160

Met Ser Trp Val Arg Gln Ala Pro Gly Lys Gly Leu Glu Trp Val Ser
                165                 170                 175

Thr Ile Ser Thr Tyr Gly Glu Pro Arg Tyr Ala Asp Ser Val Lys Gly
            180                 185                 190

Arg Phe Thr Ile Ser Arg Asp Asn Ser Lys Asn Thr Leu Tyr Leu Gln
            195                 200                 205

Met Asn Ser Leu Arg Ala Glu Asp Thr Ala Val Tyr Tyr Cys Ala Lys
    210                 215                 220

Gly Ala Gly Thr Ser Ser Tyr Leu Pro Gln Arg Gly Asn Trp Asp Gln
225                 230                 235                 240

Gly Thr Gln Val Thr Ile Ser Ser
            245

<210> SEQ ID NO 44
<211> LENGTH: 247
<212> TYPE: PRT
<213> ORGANISM: Lama glama

<400> SEQUENCE: 44

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ala Ile Ser Ser Asp Ser Gly Thr Lys Asn Tyr Ala Asp Ser Val
    50                  55                  60

Lys Gly Arg Phe Thr Ile Ser Arg Asp Asn Ala Lys Lys Met Leu Phe
65                  70                  75                  80

Leu Gln Met Asn Ser Leu Arg Pro Glu Asp Thr Ala Val Tyr Tyr Cys
                85                  90                  95

Val Ile Gly Arg Gly Ser Pro Ser Gln Gly Thr Gln Val Thr Val
                100                 105                 110

Ser Ser Glu Pro Lys Thr Pro Lys Pro Gln Pro Ala Ala Ala Gln Val
            115                 120                 125

Gln Leu Gln Glu Ser Gly Gly Gly Leu Val Gln Pro Gly Gly Ser Leu
130                 135                 140

Arg Leu Ser Cys Ala Ala Ser Gly Phe Thr Phe Ser Trp Tyr Pro Met
145                 150                 155                 160

Ser Trp Val Arg Gln Ala Pro Gly Lys Gly Leu Glu Trp Val Ser Thr
                165                 170                 175

Ile Ser Thr Tyr Gly Glu Pro Arg Tyr Ala Asp Ser Val Lys Gly Arg
            180                 185                 190

Phe Thr Ile Ser Arg Asp Asn Ser Lys Asn Thr Leu Tyr Leu Gln Met
            195                 200                 205

Asn Ser Leu Arg Ala Glu Asp Thr Ala Val Tyr Tyr Cys Ala Lys Gly
    210                 215                 220

Ala Gly Thr Ser Ser Tyr Leu Pro Gln Arg Gly Asn Trp Asp Gln Gly
225                 230                 235                 240

```
Thr Gln Val Thr Ile Ser Ser
                245

<210> SEQ ID NO 45
<211> LENGTH: 247
<212> TYPE: PRT
<213> ORGANISM: Lama glama

<400> SEQUENCE: 45

Gln Val Gln Leu Gln Glu Ser Gly Gly Gly Leu Val Gln Pro Gly Gly
1               5                   10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ala Ile Ser Ala Asp Gly Ser Asp Lys Arg Tyr Ala Asp Ser Val
    50                  55                  60

Lys Gly Arg Phe Thr Ile Ser Arg Asp Asn Gly Lys Lys Met Leu Thr
65                  70                  75                  80

Leu Asp Met Asn Ser Leu Lys Pro Glu Asp Thr Ala Val Tyr Tyr Cys
                85                  90                  95

Val Ile Gly Arg Gly Ser Pro Ala Ser Gln Gly Thr Gln Val Thr Val
            100                 105                 110

Ser Ser Glu Pro Lys Thr Pro Lys Pro Gln Pro Ala Ala Ala Gln Val
        115                 120                 125

Gln Leu Gln Glu Ser Gly Gly Gly Leu Val Gln Pro Gly Gly Ser Leu
    130                 135                 140

Arg Leu Ser Cys Ala Ala Ser Gly Phe Thr Phe Ser Trp Tyr Pro Met
145                 150                 155                 160

Ser Trp Val Arg Gln Ala Pro Gly Lys Gly Leu Glu Trp Val Ser Thr
                165                 170                 175

Ile Ser Thr Tyr Gly Glu Pro Arg Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Lys Gly
    210                 215                 220

Ala Gly Thr Ser Ser Tyr Leu Pro Gln Arg Gly Asn Trp Asp Gln Gly
225                 230                 235                 240

Thr Gln Val Thr Ile Ser Ser
                245

<210> SEQ ID NO 46
<211> LENGTH: 254
<212> TYPE: PRT
<213> ORGANISM: Lama glama

<400> SEQUENCE: 46

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Arg Arg Tyr
            20                  25                  30

Ala Met Gly Trp Tyr Arg Gln Ala Pro Gly Lys Gln Arg Glu Leu Val
        35                  40                  45

Ala Ala Ile Thr Ser Gly Gly Arg Thr Ser Val Ala Asp Thr Val Lys
    50                  55                  60
```

```
Gly Arg Phe Thr Ile Ser Ser Asp Asn Ala Lys Asn Thr Val Tyr Leu
 65                  70                  75                  80

Gln Met Asn Ser Leu Lys Pro Glu Asp Ala Ala Val Tyr Tyr Cys Thr
                 85                  90                  95

Leu Tyr Asn Ser Thr Thr Asn Tyr Tyr Asn Gln Ser Pro Ser Ser Trp
                100                 105                 110

Gly Gln Gly Thr Gln Val Thr Val Ser Ser Glu Pro Lys Thr Pro Lys
            115                 120                 125

Pro Gln Pro Ala Ala Ala Gln Val Gln Leu Gln Glu Ser Gly Gly Gly
            130                 135                 140

Leu Val Gln Ala Gly Asp Ser Leu Arg Leu Ser Cys Ala Ala Ser Gly
145                 150                 155                 160

Arg Thr Phe Thr Met Gly Trp Phe Arg Gln Ala Pro Gly Lys Glu Arg
                165                 170                 175

Gln Phe Val Ala Ala Leu Thr Trp Thr Gly Gly Ser Pro Val Tyr Ala
                180                 185                 190

Asp Ser Val Lys Gly Arg Phe Thr Thr Trp Arg Val Leu Asp Asn Asn
            195                 200                 205

Thr Val Tyr Leu His Met Asn Ser Leu Lys Pro Glu Asp Thr Ala Val
        210                 215                 220

Tyr His Cys Ala Ala Arg Thr Tyr Tyr Gly Asn Ile Ser Glu Tyr
225                 230                 235                 240

Tyr Asp Tyr Trp Gly Gln Gly Thr Gln Val Thr Val Ser Ser
                245                 250

<210> SEQ ID NO 47
<211> LENGTH: 254
<212> TYPE: PRT
<213> ORGANISM: Lama glama

<400> SEQUENCE: 47

Gln Val Gln Leu Gln Asp Ser Gly Gly Gly Leu Val Gln Ala Gly Gly
 1               5                  10                  15

Ser Leu Arg Leu Ser Cys Ala Ala Ser Gly Arg Thr Phe Arg Arg Tyr
                20                  25                  30

Ala Met Gly Trp Tyr Arg Gln Ala Pro Gly Lys Gln Arg Val Leu Val
                35                  40                  45

Ala Ala Ile Thr Ser Asn Gly Arg Pro Ser Val Ala Asp Ser Val Lys
            50                  55                  60

Gly Arg Phe Thr Ile Ser Ser Asp Thr Ala Lys Asn Thr Val Tyr Leu
 65                  70                  75                  80

Gln Met Asn Ser Leu Lys Pro Glu Asp Thr Ala Leu Tyr Tyr Cys Thr
                 85                  90                  95

Leu Tyr Asn Thr Ser Ala Asp Tyr Tyr Asn Gln Ser Pro Ser Ser Trp
                100                 105                 110

Gly Gln Gly Thr Gln Val Thr Val Leu Ser Glu Pro Lys Thr Pro Lys
            115                 120                 125

Pro Gln Pro Ala Ala Ala Gln Val Gln Leu Gln Glu Ser Gly Gly Gly
            130                 135                 140

Leu Val Gln Ala Gly Asp Ser Leu Arg Leu Ser Cys Ala Ala Ser Gly
145                 150                 155                 160

Arg Thr Phe Thr Met Gly Trp Phe Arg Gln Ala Pro Gly Lys Glu Arg
                165                 170                 175

Gln Phe Val Ala Ala Leu Thr Trp Thr Gly Gly Ser Pro Val Tyr Ala
```

```
            180                 185                 190
Asp Ser Val Lys Gly Arg Phe Thr Thr Trp Arg Val Leu Asp Asn Asn
            195                 200                 205

Thr Val Tyr Leu His Met Asn Ser Leu Lys Pro Glu Asp Thr Ala Val
            210                 215                 220

Tyr His Cys Ala Ala Ala Arg Thr Tyr Tyr Gly Asn Ile Ser Glu Tyr
225                 230                 235                 240

Tyr Asp Tyr Trp Gly Gln Gly Thr Gln Val Thr Val Ser Ser
            245                 250

<210> SEQ ID NO 48
<211> LENGTH: 2804
<212> TYPE: PRT
<213> ORGANISM: Homo sapiens

<400> SEQUENCE: 48

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
            85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
            130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
            165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
            195                 200                 205

Ser Cys Asn Ile Ser Ser Gly Glu Met Gln Lys Gly Leu Trp Glu Gln
            210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
            245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
            290                 295                 300
```

```
Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
        610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
                660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
        690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
```

```
                    725                 730                 735
His Cys Thr Met Ser Gly Val Pro Gly Ser Leu Leu Pro Asp Ala Val
            740                 745                 750
Leu Ser Ser Pro Leu Ser His Arg Ser Lys Arg Ser Leu Ser Cys Arg
            755                 760                 765
Pro Pro Met Val Lys Leu Val Cys Pro Ala Asp Asn Leu Arg Ala Glu
770             775                 780
Gly Leu Glu Cys Thr Lys Thr Cys Gln Asn Tyr Asp Leu Glu Cys Met
785             790                 795                 800
Ser Met Gly Cys Val Ser Gly Cys Leu Cys Pro Pro Gly Met Val Arg
                805                 810                 815
His Glu Asn Arg Cys Val Ala Leu Glu Arg Cys Pro Cys Phe His Gln
                820                 825                 830
Gly Lys Glu Tyr Ala Pro Gly Glu Thr Val Lys Ile Gly Cys Asn Thr
                835                 840                 845
Cys Val Cys Arg Asp Arg Lys Trp Asn Cys Thr Asp His Val Cys Asp
850                 855                 860
Ala Thr Cys Ser Thr Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
                885                 890                 895
Tyr Cys Gly Ser Asn Pro Gly Thr Phe Arg Ile Leu Val Gly Asn Lys
                900                 905                 910
Gly Cys Ser His Pro Ser Val Lys Cys Lys Lys Arg Val Thr Ile Leu
                915                 920                 925
Val Glu Gly Gly Glu Ile Glu Leu Phe Asp Gly Glu Val Asn Val Lys
930                 935                 940
Arg Pro Met Lys Asp Glu Thr His Phe Glu Val Val Glu Ser Gly Arg
945                 950                 955                 960
Tyr Ile Ile Leu Leu Leu Gly Lys Ala Leu Ser Val Val Trp Asp Arg
                965                 970                 975
His Leu Ser Ile Ser Val Val Leu Lys Gln Thr Tyr Gln Glu Lys Val
                980                 985                 990
Cys Gly Leu Cys Gly Asn Phe Asp Gly Ile Gln Asn Asn Asp Leu Thr
                995                 1000                1005
Ser Ser Asn Leu Gln Val Glu Glu Asp Pro Val Asp Phe Gly Asn
            1010                1015                1020
Ser Trp Lys Val Ser Ser Gln Cys Ala Asp Thr Arg Lys Val Pro
            1025                1030                1035
Leu Asp Ser Ser Pro Ala Thr Cys His Asn Asn Ile Met Lys Gln
            1040                1045                1050
Thr Met Val Asp Ser Ser Cys Arg Ile Leu Thr Ser Asp Val Phe
            1055                1060                1065
Gln Asp Cys Asn Lys Leu Val Asp Pro Glu Pro Tyr Leu Asp Val
            1070                1075                1080
Cys Ile Tyr Asp Thr Cys Ser Cys Glu Ser Ile Gly Asp Cys Ala
            1085                1090                1095
Cys Phe Cys Asp Thr Ile Ala Ala Tyr Ala His Val Cys Ala Gln
            1100                1105                1110
His Gly Lys Val Val Thr Trp Arg Thr Ala Thr Leu Cys Pro Gln
            1115                1120                1125
Ser Cys Glu Glu Arg Asn Leu Arg Glu Asn Gly Tyr Glu Cys Glu
            1130                1135                1140
```

```
Trp Arg Tyr Asn Ser Cys Ala Pro Ala Cys Gln Val Thr Cys Gln
1145            1150                1155

His Pro Glu Pro Leu Ala Cys Pro Val Gln Cys Val Glu Gly Cys
1160            1165                1170

His Ala His Cys Pro Pro Gly Lys Ile Leu Asp Glu Leu Leu Gln
1175            1180                1185

Thr Cys Val Asp Pro Glu Asp Cys Pro Val Cys Glu Val Ala Gly
1190            1195                1200

Arg Arg Phe Ala Ser Gly Lys Lys Val Thr Leu Asn Pro Ser Asp
1205            1210                1215

Pro Glu His Cys Gln Ile Cys His Cys Asp Val Val Asn Leu Thr
1220            1225                1230

Cys Glu Ala Cys Gln Glu Pro Gly Gly Leu Val Val Pro Pro Thr
1235            1240                1245

Asp Ala Pro Val Ser Pro Thr Thr Leu Tyr Val Glu Asp Ile Ser
1250            1255                1260

Glu Pro Pro Leu His Asp Phe Tyr Cys Ser Arg Leu Leu Asp Leu
1265            1270                1275

Val Phe Leu Leu Asp Gly Ser Ser Arg Leu Ser Glu Ala Glu Phe
1280            1285                1290

Glu Val Leu Lys Ala Phe Val Val Asp Met Met Glu Arg Leu Arg
1295            1300                1305

Ile Ser Gln Lys Trp Val Arg Val Ala Val Val Glu Tyr His Asp
1310            1315                1320

Gly Ser His Ala Tyr Ile Gly Leu Lys Asp Arg Lys Arg Pro Ser
1325            1330                1335

Glu Leu Arg Arg Ile Ala Ser Gln Val Lys Tyr Ala Gly Ser Gln
1340            1345                1350

Val Ala Ser Thr Ser Glu Val Leu Lys Tyr Thr Leu Phe Gln Ile
1355            1360                1365

Phe Ser Lys Ile Asp Arg Pro Glu Ala Ser Arg Ile Ala Leu Leu
1370            1375                1380

Leu Met Ala Ser Gln Glu Pro Gln Arg Met Ser Arg Asn Phe Val
1385            1390                1395

Arg Tyr Val Gln Gly Leu Lys Lys Lys Lys Val Ile Val Ile Pro
1400            1405                1410

Val Gly Ile Gly Pro His Ala Asn Leu Lys Gln Ile Arg Leu Ile
1415            1420                1425

Glu Lys Gln Ala Pro Glu Asn Lys Ala Phe Val Leu Ser Ser Val
1430            1435                1440

Asp Glu Leu Glu Gln Gln Arg Asp Glu Ile Val Ser Tyr Leu Cys
1445            1450                1455

Asp Leu Ala Pro Glu Ala Pro Pro Pro Thr Leu Pro Pro His Met
1460            1465                1470

Ala Gln Val Thr Val Gly Pro Gly Leu Arg Asn Ser Met Val Leu
1475            1480                1485

Asp Val Ala Phe Val Leu Glu Gly Ser Asp Lys Ile Gly Glu Ala
1490            1495                1500

Asp Phe Asn Arg Ser Lys Glu Phe Met Glu Glu Val Ile Gln Arg
1505            1510                1515

Met Asp Val Gly Gln Asp Ser Ile His Val Thr Val Leu Gln Tyr
1520            1525                1530
```

-continued

```
Ser Tyr Met Val Thr Val Glu Tyr Pro Phe Ser Glu Ala Gln Ser
    1535                1540                1545

Lys Gly Asp Ile Leu Gln Arg Val Arg Glu Ile Arg Tyr Gln Gly
    1550                1555                1560

Gly Asn Arg Thr Asn Thr Gly Leu Ala Leu Arg Tyr Leu Ser Asp
    1565                1570                1575

His Ser Phe Leu Val Ser Gln Gly Asp Arg Glu Gln Ala Pro Asn
    1580                1585                1590

Leu Val Tyr Met Val Thr Gly Asn Pro Ala Ser Asp Glu Ile Lys
    1595                1600                1605

Arg Leu Pro Gly Asp Ile Gln Val Val Pro Ile Gly Val Gly Pro
    1610                1615                1620

Asn Ala Asn Val Gln Glu Leu Glu Arg Ile Gly Trp Pro Asn Ala
    1625                1630                1635

Pro Ile Leu Ile Gln Asp Phe Glu Thr Leu Pro Arg Glu Ala Pro
    1640                1645                1650

Asp Leu Val Leu Gln Arg Cys Cys Ser Gly Glu Gly Leu Gln Ile
    1655                1660                1665

Pro Thr Leu Ser Pro Ala Pro Asp Cys Ser Gln Pro Leu Asp Val
    1670                1675                1680

Ile Leu Leu Leu Asp Gly Ser Ser Ser Phe Pro Ala Ser Tyr Phe
    1685                1690                1695

Asp Glu Met Lys Ser Phe Ala Lys Ala Phe Ile Ser Lys Ala Asn
    1700                1705                1710

Ile Gly Pro Arg Leu Thr Gln Val Ser Val Leu Gln Tyr Gly Ser
    1715                1720                1725

Ile Thr Thr Ile Asp Val Pro Trp Asn Val Val Pro Glu Lys Ala
    1730                1735                1740

His Leu Leu Ser Leu Val Asp Val Met Gln Arg Glu Gly Gly Pro
    1745                1750                1755

Ser Gln Ile Gly Asp Ala Leu Gly Phe Ala Val Arg Tyr Leu Thr
    1760                1765                1770

Ser Glu Met His Gly Ala Arg Pro Gly Ala Ser Lys Ala Val Val
    1775                1780                1785

Ile Leu Val Thr Asp Val Ser Val Asp Ser Val Asp Ala Ala Ala
    1790                1795                1800

Asp Ala Ala Arg Ser Asn Arg Val Thr Val Phe Pro Ile Gly Ile
    1805                1810                1815

Gly Asp Arg Tyr Asp Ala Ala Gln Leu Arg Ile Leu Ala Gly Pro
    1820                1825                1830

Ala Gly Asp Ser Asn Val Val Lys Leu Gln Arg Ile Glu Asp Leu
    1835                1840                1845

Pro Thr Met Val Thr Leu Gly Asn Ser Phe Leu His Lys Leu Cys
    1850                1855                1860

Ser Gly Phe Val Arg Ile Cys Met Asp Glu Asp Gly Asn Glu Lys
    1865                1870                1875

Arg Pro Gly Asp Val Trp Thr Leu Pro Asp Gln Cys His Thr Val
    1880                1885                1890

Thr Cys Gln Pro Asp Gly Gln Thr Leu Leu Lys Ser His Arg Val
    1895                1900                1905

Asn Cys Asp Arg Gly Leu Arg Pro Ser Cys Pro Asn Ser Gln Ser
    1910                1915                1920

Pro Val Lys Val Glu Glu Thr Cys Gly Cys Arg Trp Thr Cys Pro
```

```
              1925                1930                1935

Cys Val Cys Thr Gly Ser Ser Thr Arg His Ile Val Thr Phe Asp
        1940                1945                1950

Gly Gln Asn Phe Lys Leu Thr Gly Ser Cys Ser Tyr Val Leu Phe
        1955                1960                1965

Gln Asn Lys Glu Gln Asp Leu Glu Val Ile Leu His Asn Gly Ala
        1970                1975                1980

Cys Ser Pro Gly Ala Arg Gln Gly Cys Met Lys Ser Ile Glu Val
        1985                1990                1995

Lys His Ser Ala Leu Ser Val Glu Leu His Ser Asp Met Glu Val
        2000                2005                2010

Thr Val Asn Gly Arg Leu Val Ser Val Pro Tyr Val Gly Gly Asn
        2015                2020                2025

Met Glu Val Asn Val Tyr Gly Ala Ile Met His Glu Val Arg Phe
        2030                2035                2040

Asn His Leu Gly His Ile Phe Thr Phe Thr Pro Gln Asn Asn Glu
        2045                2050                2055

Phe Gln Leu Gln Leu Ser Pro Lys Thr Phe Ala Ser Lys Thr Tyr
        2060                2065                2070

Gly Leu Cys Gly Ile Cys Asp Glu Asn Gly Ala Asn Asp Phe Met
        2075                2080                2085

Leu Arg Asp Gly Thr Val Thr Thr Asp Trp Lys Thr Leu Val Gln
        2090                2095                2100

Glu Trp Thr Val Gln Arg Pro Gly Gln Thr Cys Gln Pro Ile Leu
        2105                2110                2115

Glu Glu Gln Cys Leu Val Pro Asp Ser Ser His Cys Gln Val Leu
        2120                2125                2130

Leu Leu Pro Leu Phe Ala Glu Cys His Lys Val Leu Ala Pro Ala
        2135                2140                2145

Thr Phe Tyr Ala Ile Cys Gln Gln Asp Ser Cys His Gln Glu Gln
        2150                2155                2160

Val Cys Glu Val Ile Ala Ser Tyr Ala His Leu Cys Arg Thr Asn
        2165                2170                2175

Gly Val Cys Val Asp Trp Arg Thr Pro Asp Phe Cys Ala Met Ser
        2180                2185                2190

Cys Pro Pro Ser Leu Val Tyr Asn His Cys Glu His Gly Cys Pro
        2195                2200                2205

Arg His Cys Asp Gly Asn Val Ser Ser Cys Gly Asp His Pro Ser
        2210                2215                2220

Glu Gly Cys Phe Cys Pro Pro Asp Lys Val Met Leu Glu Gly Ser
        2225                2230                2235

Cys Val Pro Glu Glu Ala Cys Thr Gln Cys Ile Gly Glu Asp Gly
        2240                2245                2250

Val Gln His Gln Phe Leu Glu Ala Trp Val Pro Asp His Gln Pro
        2255                2260                2265

Cys Gln Ile Cys Thr Cys Leu Ser Gly Arg Lys Val Asn Cys Thr
        2270                2275                2280

Thr Gln Pro Cys Pro Thr Ala Lys Ala Pro Thr Cys Gly Leu Cys
        2285                2290                2295

Glu Val Ala Arg Leu Arg Gln Asn Ala Asp Gln Cys Cys Pro Glu
        2300                2305                2310

Tyr Glu Cys Val Cys Asp Pro Val Ser Cys Asp Leu Pro Pro Val
        2315                2320                2325
```

```
Pro His Cys Glu Arg Gly Leu Gln Pro Thr Leu Thr Asn Pro Gly
2330                 2335                 2340

Glu Cys Arg Pro Asn Phe Thr Cys Ala Cys Arg Lys Glu Glu Cys
2345                 2350                 2355

Lys Arg Val Ser Pro Pro Ser Cys Pro Pro His Arg Leu Pro Thr
2360                 2365                 2370

Leu Arg Lys Thr Gln Cys Cys Asp Glu Tyr Glu Cys Ala Cys Asn
2375                 2380                 2385

Cys Val Asn Ser Thr Val Ser Cys Pro Leu Gly Tyr Leu Ala Ser
2390                 2395                 2400

Thr Ala Thr Asn Asp Cys Gly Cys Thr Thr Thr Thr Cys Leu Pro
2405                 2410                 2415

Asp Lys Val Cys Val His Arg Ser Thr Ile Tyr Pro Val Gly Gln
2420                 2425                 2430

Phe Trp Glu Glu Gly Cys Asp Val Cys Thr Cys Thr Asp Met Glu
2435                 2440                 2445

Asp Ala Val Met Gly Leu Arg Val Ala Gln Cys Ser Gln Lys Pro
2450                 2455                 2460

Cys Glu Asp Ser Cys Arg Ser Gly Phe Thr Tyr Val Leu His Glu
2465                 2470                 2475

Gly Glu Cys Cys Gly Arg Cys Leu Pro Ser Ala Cys Glu Val Val
2480                 2485                 2490

Thr Gly Ser Pro Arg Gly Asp Ser Gln Ser Ser Trp Lys Ser Val
2495                 2500                 2505

Gly Ser Gln Trp Ala Ser Pro Glu Asn Pro Cys Leu Ile Asn Glu
2510                 2515                 2520

Cys Val Arg Val Lys Glu Glu Val Phe Ile Gln Gln Arg Asn Val
2525                 2530                 2535

Ser Cys Pro Gln Leu Glu Val Pro Val Cys Pro Ser Gly Phe Gln
2540                 2545                 2550

Leu Ser Cys Lys Thr Ser Ala Cys Cys Pro Ser Cys Arg Cys Glu
2555                 2560                 2565

Arg Met Glu Ala Cys Met Leu Asn Gly Thr Val Ile Gly Pro Gly
2570                 2575                 2580

Lys Thr Val Met Ile Asp Val Cys Thr Thr Cys Arg Cys Met Val
2585                 2590                 2595

Gln Val Gly Val Ile Ser Gly Phe Lys Leu Glu Cys Arg Lys Thr
2600                 2605                 2610

Thr Cys Asn Pro Cys Pro Leu Gly Tyr Lys Glu Glu Asn Asn Thr
2615                 2620                 2625

Gly Glu Cys Cys Gly Arg Cys Leu Pro Thr Ala Cys Thr Ile Gln
2630                 2635                 2640

Leu Arg Gly Gly Gln Ile Met Thr Leu Lys Arg Asp Glu Thr Leu
2645                 2650                 2655

Gln Asp Gly Cys Asp Thr His Phe Cys Lys Val Asn Glu Arg Gly
2660                 2665                 2670

Glu Tyr Phe Trp Glu Lys Arg Val Thr Gly Cys Pro Pro Phe Asp
2675                 2680                 2685

Glu His Lys Cys Leu Ala Glu Gly Gly Lys Ile Met Lys Ile Pro
2690                 2695                 2700

Gly Thr Cys Cys Asp Thr Cys Glu Glu Pro Glu Cys Asn Asp Ile
2705                 2710                 2715
```

```
Thr Ala Arg Leu Gln Tyr Val Lys Val Gly Ser Cys Lys Ser Glu
    2720                2725                2730

Val Glu Val Asp Ile His Tyr Cys Gln Gly Lys Cys Ala Ser Lys
    2735                2740                2745

Ala Met Tyr Ser Ile Asp Ile Asn Asp Val Gln Asp Gln Cys Ser
    2750                2755                2760

Cys Cys Ser Pro Thr Arg Thr Glu Pro Met Gln Val Ala Leu His
    2765                2770                2775

Cys Thr Asn Gly Ser Val Val Tyr His Glu Val Leu Asn Ala Met
    2780                2785                2790

Glu Cys Lys Cys Ser Pro Arg Lys Cys Ser Lys
    2795                2800

<210> SEQ ID NO 49
<211> LENGTH: 128
<212> TYPE: PRT
<213> ORGANISM: Lama glama

<400> SEQUENCE: 49

Ala Val Gln Leu Val Glu Ser Gly Gly Gly Leu Val Gln Ala Gly Asp
1               5                   10                  15

Ser Leu Arg Leu Ser Cys Val Val Ser Gly Thr Thr Phe Ser Ser Ala
                20                  25                  30

Ala Met Gly Trp Phe Arg Gln Ala Pro Gly Lys Glu Arg Glu Phe Val
            35                  40                  45

Gly Ala Ile Lys Trp Ser Gly Thr Ser Thr Tyr Tyr Thr Asp Ser Val
        50                  55                  60

Lys Gly Arg Phe Thr Ile Ser Arg Asp Asn Val Lys Asn Thr Val Tyr
65                  70                  75                  80

Leu Gln Met Asn Asn Leu Lys Pro Glu Asp Thr Gly Val Tyr Thr Cys
                85                  90                  95

Ala Ala Asp Arg Asp Arg Tyr Arg Asp Arg Met Gly Pro Met Thr Thr
            100                 105                 110

Thr Asp Phe Arg Phe Trp Gly Gln Gly Thr Gln Val Thr Val Ser Ser
        115                 120                 125

<210> SEQ ID NO 50
<211> LENGTH: 124
<212> TYPE: PRT
<213> ORGANISM: Lama glama

<400> SEQUENCE: 50

Gln Val Lys Leu Glu Glu Ser Gly Gly Gly Leu Val Gln Thr Gly Gly
1               5                   10                  15

Ser Leu Arg Leu Ser Cys Ala Ala Ser Gly Arg Thr Phe Ser Ser Phe
                20                  25                  30

Ala Met Gly Trp Phe Arg Gln Ala Pro Gly Arg Glu Arg Glu Phe Val
            35                  40                  45

Ala Ser Ile Gly Ser Ser Gly Ile Thr Thr Asn Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Leu Cys Tyr Cys
                85                  90                  95

Ala Val Asn Arg Tyr Gly Ile Pro Tyr Arg Ser Gly Thr Gln Tyr Gln
            100                 105                 110
```

Asn Trp Gly Gln Gly Thr Gln Val Thr Val Ser Ser
        115                 120

<210> SEQ ID NO 51
<211> LENGTH: 120
<212> TYPE: PRT
<213> ORGANISM: Lama glama

<400> SEQUENCE: 51

Glu Val Gln Leu Glu Glu Ser Gly Gly Leu Val Gln Pro Gly Gly
1               5                   10                  15

Ser Leu Arg Leu Ser Cys Ala Ala Ser Gly Leu Thr Phe Asn Asp Tyr
        20                  25                  30

Ala Met Gly Trp Tyr Arg Gln Ala Pro Gly Lys Glu Arg Asp Met Val
        35                  40                  45

Ala Thr Ile Ser Ile Gly Gly Arg Thr Tyr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Ile Tyr Tyr Cys Val
                85                  90                  95

Ala His Arg Gln Thr Val Val Arg Gly Pro Tyr Leu Leu Trp Gly Gln
            100                 105                 110

Gly Thr Gln Val Thr Val Ser Ser
        115                 120

<210> SEQ ID NO 52
<211> LENGTH: 123
<212> TYPE: PRT
<213> ORGANISM: Lama glama

<400> SEQUENCE: 52

Gln Val Gln Leu Val Glu Ser Gly Gly Lys Leu Val Gln Ala Gly Gly
1               5                   10                  15

Ser Leu Arg Leu Ser Cys Ala Ala Ser Gly Arg Thr Phe Ser Asn Tyr
        20                  25                  30

Ala Met Gly Trp Phe Arg Gln Ala Pro Gly Lys Glu Arg Glu Phe Val
        35                  40                  45

Ala Gly Ser Gly Arg Ser Asn Ser Tyr Asn Tyr Tyr Ser Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Thr Asn Leu Trp Pro Arg Asp Arg Asn Leu Tyr Ala Tyr
            100                 105                 110

Trp Gly Gln Gly Thr Gln Val Thr Val Ser Ser
        115                 120

<210> SEQ ID NO 53
<211> LENGTH: 125
<212> TYPE: PRT
<213> ORGANISM: Lama glama

<400> SEQUENCE: 53

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ser Leu Gly Ile Tyr

```
                 20                  25                  30
Arg Met Gly Trp Phe Arg Gln Val Pro Gly Lys Glu Arg Glu Phe Val
             35                  40                  45
Ala Ala Ile Ser Trp Ser Gly Gly Thr Thr Arg Tyr Leu Asp Ser Val
         50                  55                  60
Lys Gly Arg Phe Thr Ile Ser Arg Asp Ser Thr Lys Asn Ala Val Tyr
 65                  70                  75                  80
Leu Gln Met Asn Ser Leu Lys Pro Glu Asp Thr Ala Val Tyr Tyr Cys
                 85                  90                  95
Ala Val Asp Ser Ser Gly Arg Leu Tyr Trp Thr Leu Ser Thr Ser Tyr
                100                 105                 110
Asp Tyr Trp Gly Gln Gly Thr Gln Val Thr Val Ser Ser
                115                 120                 125

<210> SEQ ID NO 54
<211> LENGTH: 125
<212> TYPE: PRT
<213> ORGANISM: Lama glama

<400> SEQUENCE: 54

Gln Val Gln Leu Val Glu Phe Gly Gly Gly Leu Val Gln Ala Gly Asp
 1               5                  10                  15
Ser Leu Arg Leu Ser Cys Ala Ala Ser Gly Arg Ser Leu Gly Ile Tyr
             20                  25                  30
Lys Met Ala Trp Phe Arg Gln Val Pro Gly Lys Glu Arg Glu Phe Val
             35                  40                  45
Ala Ala Ile Ser Trp Ser Gly Gly Thr Thr Arg Tyr Ile Asp Ser Val
         50                  55                  60
Lys Gly Arg Phe Thr Leu Ser Arg Asp Asn Thr Lys Asn Met Val Tyr
 65                  70                  75                  80
Leu Gln Met Asn Ser Leu Lys Pro Asp Asp Thr Ala Val Tyr Tyr Cys
                 85                  90                  95
Ala Val Asp Ser Ser Gly Arg Leu Tyr Trp Thr Leu Ser Thr Ser Tyr
                100                 105                 110
Asp Tyr Trp Gly Gln Gly Thr Gln Val Thr Val Ser Ser
                115                 120                 125

<210> SEQ ID NO 55
<211> LENGTH: 124
<212> TYPE: PRT
<213> ORGANISM: Lama glama

<400> SEQUENCE: 55

Glu Val Gln Leu Val Glu Ser Gly Gly Gly Leu Val Gln Ala Gly Gly
 1               5                  10                  15
Ser Leu Ser Leu Ser Cys Ala Ala Ser Gly Arg Thr Phe Ser Pro Tyr
             20                  25                  30
Thr Met Gly Trp Phe Arg Gln Ala Pro Gly Lys Glu Arg Glu Phe Leu
             35                  40                  45
Ala Gly Val Thr Trp Ser Gly Ser Ser Thr Phe Tyr Gly Asp Ser Val
         50                  55                  60
Lys Gly Arg Phe Thr Ala Ser Arg Asp Ser Ala Lys Asn Thr Val Thr
 65                  70                  75                  80
Leu Glu Met Asn Ser Leu Asn Pro Glu Asp Thr Ala Val Tyr Tyr Cys
                 85                  90                  95
Ala Ala Ala Tyr Gly Gly Gly Leu Tyr Arg Asp Pro Arg Ser Tyr Asp
```

```
                100              105              110
Tyr Trp Gly Arg Gly Thr Gln Val Thr Val Ser Ser
        115              120

<210> SEQ ID NO 56
<211> LENGTH: 131
<212> TYPE: PRT
<213> ORGANISM: Lama glama

<400> SEQUENCE: 56

Ala Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Asp Ala Trp
            20                  25                  30

Pro Ile Ala Trp Phe Arg Gln Ala Pro Gly Lys Glu Arg Glu Gly Val
        35                  40                  45

Ser Cys Ile Arg Asp Gly Thr Thr Tyr Tyr Ala Asp Ser Val Lys Gly
    50                  55                  60

Arg Phe Thr Ile Ser Ser Asp Asn Ala Asn Asn Thr Val Tyr Leu Gln
65                  70                  75                  80

Thr Asn Ser Leu Lys Pro Glu Asp Thr Ala Val Tyr Tyr Cys Ala Ala
                85                  90                  95

Pro Ser Gly Pro Ala Thr Gly Ser Ser His Thr Phe Gly Ile Tyr Trp
            100                 105                 110

Asn Leu Arg Asp Asp Tyr Asp Asn Trp Gly Gln Gly Thr Gln Val Thr
        115                 120                 125

Val Ser Ser
    130

<210> SEQ ID NO 57
<211> LENGTH: 126
<212> TYPE: PRT
<213> ORGANISM: Lama glama

<400> SEQUENCE: 57

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp His Tyr
            20                  25                  30

Thr Ile Gly Trp Phe Arg Gln Val Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Thr Leu Glu Pro Asp Asp Thr Ala Val Tyr Tyr Cys
                85                  90                  95

Ala Ala Gly Gly Leu Leu Leu Arg Val Glu Glu Leu Gln Ala Ser Asp
            100                 105                 110

Tyr Asp Tyr Trp Gly Gln Gly Ile Gln Val Thr Val Ser Ser
        115                 120                 125

<210> SEQ ID NO 58
<211> LENGTH: 128
<212> TYPE: PRT
<213> ORGANISM: Lama glama

<400> SEQUENCE: 58
```

```
Ala Val Gln Leu Val Asp Ser Gly Gly Gly Leu Val Gln Pro Gly Gly
1               5                   10                  15

Ser Leu Arg Leu Ser Cys Thr Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ala Cys Ile Ser Asn Ser Asp Gly Ser Thr Tyr Tyr Gly Asp Ser Val
    50                  55                  60

Lys Gly Arg Phe Thr Ile Ser Arg Asp Asn Ala Lys Thr Thr Val Tyr
65                  70                  75                  80

Leu Gln Met Asn Ser Leu Lys Pro Glu Asp Thr Ala Val Tyr Tyr Cys
                85                  90                  95

Ala Thr Ala Asp Arg His Tyr Ser Ala Ser His His Pro Phe Ala Asp
            100                 105                 110

Phe Ala Phe Asn Ser Trp Gly Gln Gly Thr Gln Val Thr Val Ser Ser
            115                 120                 125
```

<210> SEQ ID NO 59
<211> LENGTH: 120
<212> TYPE: PRT
<213> ORGANISM: Lama glama

<400> SEQUENCE: 59

```
Glu Val Gln Leu Val Glu Ser Gly Gly Gly Leu Val Gln Ala Gly Gly
1               5                   10                  15

Ser Leu Arg Leu Ser Cys Ala Ala Tyr Gly Leu Thr Phe Trp Arg Ala
            20                  25                  30

Ala Met Ala Trp Phe Arg Arg Ala Pro Gly Lys Glu Arg Glu Leu Val
        35                  40                  45

Val Ala Arg Asn Trp Gly Asp Gly Ser Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Arg Thr Tyr Gly Ser Ala Thr Tyr Asp Ile Trp Gly Gln
            100                 105                 110

Gly Thr Gln Val Thr Val Ser Ser
            115                 120
```

<210> SEQ ID NO 60
<211> LENGTH: 123
<212> TYPE: PRT
<213> ORGANISM: Lama glama

<400> SEQUENCE: 60

```
Glu Val Gln Leu Val Glu Ser Gly Gly Gly Leu Val Gln Asp Gly Gly
1               5                   10                  15

Ser Leu Arg Leu Ser Cys Ile Phe Ser Gly Arg Thr Phe Ala Asn Tyr
            20                  25                  30

Ala Met Gly Trp Phe Arg Gln Ala Pro Gly Lys Glu Arg Glu Phe Val
        35                  40                  45

Ala Ala Ile Asn Arg Asn Gly Gly Thr Thr Tyr Ala Asp Ala Leu
    50                  55                  60

Lys Gly Arg Phe Thr Ile Ser Arg Asp Asn Thr Lys Asn Thr Ala Phe
65                  70                  75                  80
```

-continued

Leu Gln Met Asn Ser Leu Lys Pro Asp Asp Thr Ala Val Tyr Tyr Cys
                85                  90                  95

Ala Ala Arg Glu Trp Pro Phe Ser Thr Ile Pro Ser Gly Trp Arg Tyr
            100                 105                 110

Trp Gly Gln Gly Thr Gln Val Thr Val Ser Ser
            115                 120

<210> SEQ ID NO 61
<211> LENGTH: 125
<212> TYPE: PRT
<213> ORGANISM: Lama glama

<400> SEQUENCE: 61

Asp Val Gln Leu Val Glu Ser Gly Gly Gly Trp Val Gln Pro Gly Gly
1               5                   10                  15

Ser Leu Arg Leu Ser Cys Ala Ala Ser Gly Pro Thr Ala Ser Ser His
            20                  25                  30

Ala Ile Gly Trp Phe Arg Gln Ala Pro Gly Lys Glu Arg Glu Phe Val
        35                  40                  45

Val Gly Ile Asn Arg Gly Gly Val Thr Arg Asp Tyr Ala Asp Ser Val
    50                  55                  60

Lys Gly Arg Phe Ala Val Ser Arg Asp Asn Val Lys Asn Thr Val Tyr
65                  70                  75                  80

Leu Gln Met Asn Arg Leu Lys Pro Glu Asp Ser Ala Ile Tyr Ile Cys
                85                  90                  95

Ala Ala Arg Pro Glu Tyr Ser Phe Thr Ala Met Ser Lys Gly Asp Met
            100                 105                 110

Asp Tyr Trp Gly Lys Gly Thr Leu Val Thr Val Ser Ser
            115                 120                 125

<210> SEQ ID NO 62
<211> LENGTH: 126
<212> TYPE: PRT
<213> ORGANISM: Lama glama

<400> SEQUENCE: 62

Glu Val Gln Leu Val Glu Ser Gly Gly Gly Leu Val Lys Ala Gly Ala
1               5                   10                  15

Ser Leu Arg Leu Ser Cys Ala Ala Ser Gly Arg Thr Phe Ser Ser Leu
            20                  25                  30

Pro Met Ala Trp Phe Arg Gln Ala Pro Gly Lys Glu Arg Glu Phe Val
        35                  40                  45

Ala Phe Ile Gly Ser Asp Ser Ser Thr Leu Tyr Thr Ser Ser Val Arg
    50                  55                  60

Gly Arg Phe Thr Ile Ser Arg Asp Asn Gly Lys Asn Thr Val Tyr Leu
65                  70                  75                  80

Gln Met Met Asn Leu Lys Pro Glu Asp Thr Ala Val Tyr Tyr Cys Ala
                85                  90                  95

Ala Arg Ser Ser Ala Phe Ser Ser Gly Ile Tyr Tyr Arg Glu Gly Ser
            100                 105                 110

Tyr Ala Tyr Trp Gly Gln Gly Thr Gln Val Thr Val Ser Ser
            115                 120                 125

<210> SEQ ID NO 63
<211> LENGTH: 125
<212> TYPE: PRT
<213> ORGANISM: Lama glama

```
<400> SEQUENCE: 63

Gln Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Phe Ser Thr Tyr
            20                  25                  30

Ala Leu Gly Trp Phe Arg Gln Val Pro Gly Lys Gly Arg Glu Phe Ile
        35                  40                  45

Ala Val Ile Tyr Trp Arg Asp Gly Ser Ser Leu Tyr Ser Asp Ser Val
    50                  55                  60

Lys Gly Arg Phe Thr Ile Ser Lys Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg His Asp Ser Arg Gly Thr Tyr Tyr Ser Ser Arg Gly Tyr
            100                 105                 110

Asp Tyr Trp Gly Gln Gly Thr Gln Val Thr Val Ser Ser
        115                 120                 125

<210> SEQ ID NO 64
<211> LENGTH: 122
<212> TYPE: PRT
<213> ORGANISM: Lama glama

<400> SEQUENCE: 64

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Lys Asp Met Ala
            20                  25                  30

Trp Phe Arg Gln Pro Pro Gly Lys Glu Arg Glu Phe Val Ala Val Ile
        35                  40                  45

Tyr Ser Ser Asp Gly Ser Thr Leu Val Ala Ala Ser Val Lys Gly Arg
    50                  55                  60

Phe Thr Ile Ser Arg Asp Asn Ala Lys Asn Thr Val Tyr Leu Gln Met
65                  70                  75                  80

Thr Ser Leu Lys Pro Ala Asp Thr Ala Val Tyr Tyr Cys Ala Thr Ser
                85                  90                  95

Arg Gly Tyr Ser Gly Thr Tyr Tyr Ser Thr Ser Arg Tyr Asp Tyr Trp
            100                 105                 110

Gly Gln Gly Thr Gln Val Thr Val Ser Ser
        115                 120

<210> SEQ ID NO 65
<211> LENGTH: 122
<212> TYPE: PRT
<213> ORGANISM: Lama glama

<400> SEQUENCE: 65

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Lys Asp Met Ala
            20                  25                  30

Trp Phe Arg Gln Pro Pro Gly Lys Glu Arg Glu Phe Val Ala Val Ile
        35                  40                  45

Tyr Ser Ser Asp Gly Ser Thr Leu Val Ala Ala Ser Val Thr Gly Arg
    50                  55                  60
```

```
Phe Thr Ile Ser Arg Asp Asn Ala Lys Asn Met Val Tyr Leu Gln Met
 65                 70                  75                  80

Thr Ser Leu Lys Pro Ala Asp Thr Ala Val Tyr Tyr Cys Ala Ser Ser
             85                  90                  95

Arg Gly Tyr Ser Gly Thr Tyr Tyr Ser Thr Ser Arg Tyr Asp Tyr Trp
            100                 105                 110

Gly Gln Gly Thr Gln Val Thr Val Ser Ser
            115                 120
```

```
<210> SEQ ID NO 66
<211> LENGTH: 23
<212> TYPE: DNA
<213> ORGANISM: Artificial
<220> FEATURE:
<223> OTHER INFORMATION: leader specific primer

<400> SEQUENCE: 66
ggctgagctc ggtggtcctg gct                                         23

<210> SEQ ID NO 67
<211> LENGTH: 45
<212> TYPE: DNA
<213> ORGANISM: Artificial
<220> FEATURE:
<223> OTHER INFORMATION: oligo d(T) primer

<400> SEQUENCE: 67
aactggaaga attcgcggcc gcaggaattt ttttttttt ttttt                  45

<210> SEQ ID NO 68
<211> LENGTH: 42
<212> TYPE: DNA
<213> ORGANISM: Artificial
<220> FEATURE:
<223> OTHER INFORMATION: A3for PCR primer

<400> SEQUENCE: 68
ctggtgctgc agaggtgaag cttcggagag gggctgcaga tc                    42

<210> SEQ ID NO 69
<211> LENGTH: 42
<212> TYPE: DNA
<213> ORGANISM: Artificial
<220> FEATURE:
<223> OTHER INFORMATION: A3back PCR primer

<400> SEQUENCE: 69
atccatgcaa atcctctaga atccagagca cagtttgtgg ag                    42

<210> SEQ ID NO 70
<211> LENGTH: 45
<212> TYPE: DNA
<213> ORGANISM: Artificial
<220> FEATURE:
<223> OTHER INFORMATION: A1for PCR primer

<400> SEQUENCE: 70
ccggtgagcc ccaccactct aagcttggag gacatctcgg aaccg                 45

<210> SEQ ID NO 71
<211> LENGTH: 42
<212> TYPE: DNA
<213> ORGANISM: Artificial
<220> FEATURE:
<223> OTHER INFORMATION: A1back PCR primer
```

```
<400> SEQUENCE: 71
ccccagggtc gaaaccctct agagccccgg gcccacagtg ac                           42

<210> SEQ ID NO 72
<211> LENGTH: 20
<212> TYPE: DNA
<213> ORGANISM: Artificial
<220> FEATURE:
<223> OTHER INFORMATION: sense primer

<400> SEQUENCE: 72
cccctggtcc cagttccctc                                                   20

<210> SEQ ID NO 73
<211> LENGTH: 20
<212> TYPE: DNA
<213> ORGANISM: Artificial
<220> FEATURE:
<223> OTHER INFORMATION: anti-sense primer

<400> SEQUENCE: 73
tgtgctcgcg gggccggtac                                                   20

<210> SEQ ID NO 74
<211> LENGTH: 47
<212> TYPE: DNA
<213> ORGANISM: Artificial
<220> FEATURE:
<223> OTHER INFORMATION: Reverse primer Sfi1

<400> SEQUENCE: 74
gtcctcgcaa ctgcggccca gccggcctgt gctcgcgggg ccggtac                     47

<210> SEQ ID NO 75
<211> LENGTH: 42
<212> TYPE: DNA
<213> ORGANISM: Artificial
<220> FEATURE:
<223> OTHER INFORMATION: Forward primer Not1

<400> SEQUENCE: 75
gtcctcgcaa ctgcgcggcc gccccctggt cccagttccc tc                          42

<210> SEQ ID NO 76
<211> LENGTH: 60
<212> TYPE: DNA
<213> ORGANISM: Artificial
<220> FEATURE:
<223> OTHER INFORMATION: primer

<400> SEQUENCE: 76
agagacaact ccaagaacac gctgtatctg caaatgaaca gcctgagagc tgaggacacg       60

<210> SEQ ID NO 77
<211> LENGTH: 20
<212> TYPE: PRT
<213> ORGANISM: Artificial
<220> FEATURE:
<223> OTHER INFORMATION: humanized sequence (A74S,N75K,P84A)

<400> SEQUENCE: 77

Arg Asp Asn Ser Lys Asn Thr Leu Tyr Leu Gln Met Asn Ser Leu Arg
1               5                   10                  15

Ala Glu Asp Thr
```

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
attactgtgc taaaggggcc ggtactagtt                              30

<210> SEQ ID NO 79
<211> LENGTH: 9
<212> TYPE: PRT
<213> ORGANISM: Artificial
<220> FEATURE:
<223> OTHER INFORMATION: humanized sequence (A74S,N75K,P84A,R94K)

<400> SEQUENCE: 79

Tyr Cys Ala Lys Gly Ala Gly Thr Ser
1               5

<210> SEQ ID NO 80
<211> LENGTH: 35
<212> TYPE: DNA
<213> ORGANISM: Artificial
<220> FEATURE:
<223> OTHER INFORMATION: primer

<400> SEQUENCE: 80
tcctgtgcag cctccggatt cactttcagt tggta                        35

<210> SEQ ID NO 81
<211> LENGTH: 11
<212> TYPE: PRT
<213> ORGANISM: Artificial
<220> FEATURE:
<223> OTHER INFORMATION: humanized sequence
      (N28T,N30S,A74S,N75K,P84A,R94K)

<400> SEQUENCE: 81

Ser Cys Ala Ala Ser Gly Phe Thr Phe Ser Trp
1               5                   10

<210> SEQ ID NO 82
<211> LENGTH: 253
<212> TYPE: DNA
<213> ORGANISM: Lama glama

<400> SEQUENCE: 82
aagcttgcat gcaaattcta tttcaaggag acagtcataa tgaaatacct attgcctacg    60
gcagccgctg gattgttatt actcgcggcc cagccggcca tggggcctaa taggcggccg   120
cacaggtgca gctgcaggag tcataatgag ggacccaggt caccgtctcc tcagaacaaa   180
aactcatctc agaagaggat ctgaatgggg ccgcacatca tcatcatcat cattaatgag   240
aattcactgg ccg                                                     253

<210> SEQ ID NO 83
<211> LENGTH: 61
<212> TYPE: PRT
<213> ORGANISM: Lama glama

<400> SEQUENCE: 83

```
Met Lys Tyr Leu Leu Pro Thr Ala Ala Ala Gly Leu Leu Leu Ala
1               5                   10                  15

Ala Gln Pro Ala Met Gly Pro Ala Ala Ala Gln Val Gln Leu Gln Glu
            20                  25                  30

Ser Gly Thr Gln Val Thr Val Ser Ser Glu Gln Lys Leu Ile Ser Glu
        35                  40                  45

Glu Asp Leu Asn Gly Ala Ala His His His His His His
50                  55                  60
```

<210> SEQ ID NO 84
<211> LENGTH: 98
<212> TYPE: PRT
<213> ORGANISM: Homo sapiens

<400> SEQUENCE: 84

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 85
<211> LENGTH: 121
<212> TYPE: PRT
<213> ORGANISM: Lama glama

<400> SEQUENCE: 85

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asn Phe Asn Trp Tyr
            20                  25                  30

Pro Met Ser Trp Val Arg Gln Ala Pro Gly Lys Gly Leu Glu Trp Val
        35                  40                  45

Ser Thr Ile Ser Thr Tyr Gly Glu Pro Arg Tyr Ala Asp Ser Val Lys
    50                  55                  60

Gly Arg Phe Thr Ile Ser Arg Asp Asn Ala Asn Asn Thr Leu Tyr Leu
65                  70                  75                  80

Gln Met Asn Ser Leu Arg Pro Glu Asp Thr Ala Val Tyr Tyr Cys Ala
                85                  90                  95

Arg Gly Ala Gly Thr Ser Ser Tyr Leu Pro Gln Arg Gly Asn Trp Asp
            100                 105                 110

Gln Gly Thr Gln Val Thr Ile Ser Ser
        115                 120
```